US012622975B2

(12) United States Patent
Xu et al.

(10) Patent No.: US 12,622,975 B2
(45) Date of Patent: May 12, 2026

(54) PEPTIDE-CONJUGATED PRODRUGS

(71) Applicant: BRANDEIS UNIVERSITY, Waltham, MA (US)

(72) Inventors: Bing Xu, Newton, MA (US); Jiaqing Wang, Waltham, MA (US)

(73) Assignee: BRANDEIS UNIVERSITY, Waltham, MA (US)

( * ) Notice: Subject to any disclaimer, the term of this patent is extended or adjusted under 35 U.S.C. 154(b) by 981 days.

(21) Appl. No.: 17/761,496

(22) PCT Filed: Sep. 18, 2020

(86) PCT No.: PCT/US2020/051410

§ 371 (c)(1), (2) Date: Mar. 17, 2022

(87) PCT Pub. No.: WO2021/055690

PCT Pub. Date: Mar. 25, 2021

(65) Prior Publication Data

US 2022/0387610 A1 Dec. 8, 2022

Related U.S. Application Data

(60) Provisional application No. 62/902,371, filed on Sep. 18, 2019.

(51) Int. Cl.

| | |
|---|---|
| ***A61K 38/07*** | (2006.01) |
| ***A61K 31/165*** | (2006.01) |
| ***A61K 47/64*** | (2017.01) |
| ***A61P 31/04*** | (2006.01) |
| ***C07K 5/06*** | (2006.01) |
| ***C07K 5/08*** | (2006.01) |
| ***C07K 5/10*** | (2006.01) |

(52) U.S. Cl.

CPC .............. *A61K 47/64* (2017.08); *A61P 31/04* (2018.01)

(58) Field of Classification Search

CPC ...... A61K 31/165; A61K 47/64; A61K 38/07; A61P 31/04; Y02A 50/30; C07K 5/10; C07K 5/08; C07K 5/06

See application file for complete search history.

(56) References Cited

U.S. PATENT DOCUMENTS

2017/0348337 A1 12/2017 Schmidt et al.

FOREIGN PATENT DOCUMENTS

WO WO-2016025627 A1 * 2/2016 ........... C07K 14/195

OTHER PUBLICATIONS

International Search Report and Written Opinion for corresponding Application No. PCT/US2020/051410 (mailed Feb. 4, 2021).

Weitz et al., "Functional and Structural Characterization of a Prokaryotic Peptide Transporter with Features Similar to Mammalian PEPT1," J. Biol. Chem. 282(5):2832-2839 (2007).

Garai et al., "Bacterial Peptide Transporters: Messengers of Nutrition to Virulence," Virulence 8(3):297-309 (2017).

Prabhala et al., "The Prototypical Proton-Coupled Oligopeptide Transporter YdgR from *Escherichia coli* Facilitates Chloramphenicol Uptake into Bacterial Cells," J. Biol. Chem. 293(3):1007-1017 (2018).

Li et al., "The Challenge of Efflux-mediated Antibiotic Resistance in Gram-negative Bacteria," Clin. Microbiol. Rev. 28:337-418 (2015).

Zhou et al., "Taurine Boosts Cellular Uptake of Small D-Peptides for Enzyme-Instructed Intracellular Molecular Self-Assembly," J. Am. Chem. Soc. 137(32):10040-10043 (2015).

Li et al., "Enzyme-Instructed Intracellular Molecular Self-Assembly to Boost Activity of Cisplatin Against Drug-Resistant Ovarian Cancer Cells," Angew. Chem. Int. Ed. 54(45):13307-13311 (2015).

Li et al., "Selectively Inducing Cancer Cell Death by Intracellular Enzyme-Instructed Self-Assembly (EISA) of Dipeptide Derivatives," Adv. Healthc. Mater. 6(15):1601400 (2017).

Chen et al., "Bacteria-Targeting Conjugates Based on Antimicrobial Peptide for Bacteria Diagnosis and Therapy," Mol. Pharm. 12(7):2505-2516 (2015).

* cited by examiner

*Primary Examiner* — Julie Ha

(74) *Attorney, Agent, or Firm* — Troutman Pepper Locke LLP (Rochester)

(57) ABSTRACT

The present disclosure relates to a conjugated prodrug comprising a peptide conjugated to an antibiotic molecules via a cleavable linker and pharmaceutical compositions thereof. Also disclosed are methods of enhancing the intracellular concentration of an antibiotic agent in a bacterium and methods of treating a patient for a bacterial infection.

14 Claims, 20 Drawing Sheets

Specification includes a Sequence Listing.

CLsuGG i) Fmoc-Gly-OH, DIEA; ii) 20% Piperdine; iii) Fmoc-Gly-OH, HBTU, DIEA; iv) CLRP, HBTU, DIEA; v) TFA.

CL 6 7

8 9 10

11

8

11

```
                          SEQUENCE LISTING

<160> NUMBER OF SEQ ID NOS: 6

<210> SEQ ID NO 1
<211> LENGTH: 4
<212> TYPE: PRT
<213> ORGANISM: Artificial
<220> FEATURE:
<223> OTHER INFORMATION: Tetrapeptide

<400> SEQUENCE: 1

Gly Gly Gly Gly
1


<210> SEQ ID NO 2
<211> LENGTH: 4
<212> TYPE: PRT
<213> ORGANISM: Artificial
<220> FEATURE:
<223> OTHER INFORMATION: Tetrapeptide

<400> SEQUENCE: 2

Phe Phe Arg Arg
1


<210> SEQ ID NO 3
<211> LENGTH: 4
<212> TYPE: PRT
<213> ORGANISM: Artificial
<220> FEATURE:
<223> OTHER INFORMATION: Tetrapeptide

<400> SEQUENCE: 3

Gly Gly Phe Phe
1


<210> SEQ ID NO 4
<211> LENGTH: 4
<212> TYPE: PRT
<213> ORGANISM: Artificial
<220> FEATURE:
<223> OTHER INFORMATION: Tetrapeptide

<400> SEQUENCE: 4

Phe Phe Gly Gly
1


<210> SEQ ID NO 5
<211> LENGTH: 5
<212> TYPE: PRT
<213> ORGANISM: Artificial
<220> FEATURE:
<223> OTHER INFORMATION: Pentapeptide

<400> SEQUENCE: 5

Gly Gly Gly Gly Gly
1               5


<210> SEQ ID NO 6
```

-continued

```
<211> LENGTH: 5
<212> TYPE: PRT
<213> ORGANISM: Artificial
<220> FEATURE:
<223> OTHER INFORMATION: Pentapeptide

<400> SEQUENCE: 6

Gly Gly Glu Gly Gly
1               5
```

PEPTIDE-CONJUGATED PRODRUGS

This application is a national stage application under 35 U.S.C. § 371 of International Application No. PCT/US2020/051410, filed Sep. 18, 2020, which claims the priority benefit of U.S. Provisional Patent Application No. 62/902,371, filed Sep. 18, 2019, which is hereby incorporated by reference in its entirety.

This invention was made with government support under grant number R21 AI130560 awarded by the National Institutes of Health, and grant number DMR-1420382 awarded by the National Science Foundation. The government has certain rights in the invention.

FIELD

The present invention relates to conjugated prodrugs that include a peptide conjugated to an antibiotic molecule via a cleavable linker and methods of use thereof. The invention also describes pharmaceutical compositions that include a pharmaceutically acceptable carrier and the conjugated prodrug.

BACKGROUND

Resulting from a large amount of antibiotics used for human and animal treatment, multidrug resistance (MDR) in bacteria remains a serious threat in public health (Neu, H. C., "The Crisis in Antibiotic Resistance," *Science* 257(5073): 1064-1073 (1992); Ghafourian et al., "Extended Spectrum Beta-Lactamases: Definition, Classification and Epidemiology. *Curr. Issues Mol. Biol.* 17(1):11-22 (2014); Carattoli, A., "Plasmids and the Spread of Resistance," *Int. J. Med. Microbiol.* 303(6-7):298-304 (2013); Butler et al., "Antibiotics in the Clinical Pipeline at the End of 2015," *J. Antibiot.* 70:3-24 (2017); and World Health Organization, WHO list of critically important antimicrobials for human medicine (WHO CIA list). No. WHO/NMH/FOS/FZD/19.1. World Health Organization: 2019). Drugs recently developed to thwart emerging antibiotic resistances, such as linezolid and the latest β-lactams, to vancomycin, have already lost effectiveness against some bacterial strains (Appelbaum, P. C., "2012 and Beyond: Potential for the Start of a Second Pre-Antibiotic Era?," *J. Antimicrob. Chemother.* 67(9):2062-2068 (2012); Arias & Murray, "Emergence and Management of Drug-Resistant Enterococcal Infections," *Expert Rev. Anti-infect. Ther.* 6(5):637-655 (2008); and Yong et al., "Characterization of a New Metallo-β-Lactamase Gene, blaNDM-1, and a Novel Erythromycin Esterase Gene Carried on a Unique Genetic Structure in *Klebsiella pneumoniae* Sequence Type 14 from India," *Antimicrob. Agents Chemother.* 53(12):5046-5054 (2009)). An even more serious threat may be the emergence of MDR Gram-negative bacteria that are resistant to essentially all of the available agents (Livermore, D., "The Need for New Antibiotics," *Clin. Microbiol. Infect.* 10:1-9 (2004)). Even more discouraging, the development of alternatives to the existing strategies for killing pathogenic bacteria has slowed dramatically over the past decades and failed to keep pace with the outbreak of resistance. Moreover, newer, successfully developed alternatives are strictly reserved to treat only the most serious infections. These factors have contributed to a limited antibiotic supply in the clinical pipeline (Butler et al., "Antibiotics in the Clinical Pipeline at the End of 2015," *J. Antibiot.* 70:3-24 (2017) and Blaskovich, M. A., "The Diminished Antimicrobial Pipeline," *Microbiol. Aust.* 40(2): 92-96 (2019)). Thus, there is an urgent need for developing new antimicrobial approaches against MDR bacterial pathogens.

Different strategies being used to discover and develop novel drugs to fight bacteria, mainly include (1) drug derivatives, which enhance the efficacy and safety of existing antibacterial agents via the modification of the drugs (Walsh et al., "Prospects for New Antibiotics: A Molecule-Centered Perspective," *J. Antibiot.* 67(1):7-22 (2014)) or increase specificity, e.g., efflux pump inhibitors (Goemaere et al., "New Peptide Deformylase Inhibitors and Cooperative Interaction: A Combination to Improve Antibacterial Activity," *J. Antimicrob. Chemother.* 67(6):1392-1400 (2012)); (2) discovery of new antibacterial agents, which involves the development of new tools to discover genomic or target-based antibiotics via previously unexplored mechanisms (Walsh & Wencewicz, "Prospects for New Antibiotics: A Molecule-Centered Perspective," *J. Antibiot.* 67(1):7-22 (2014)), and classical or whole-cell antibacterial assay to find antibiotics produced by microorganism of different sources (Singh et al., "Screening Strategies for Discovery of Antibacterial Natural Products," *Expert Rev. Anti-infect. Ther.* 9(8):589-613 (2011)); (3) bacteriophages or enzybiotics, which utilize bacteriophages or phage-lytic enzymes (Pastagia et al., "Lysins: The Arrival of Pathogen-Directed Anti-Infectives," *J. Med. Microbiol.* 62(10):1506-1516 (2013) and Bragg et al., "Bacteriophages as Potential Treatment Option for Antibiotic Resistant Bacteria," *Adv. Exp. Med. Biol.* 807:97-110 (2014)); (4) ecology/evolutionary biology approaches, which target the ecology and evolution of antibiotic resistance (Mosqueda et al., "Characterization of Plasmids Carrying the bla OXA-24/40 Carbapenemase Gene and the Genes Encoding the AbkA/AbkB Proteins of a Toxin/Antitoxin System," *J. Antimicrob. Chemother.* 69(10):2629-2633 (2014)). In comparison to developing a new drug that requires years of extensive testing, modifying existing antibiotics to achieve higher efficacy is safer, faster, and lower-cost. Therefore, developing feasible drug derivatives has become an active research focus.

Recently, the development of antibiotic derivatives has made significant progress. For example, Boger et al. reported that modifying the binding pocket of vancomycin, introducing a quaternary ammonium salt to the peripheral C-terminal, and linking (4-chlorobiphenyl)methyl (CBP) to the vancomycin disaccharide provide dual target binding and three independent action mechanisms, which directly overcome the molecular basis of vancomycin resistance (Okano et al., "Peripheral Modifications of [Ψ[$CH_2$NH]Tpg$^4$] Vancomycin with Added Synergistic Mechanisms of Action Provide Durable and Potent Antibiotics," *Proc. Natl. Acad. Sci.* 114(26):E5052-E5061 (2017) and Okano et al., "Total Syntheses and Initial Evaluation of [Ψ[C(═S)NH]Tpg$^4$] Vancomycin, [Ψ[C(═NH) NH] Tpg$^4$]Vancomycin, [Ψ[$CH_2$NH]Tpg$^4$] Vancomycin, and their (4-Chlorobiphenyl)methyl Derivatives: Synergistic Binding Pocket and Peripheral Modifications for the Glycopeptide Antibiotics," *J. Am. Chem. Soc.* 137(10):3693-3704 (2015)). The vancomycin analogues provide improvements in antibacterial potency against vancomycin-resistant enterococci and display little propensity for resistance. Others have reported the synthesis of novobiocin derivatives, which were more potent than novobiocin when being used in combination with polymyxin, the drug of last resort for treating Gram-negative infections (Mandler et al., "Novobiocin Enhances Polymyxin Activity by Stimulating Lipopolysaccharide Transport," *J. Am. Chem. Soc.* 140(22):6749-6753 (2018)). The novobiocin analogues not only allow the lower dosage of polymyxin, but also increase its efficacy and safety via inhibiting DNA gyrase, binding LptB, and disrupting the outer membrane. Others have also developed a synthetic siderophore-antibiotic conjugate (Ent-Cipro), which affords targeted antibacterial activity against pathogenic *E. coli* strains (Neumann et al., "Esterase-Catalyzed Siderophore Hydrolysis Activates an Enterobactin-Ciprofloxacin Conjugate and Confers Targeted Antibacterial Activity," *J. Am. Chem. Soc.* 140(15):5193-5201 (2018)). Ent-Cipro provides an excellent selectivity between non-pathogenic and pathogenic *E. coli*. Others have also synthesized a series of ciprofloxacin derivatives, which exhibited enhanced antibacterial activities against both sensitive and resistant *E. coli* (Xie et al., "Design and Synthesis of Theranostic Antibiotic Nanodrugs that Display Enhanced Antibacterial Activity and Luminescence," *Proc. Natl. Acad. Sci.* 114(32):8464-8469 (2017)).

In addition to these advances, there are reports to conjugate chloramphenicol ("CL") to amino acids. For example, U.S. Pat. No. 4,489,156 to Khanna et al. describes the direct conjugation of antigenic poly(amino acids) to the reduced nitro group of CL to generate conjugated antigens, which provided conventional ways for the production of antibodies specific for CL. More recently, others have directly attached an antimicrobial thirteen amino-acid peptide to CL to form conjugate (i.e., CL-$UBI_{29-41}$ hybrid), which were tested in mouse models (Chen et al., "Bacteria-Targeting Conjugates Based on Antimicrobial Peptide for Bacteria Diagnosis and Therapy," *Mol. Pharm.* 12(7):2505-2516 (2015)).

Despite these advances, there remains a need to identify other platforms for delivery of known antibiotics that overcomes current antibiotic resistance mechanisms. The present invention overcomes the deficiencies in the art and provides peptide-conjugated prodrugs derived from existing antibacterial agents, which overcome the above-noted deficiencies in the art.

SUMMARY

A first aspect of the present disclosure relates to a conjugated prodrug comprising a peptide conjugated to an antibiotic molecule via a cleavable linker. The peptide is preferably one that contains 2 to 6 amino acids, such as a dipeptide, tripeptide, tetrapeptide, pentapeptide, or hexapeptide.

A second aspect of the present disclosure relates to a pharmaceutical composition comprising a pharmaceutically acceptable carrier and the conjugated prodrug described herein.

A third aspect of the present disclosure relates to a method of enhancing the intracellular concentration of an antibiotic agent in a bacterium. This method involves contacting a bacterium with a conjugated prodrug according to the present disclosure, where the conjugated prodrug is taken up by the bacterium and the linker is cleaved intracellularly to release the antibiotic agent from the prodrug, causing an increase in the intracellular concentration of the antibiotic agent.

A fourth aspect of the present disclosure relates to a method of treating a patient for a bacterial infection. This method involves administering a conjugated prodrug or pharmaceutical composition according to the present disclosure to a patient in need of treatment.

The conjugated prodrugs, pharmaceutical compositions, and methods of use thereof described herein provide novel antimicrobial prodrugs with enhanced bacterial selectivity and, therefore, provide increased efficacy and decreased adverse effects as compared to currently available antimicrobial drugs.

The accompanying Examples demonstrate that conjugating various di-, tri-, and tetra-peptides to a prodrug of antibiotics (e.g., chloramphenicol and ciprofloxacin) drastically accelerates intrabacterial hydrolysis of ester bonds, regenerating the antibiotics against *E. coli* intracellulary. This was initially shown with the ester conjugate of chloramphenicol and diglycine (CLsuGG) and the ester conjugate of chloramphenicol and triglycine (CLsuGGG). Moreover, CLsuGG also exhibits reduced toxicity to bone marrow cells, a major side effect of CL (Yunis et al., "Reversible Bone Marrow Suppression from Chloramphenicol: A Consequence of Mitochondrial Injury," *Arch. Intern. Med.* 126(2):272-275 (1970), which is hereby incorporated by reference in its entirety). In addition, mechanistic investigation reveals that CLsuGG shows different hydrolysis rates upon being treated by the mammalian and bacterial esterases. To understand the structure-activity relationship of the peptide conjugated chloramphenicol for inhibiting bacteria, 34 additional structural analogs of CLsuGG were synthesized and their activities against *E. coli* were examined. The Examples described herein show that conjugating peptides to CLsu enhances the efficacy of prodrugs to varying degrees, apart from water-insoluble analogs. As shown in FIG. 1, negative charges, high steric hindrance in the side chains of peptides, or a rigid diester (i.e., cyclohexane-1,2-dicarboxylic acid) results in lower activities than that of CLsuGG. Moreover, the investigation of conjugated-peptides from single amino acid to pentapeptide indicates that dipeptides are the most effective to increase the efficacy of CLsu. In addition, capping the C-terminal of the peptide with an N-methyl group scarcely lowers the activity of the prodrug in comparison to the uncapped peptide conjugate. D-amino acid residues, in general, are more favorable than L-amino acid residues for increasing the activity of the prodrugs, suggesting that D-peptides affect little on the hydrolysis rate of the ester bond in the prodrugs. Besides establishing conjugation of peptides as a simple and effective way for modulating the properties of the prodrug chloramphenicol (CLsu), the structure-activity relationship of these peptides conjugated prodrugs may provide useful insight for designing peptide conjugates of other antibiotic agents.

BRIEF DESCRIPTION OF THE DRAWINGS

FIG. 3A is a graph showing the minimum inhibitory concentrations (MIC) of CL, CLsu, CLsuGG, CLsuG, and CLsuGGG against a wild type *E. coli* strain (K-12). FIG. 3B is a graph showing the antibacterial activity of CLsu and CLsuGG before and after the treatment of CES and *E. coli* (K-12) lysate. FIG. 3C is a graph showing the hydrolysis curve of CLsu and CLsuGG with the addition of exogenous carboxylesterase ("CES") or

*E. coli* (K-12) lysate; [CLsu]=[CLsuGG]=200 μM, [CES]=[*E. coli* lysate]=0.1 U/mL. FIG. 3D is a graph showing the static light scattering signals of the solution of CLsuGG before and after the addition of CES; [CLsuGG]=200 μM, [CES]=1 U/mL, t=24 hours. FIG. 3E shows the LC-MS results confirming that hydrolysis of CLsuGG regenerates CL. Inset (a) shows the LC-MS spectrum of *E. coli* lysate with the addition of CLsuGG at the concentration of 500 μM, which illustrates CLsuGG being completely degraded into chloroamphenicol (r.t.=1.66 minutes); and (b) shows the MS spectrum of *E. coli* lysate with the addition of CLsuGG, which illustrates the presence of chloroamphenicol (r.t.=1.66 minutes), which is at m/z 321.08 [M-H]. *E. coli* strains were harvested by centrifugation and the cell pellets were lysed using a sonic device. After centrifugation, CLsuGG was added to the cell extracts, which were then stored at 37° C. for 24 hours. To terminate the reactions, the solution was extracted with an equal volume of butanol and then concentrated to dryness before resuspending with butanol. FIG. 3F shows transmission electron microscopy (TEM) images of CLsuGG (500 μM and 100 μM) that shows few nanoparticles before the addition of CES, whereas many nanoparticles appear after the addition of CES (1 U/mL), scale bar=500 nm.

FIGS. 5A-5F demonstrate the antibacterial activity of CLsuGG against (FIG. 5A) single esterase (BioH, YjfP, FrsA, YbfF, YfbB, YqiA, YeiG, or and YpfH) deletion mutants and (FIG. 5B) a double esterase (BioH and YjfP) deletion mutant of *E. coli* (inset: magnified image in the dashed square). FIG. 5C is a 0.8% TAE agarose DNA gel electrophoresis image showing confirmation of double mutant *E. coli* with the deletion of BioH and YjfP. Two single colonies per mutant were picked randomly to do PCR. FIG. 5D is a graph showing the growth rate of single esterase (BioH, YjfP, FrsA, YbfF, YfbB, YqiA, YeiG, or YpfH) deletion mutants and a double esterase (BioH and YjfP) deletion mutant of *E. coli* confirming the overall fitness of the selected mutants.

FIG. 11A is a graph showing the antibacterial activity of 1c, 1d, 2b, and 2c before and after the treatment of porcine liver esterase ("PLE"); [PLE]=1 U/mL. FIG. 11B shows the hydrolysis curve of 1c, 1d, 2b, and 2c with the addition of the lysate of HepG2 cells or the lysate of *E. coli* (K-12); [1c]=[1d]=[2b]=[2c]=200 μM, [HepG2 lysate]=[*E. coli* lysate]=0.1 U/mL. FIG. 11C is a graph showing the static light scattering signals of the solution of 1c, 1d, 2b, and 2c before and after the addition of PLE; [1c]=[1d]=[2b]=[2c]=200 μM, [PLE]=1 U/mL, t=24h. FIG. 11D are TEM images of 1c, 1d, 2b, and 2c before and after the addition of PLE; [1c]=[1d]=[2b]=[2c]=500 [PLE]=1 U/mL, t=24 h, scale bar=500 nm.

FIGS. 14A-14B show the cell viability of HS-5 cells (FIG. 14A) and HEK293 cells (FIG. 14B) incubated with 1a, 1b, 1c, 1e, 1f, 1k, 1l, 1m, 1o, 1p, 2f, and 2j for 24 hours. [CL]=[CLsu]=[1a]=[1b]=[1c]=[1e]=[1f]=[1k]=[1l]=[1m]=[1o]=[1p]=[2f]=[2j]=20 μM; [Cipro]=[TMP]=[TEL]=0.5 μM. FIG. 14C shows the cell viability of HS-5 cells incubated with CL, CLsu, 1a, 1b, 1c, 1e, 1f, 1k, 1l, 1m, 1o, 1p, 2f, and 2j for 24 hours. [CL]=[CLsu]=[1a]=[1b]=[1c]=[1e]=[1f]=[1k]=[1l]=[1m]=[1o]=[1p]=[2f]=[2j]=200 μM; [Cipro]=[TMP]=[TEL]=5 μM. FIG. 14D shows the cell viability of HS-5 cells incubated with CL, CLsu, 1a, 1b, 1c, 1e, 1f, 1k, 1l, 1m, 1o, 1p, 2f, and 2j for 24 hours. [CL]=[CLsu]=[1a]=[1b]=[1c]=[1e]=[1f]=[1k]=[1l]=[1m]=[1o]=[1p]=[2f]=[2j]=2000 μM; [Cipro]=[TMP]=[TEL]=50 μM.

DETAILED DESCRIPTION

Figure 1:
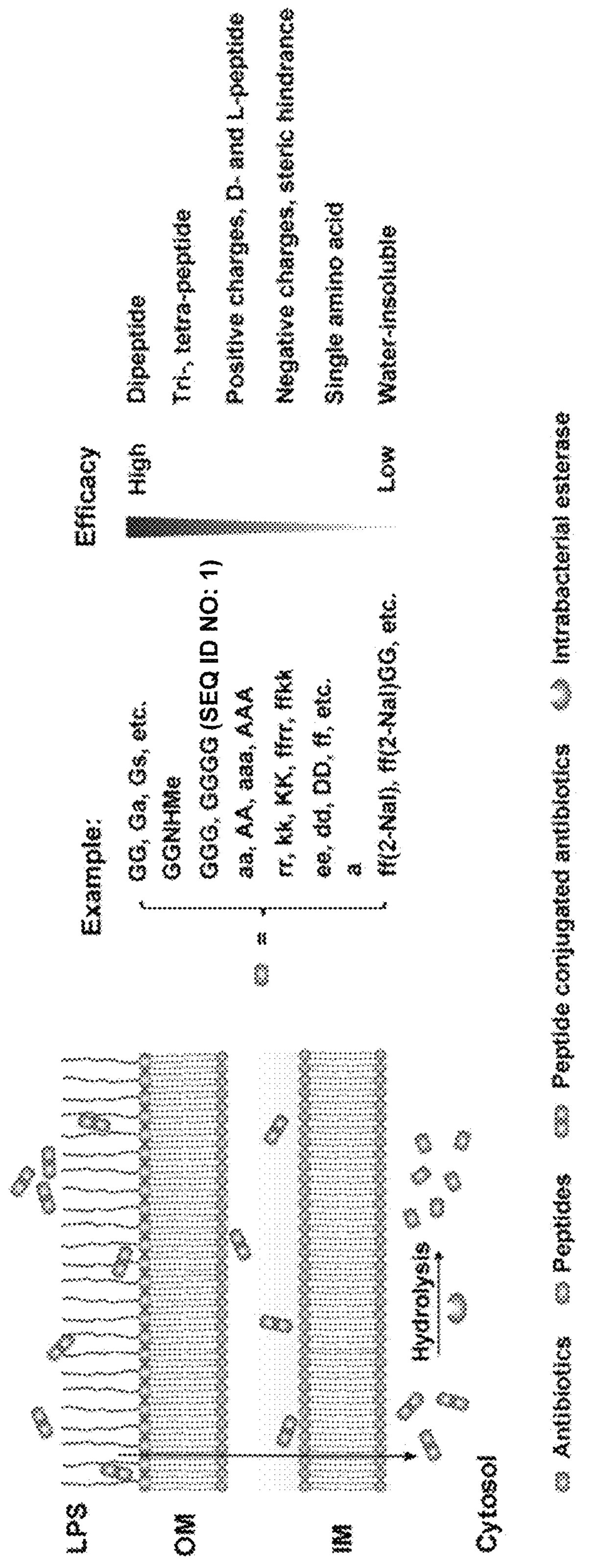
FIG. 1 is a schematic illustration of peptide conjugated antibiotics for intrabacterial activation and the trends of the efficiency associated with the structures of the conjugates (LPS: lipopolysaccharide; OM: outer membrane; IM: inner membrane).

A first aspect of the present disclosure relates to a conjugated prodrug comprising a peptide conjugated to an antibiotic molecule via a cleavable linker.

As used herein and in the appended claims, the singular "a", "an" and "the" include the plural reference unless the context clearly dictates otherwise. Thus, for example, reference to a "peptide" includes a plurality of such peptides.

As used herein the term "peptide" includes native peptides (either degradation products or synthetically synthesized peptides) and further to peptidomimetics, such as peptoids and semipeptoids which are peptide analogs, which may have, for example, modifications rendering the peptides more stable while in a body, having lower immunogenicity and/or higher affinity to their receptors.

In some embodiments, the peptide is an oligopeptide containing up to 6 amino acid residues. Thus, the peptide may be an oligopeptide containing 2, 3, 4, 5, or 6 amino acid residues. In certain embodiments, the peptide is a dipeptide. In other embodiments, the peptide is a tripeptide. In further embodiments, the peptide is a tetrapeptide or pentapeptide.

Naturally occurring amino acids are identified throughout by the conventional three-letter and/or one-letter abbreviations, corresponding to the trivial name of the amino acid, in accordance with the following list: Alanine (Ala), Arginine (Arg), Asparagine (Asn), Aspartic acid (Asp), Cysteine (Cys), Glutamic acid (Glu), Glutamine (Gln), Glycine (Gly), Histidine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr), and Valine (Val). The abbreviations are accepted in the peptide art and are recommended by the IUPAC-IUB commission in biochemical nomenclature.

The term "amino acid" further includes analogues, derivatives, and congeners of any specific amino acid referred to herein, as well as C-terminal or N-terminal protected amino acid derivatives (e.g., modified with an N-terminal or C-terminal protecting group). Furthermore, the term "amino acid" includes both D- and L-amino acids. Hence, an amino acid which is identified herein by its name, three letter or one letter symbol and is not identified specifically as having the D or L configuration, is understood to assume any one of the D or L configurations.

In certain embodiments, the peptide is non-antigenic, does not contain an enzymatically cleavable amino acid sequence, and does not contain an HIV Tat amino acid sequence.

In some embodiments of the disclosure, the peptide comprises L-amino acid residues. For example, the peptide may comprise only L-amino acids. Suitable peptides comprising L-amino acids include, without limitation, those selected from the group of L-Gly-L-Gly-L-Gly-L-Gly (SEQ ID NO: 1), L-Ala-L-Ala, L-Ala-L-Ala-L-Ala, L-Gly-L-Gly-L-Phe, L-Gly-L-Phe-L-Gly, L-Phe-L-Gly-L-Gly, L-Gly-L-Gly-L-Phe-L-Phe (SEQ ID NO: 3), L-Gly-L-Gly-L-Gly-L-Gly-L-Gly (SEQ ID NO: 5), L-Lys-L-Lys, L-Gly-L-Lys, L-Asp-L-Asp, L-Gly-L-Asp, L-Gly-L-Gly, L-Gly, L-Gly-L-Gly-NH—$CH_3$, and L-Gly-L-Gly-L-Gly. Of these exemplary peptides listed, those bearing a glycine residue at the first position are generally preferred.

In other embodiments of the disclosure, the peptide comprises D-amino acid residues. For example, the peptide may comprise only D-amino acids. Suitable peptides comprising D-amino acids include, without limitation, those selected from the group of D-Ala, D-Ala-D-Ala, D-Ala-D-Ala-D-Ala, D-Arg-D-Arg, D-Lys-D-Lys, D-Phe-D-Phe-D-Arg-D-Arg, D-Phe-D-Phe-D-Lys-D-Lys, D-Glu-D-Glu, D-Asp-D-Asp, D-Phe-D-Phe, and D-Glu-D-Pro. Of these exemplary peptides listed, those bearing a glycine residue at the first position are generally preferred.

In further embodiments of the disclosure, the peptide comprises a combination of L-amino acids and D-amino acids. Suitable peptides comprising a combination of D-amino acids and L-amino acids may be selected from the group consisting of L-Gly-D-Leu, L-Gly-D-Ala, L-Gly-D-Ser, D-Ser-L-Gly, L-Gly-L-Gly-D-Phe, and L-Gly-L-Gly-D-Phe-D-Phe. Of these exemplary peptides listed, those bearing a glycine residue at the first position are generally preferred.

As noted in FIG. 1, peptides that are generally preferred include those that are water-soluble, contain from two to six (such as from two to five, or from two to four) amino acids, where at least one or two of the amino acids are smaller neutral (e.g., glycine, alanine) or polar/uncharged hydrophilic (e.g., serine, threonine, tyrosine, asparagine, glutamine). Of these, peptides with glycine or alanine in the first position (covalently bound to the linker) are preferred. Hydrophilic positively charged (e.g., lysine, arginine, histidine) and negatively charged (aspartic acid and glutamic acid) amino acids are tolerated, although positively charged amino acids are preferred. Hydrophobic amino acids (e.g., valine, leucine, isoleucine, methionine, phenylalanine, naphthylalanine, tryptophan, proline, cysteine) are also tolerated, although those having bulky sidechains are generally less preferred.

In some embodiments, the peptide comprises at least one hydrophobic amino acid residue.

In other embodiments, the peptide comprises at least one hydrophilic amino acid residue.

In certain embodiments, it is desirable that the peptide contains neutral or polar amino acids with smaller sidechains that minimize steric hindrance including Gly, Ala, Val, Ile, Leu, Ser, Thr, Asn, Met, and Gln; and/or amino acids that are positively charged including Arg and Lys. In certain embodiments, the peptide is free of negatively charged amino acid residues (Asp and Glu), free of amino acids that may cause instability (Cys), and/or free of amino acids with bulky sidechains (His, Pro, Phe, Tyr, and Trp).

In some embodiments, the peptide comprises a capping moiety. In accordance with such embodiments, the capping moiety can be an N-methyl group (—NH—$CH_3$), a taurine residue (—NH—$CH_2$—$CH_2$—$HSO_3$), or an o-phosphorylethanolamine residue (—NH—$CH_2$—$CH_2$—O—$H_2PO_3$).

As described herein, bacteria possess two major categories of peptide transporters for importing peptides as nutrients—proton-dependent oligopeptide transporters (POT transporters; also known as peptide transporters (PTR) transporters) and ATP-binding cassette transporters (ABC transporters). Peptide transporters are located in the plasma membrane of Gram positive bacteria and inner membrane of Gram negative bacteria and function to acquire specific peptides from the periplasm (Garai et al., "Bacterial Peptide Transporters: Messengers of Nutrition to Virulence," *Virulence* 8(3):297-309 (2017), which is hereby incorporated by reference in its entirety).

PTR transporters are monomeric proteins that mediate the cellular uptake of di- and tri-peptides and a variety of peptidomimetics in animals, plants, yeast, and both Gram-negative and Gram-positive bacteria (Weitz et al., "Functional and Structural Characterization of a Prokaryotic Peptide Transporter with Features Similar to Mammalian PEPT1," *J. Biol. Chem* 282(5):2832-2839 (2007), which is hereby incorporated by reference in its entirety). For example, in *Escherichia coli*, the PTR transporter YdgR selectively transports dipeptides, tripeptides, and related peptidomimetics (such as β-lactam antibiotics).

PTR transporters typically contain 12-18 transmembrane domains which derive their energy of transport from the import of protons. Various PTR peptide transporters are well known in the art and include, e.g., the *Salmonella typhimurium* PRT transporters Tpp, CstA, and YjiY; *Staphylococcus aureus* PRT transporter DtpT; and the *Escherichia coli* PRT transporters YdgR, YhiP, and YjdL (Garai et al., "Bacterial Peptide Transporters: Messengers of Nutrition to Virulence," *Virulence* 8(3):297-309 (2017), which is hereby incorporated by reference in its entirety).

ABC transporters are multi-subunit protein pumps that couple ATP hydrolysis with the movement of dipeptides, tripeptides, and oligopeptides across the inner membrane in, e.g., animals, plants, yeast, and bacteria (Garai et al., "Bacterial Peptide Transporters: Messengers of Nutrition to Virulence," Virulence 8(3):297-309 (2017), which is hereby incorporated by reference in its entirety). In Gram-negative bacteria, the substrate peptides are usually accessible through an extracytoplasmic receptor, called solute-binding protein (SBP), whereas Gram-positive bacteria contain a lipoprotein subunit that extends beyond the extracellular face of the cell membrane. Various PTR peptide transporters are well known in the art and include, e.g., proteins encoded by the Opp operon in *Salmonella* sp, *Mycobacterium tuberculosis, Staphylococcus aureus, Corynebacterium pseudotuberculosis, Clostridium difficile, Listeria monocytogenes, Campylobacter jejuni, Moraxella catarhhalis*, and *Borrelia burgdorferi*; proteins encoded by the Dpp operon in *Salmonella typhimurium* and *Streptococcus pyogenes*; proteins encoded by the Ami operon in *Streptococcus pneumoniae*; proteins encoded by the App operon in *Clostridium difficile*; proteins encoded by the Yej operon in *Salmonella Typhimurium*; proteins encoded by the Sap operon in *Salmonella typhimurium*; and HppA in *Streptococcus gordonii* (Garai et al., "Bacterial Peptide Transporters: Messengers of Nutrition to Virulence," *Virulence* 8(3):297-309 (2017), which is hereby incorporated by reference in its entirety).

Applicants have unexpectedly found that conjugation of antibiotic molecules to a peptide via a cleavable linker increases the uptake and retention of the antibiotic molecules inside bacteria expressing peptide transporters (e.g., Gram-negative bacteria). Such conjugated prodrug compounds provide an effective strategy for enhancing the efficacy of known antibiotic molecules in bacteria.

In some embodiments, the peptide is transportable via a bacterial PTR peptide transporter. Suitable bacterial PTR peptide transporters are well known in the and described in more detail above. In certain embodiments, the bacterial PTR peptide transporter is selected from the group consisting of YdgR, YhiP, YjdL, Tpp, CstA, YjiY, or DtpT. In accordance with these embodiments, the conjugated prodrug comprises a dipeptide or tripeptide.

In some embodiments, the peptide is transportable via a bacterial ABC peptide transporter. Suitable bacterial ABC peptide transporters are well known in the art and described in more detail above. In certain embodiments, the bacterial ABC peptide transporter is selected from the group consisting of Opp, Dpp, Ami, App, Yej, Sap, and HppA.

As described herein above, suitable substrates for bacterial peptide transporters and bacterial ABC transporters include dipeptides and tripeptides. Thus, in certain embodiments, when the peptide is a dipeptide comprising only neutral/uncharged amino acid residues, the dipeptide may be selected from the group consisting of Gly-Gly, Gly-Ala, Gly-Val, Gly-Leu, Gly-Ile, Gly-Pro, Gly-Phe, Gly-Met, Gly-Trp, Ala-Gly, Ala-Ala, Ala-Val, Ala-Leu, Ala-Ile, Ala-Pro, Ala-Phe, Ala-Met, Ala-Trp, Val-Gly, Val-Ala, Val-Val, Val-Leu, Val-Ile, Val-Pro, Val-Phe, Val-Met, Val-Trp, Leu-Gly, Leu-Ala, Leu-Val, Leu-Leu, Leu-Ile, Leu-Pro, Leu-Phe, Leu-Met, Leu-Trp, Ile-Gly, Ile-Ala, Ile-Val, Ile-Leu, Ile-Ile, Ile-Pro, Ile-Phe, Ile-Met, Ile-Trp, Pro-Gly, Pro-Ala, Pro-Val, Pro-Leu, Pro-Ile, Pro-Pro, Pro-Phe, Pro-Met, Pro-Trp, Phe-Gly, Phe-Ala, Phe-Val, Phe-Leu, Phe-Ile, Phe-Pro, Phe-Phe, Phe-Met, Phe-Trp, Met-Gly, Met-Ala, Met-Val, Met-Leu, Met-Ile, Met-Pro, Met-Phe, Met-Met, Met-Trp, Trp-Gly, Trp-Ala, Trp-Val, Trp-Leu, Trp-Ile, Trp-Pro, Trp-Phe, Trp-Met, and Trp-Trp.

In certain embodiments, when the peptide is a tripeptide comprising only neutral/uncharged amino acid residues, the tripeptide may be selected from the group consisting of Gly-Gly-Gly, Gly-Gly-Ala, Gly-Gly-Val, Gly-Gly-Leu, Gly-Gly-Ile, Gly-Gly-Pro, Gly-Gly-Phe, Gly-Gly-Met, Gly-Gly-Trp, Gly-Ala-Gly, Gly-Ala-Ala, Gly-Ala-Val, Gly-Ala-Leu, Gly-Ala-Ile, Gly-Ala-Pro, Gly-Ala-Phe, Gly-Ala-Met, Gly-Ala-Trp, Gly-Val-Gly, Gly-Val-Ala, Gly-Val-Val, Gly-Val-Leu, Gly-Val-Ile, Gly-Val-Pro, Gly-Val-Phe, Gly-Val-Met, Gly-Val-Trp, Gly-Leu-Gly, Gly-Leu-Ala, Gly-Leu-Val, Gly-Leu-Leu, Gly-Leu-Ile, Gly-Leu-Pro, Gly-Leu-Phe, Gly-Leu-Met, Gly-Leu-Trp, Gly-Ile-Gly, Gly-Ile-Ala, Gly-Ile-Val, Gly-Ile-Leu, Gly-Ile-Ile, Gly-Ile-Pro, Gly-Ile-Phe, Gly-Ile-Met, Gly-Ile-Trp, Gly-Pro-Gly, Gly-Pro-Ala, Gly-Pro-Val, Gly-Pro-Leu, Gly-Pro-Ile, Gly-Pro-Pro, Gly-Pro-Phe, Gly-Pro-Met, Gly-Pro-Trp, Gly-Phe-Gly, Gly-Phe-Ala, Gly-Phe-Val, Gly-Phe-Leu, Gly-Phe-Ile, Gly-Phe-Pro, Gly-Phe-Phe, Gly-Phe-Met, Gly-Phe-Trp, Gly-Met-Gly, Gly-Met-Ala, Gly-Met-Val, Gly-Met-Leu, Gly-Met-Ile, Gly-Met-Pro, Gly-Met-Phe, Gly-Met-Met, Gly-Met-Trp, Gly-Trp-Gly, Gly-Trp-Ala, Gly-Trp-Val, Gly-Trp-Leu, Gly-Trp-Ile, Gly-Trp-Pro, Gly-Trp-Phe, Gly-Trp-Met, Gly-Trp-Trp, Ala-Gly-Gly, Ala-Gly-Ala, Ala-Gly-Val, Ala-Gly-Leu, Ala-Gly-Ile, Ala-Gly-Pro, Ala-Gly-Phe, Ala-Gly-Met, Ala-Gly-Trp, Ala-Ala-Gly, Ala-Ala-Ala, Ala-Ala-Val, Ala-Ala-Leu, Ala-Ala-Ile, Ala-Ala-Pro, Ala-Ala-Phe, Ala-Ala-Met, Ala-Ala-Trp, Ala-Val-Gly, Ala-Val-Ala, Ala-Val-Val, Ala-Val-Leu, Ala-Val-Ile, Ala-Val-Pro, Ala-Val-Phe, Ala-Val-Met, Ala-Val-Trp, Ala-Leu-Gly, Ala-Leu-Ala, Ala-Leu-Val, Ala-Leu-Leu, Ala-Leu-Ile, Ala-Leu-Pro, Ala-Leu-Phe, Ala-Leu-Met, Ala-Leu-Trp, Ala-Ile-Gly, Ala-Ile-Ala, Ala-Ile-Val, Ala-Ile-Leu, Ala-Ile-Ile, Ala-Ile-Pro, Ala-Ile-Phe, Ala-Ile-Met, Ala-Ile-Trp, Ala-Pro-Gly, Ala-Pro-Ala, Ala-Pro-Val, Ala-Pro-Leu, Ala-Pro-Ile, Ala-Pro-Pro, Ala-Pro-Phe, Ala-Pro-Met, Ala-Pro-Trp, Ala-Phe-Gly, Ala-Phe-Ala, Ala-Phe-Val, Ala-Phe-Leu, Ala-Phe-Ile, Ala-Phe-Pro, Ala-Phe-Phe, Ala-Phe-Met, Ala-Phe-Trp, Ala-Met-Gly, Ala-Met-Ala, Ala-Met-Val, Ala-Met-Leu, Ala-Met-Ile, Ala-Met-Pro, Ala-Met-Phe, Ala-Met-Met, Ala-Met-Trp, Ala-Trp-Gly, Ala-Trp-Ala, Ala-Trp-Val, Ala-Trp-Leu, Ala-Trp-Ile, Ala-Trp-Pro, Ala-Trp-Phe, Ala-Trp-Met, Ala-Trp-Trp, Val-Gly-Gly, Val-Gly-Ala, Val-Gly-Val, Val-Gly-Leu, Val-Gly-Ile, Val-Gly-Pro, Val-Gly-Phe, Val-Gly-Met, Val-Gly-Trp, Val-Ala-Gly, Val-Ala-Ala, Val-Ala-Val, Val-Ala-Leu, Val-Ala-Ile, Val-Ala-Pro, Val-Ala-Phe, Val-Ala-Met, Val-Ala-Trp, Val-Val-Gly, Val-Val-Ala, Val-Val-Val, Val-Val-Leu, Val-Val-Ile, Val-Val-Pro, Val-Val-Phe, Val-Val-Met, Val-Val-Trp, Val-Leu-Gly, Val-Leu-Ala, Val-Leu-Val, Val-Leu-Leu, Val-Leu-Ile, Val-Leu-Pro, Val-Leu-Phe, Val-Leu-Met, Val-Leu-Trp, Val-Ile-Gly, Val-Ile-Ala, Val-Ile-Val, Val-Ile-Leu, Val-Ile-Ile, Val-Ile-Pro, Val-Ile-Phe, Val-Ile-Met, Val-Ile-Trp, Val-Pro-Gly, Val-Pro-Ala, Val-Pro-Val, Val-Pro-Leu, Val-Pro-Ile, Val-Pro-Pro, Val-Pro-Phe, Val-Pro-Met, Val-Pro-Trp, Val-Phe-Gly, Val-Phe-Ala, Val-Phe-Val, Val-Phe-Leu, Val-Phe-Ile, Val-Phe-Pro, Val-Phe-Phe, Val-Phe-Met, Val-Phe-Trp, Val-Met-Gly, Val-Met-Ala, Val-Met-Val, Val-Met-Leu, Val-Met-Ile, Val-Met-Pro, Val-Met-Phe, Val-Met-Met, Val-Met-Trp, Val-Trp-Gly, Val-Trp-Ala, Val-Trp-Val, Val-Trp-Leu, Val-Trp-Ile, Val-Trp-Pro, Val-Trp-Phe, Val-Trp-Met, Val-Trp-Trp, Leu-Gly-Gly, Leu-Gly-Ala, Leu-Gly-Val, Leu-Gly-Leu, Leu-Gly-Ile, Leu-Gly-Pro, Leu-Gly-Phe, Leu-Gly-Met, Leu-Gly-Trp, Leu-Ala-Gly, Leu-Ala-Ala, Leu-Ala-Val, Leu-Ala-Leu, Leu-Ala-Ile, Leu-Ala-Pro, Leu-Ala-Phe, Leu-Ala-Met, Leu-Ala-Trp, Leu-Val-Gly, Leu-Val-Ala, Leu-Val-Val, Leu-Val-Leu, Leu-Val-Ile, Leu-Val-Pro, Leu-Val-Phe, Leu-Val-Met, Leu-Val-Trp, Leu-Leu-Gly, Leu-Leu-Ala, Leu-Leu-Val, Leu-Leu-Leu, Leu-Leu-Ile, Leu-Leu-Pro, Leu-Leu-Phe, Leu-Leu-Met, Leu-Leu-Trp, Leu-Ile-Gly, Leu-Ile-Ala, Leu-Ile-Val, Leu-Ile-Leu, Leu-Ile-Ile, Leu-Ile-Pro, Leu-Ile-Phe, Leu-Ile-Met, Leu-Ile-Trp, Leu-Pro-Gly, Leu-Pro-Ala, Leu-Pro-Val, Leu-Pro-Leu, Leu-Pro-Ile, Leu-Pro-Pro, Leu-Pro-Phe, Leu-Pro-Met, Leu-Pro-Trp, Leu-Phe-Gly, Leu-Phe-Ala, Leu-Phe-Val, Leu-Phe-Leu, Leu-Phe-Ile, Leu-Phe-Pro, Leu-Phe-Phe, Leu-Phe-Met, Leu-Phe-Trp, Leu-Met-Gly, Leu-Met-Ala, Leu-Met-Val, Leu-Met-Leu, Leu-Met-Ile, Leu-Met-Pro, Leu-Met-Phe, Leu-Met-Met, Leu-Met-Trp, Leu-Trp-Gly, Leu-Trp-Ala, Leu-Trp-Val, Leu-Trp-Leu, Leu-Trp-Ile, Leu-Trp-Pro, Leu-Trp-Phe, Leu-Trp-Met, Leu-Trp-Trp, Ile-Gly-Gly, Ile-Gly-Ala, Ile-Gly-Val, Ile-Gly-Leu, Ile-Gly-Ile, Ile-Gly-Pro, Ile-Gly-Phe, Ile-Gly-Met, Ile-Gly-Trp, Ile-Ala-Gly, Ile-Ala-Ala, Ile-Ala-Val, Ile-Ala-Leu, Ile-Ala-Ile, Ile-Ala-Pro, Ile-Ala-Phe, Ile-Ala-Met, Ile-Ala-Trp, Ile-Val-Gly, Ile-Val-Ala, Ile-Val-Val, Ile-Val-Leu, Ile-Val-Ile, Ile-Val-Pro, Ile-Val-Phe, Ile-Val-Met, Ile-Val-Trp, Ile-Leu-Gly, Ile-Leu-Ala, Ile-Leu-Val, Ile-Leu-Leu, Ile-Leu-Ile, Ile-Leu-Pro, Ile-Leu-Phe, Ile-Leu-Met, Ile-Leu-Trp, Ile-Ile-Gly, Ile-Ile-Ala, Ile-Ile-Val, Ile-Ile-Leu, Ile-Ile-Ile, Ile-Ile-Pro, Ile-Ile-Phe, Ile-Ile-Met, Ile-Ile-Trp, Ile-Pro-Gly, Ile-Pro-Ala, Ile-Pro-Val, Ile-Pro-Leu, Ile-Pro-Ile, Ile-Pro-Pro, Ile-Pro-Phe, Ile-Pro-Met, Ile-Pro-Trp, Ile-Phe-Gly, Ile-Phe-Ala, Ile-Phe-Val, Ile-Phe-Leu, Ile-Phe-Ile, Ile-Phe-Pro, Ile-Phe-Phe, Ile-Phe-Met, Ile-Phe-Trp, Ile-Met-Gly, Ile-Met-Ala, Ile-Met-Val, Ile-Met-Leu, Ile-Met-Ile, Ile-Met-Pro, Ile-Met-Phe, Ile-Met-Met, Ile-Met-Trp, Ile-Trp-Gly, Ile-Trp-Ala, Ile-Trp-Val, Ile-Trp-Leu, Ile-Trp-Ile, Ile-Trp-Pro, Ile-Trp-Phe, Ile-Trp-Met, Ile-Trp-Trp, Pro-Gly-Gly, Pro-Gly-Ala, Pro-Gly-Val, Pro-Gly-Leu, Pro-Gly-Ile, Pro-Gly-Pro, Pro-Gly-Phe, Pro-Gly-Met, Pro-Gly-Trp, Pro-Ala-Gly, Pro-Ala-Ala, Pro-Ala-Val, Pro-Ala-Leu, Pro-Ala-Ile, Pro-Ala-Pro, Pro-Ala-Phe, Pro-Ala-Met, Pro-Ala-Trp, Pro-Val-Gly, Pro-Val-Ala, Pro-Val-Val, Pro-Val-Leu, Pro-Val-Ile, Pro-Val-Pro, Pro-Val-Phe, Pro-Val-Met, Pro-Val-Trp, Pro-Leu-Gly, Pro-Leu-Ala, Pro-Leu-Val, Pro-Leu-Leu, Pro-Leu-Ile, Pro-Leu-Pro, Pro-Leu-Phe, Pro-Leu-Met, Pro-Leu-Trp, Pro-Ile-Gly, Pro-Ile-Ala, Pro-Ile-Val, Pro-Ile-Leu, Pro-Ile-Ile, Pro-Ile-Pro, Pro-Ile-Phe, Pro-Ile-Met, Pro-Ile-Trp, Pro-Pro-Gly, Pro-Pro-Ala, Pro-Pro-Val, Pro-Pro-Leu, Pro-Pro-Ile, Pro-Pro-Pro, Pro-Pro-Phe, Pro-Pro-Met, Pro-Pro-Trp, Pro-Phe-Gly, Pro-Phe-Ala, Pro-Phe-Val, Pro-Phe-Leu, Pro-Phe-Ile, Pro-Phe-Pro, Pro-Phe-Phe, Pro-Phe-Met, Pro-Phe-Trp, Pro-Met-Gly, Pro-Met-Ala, Pro-Met-Val, Pro-Met-Leu, Pro-Met-Ile, Pro-Met-Pro, Pro-Met-Phe, Pro-Met-Met, Pro-Met-Trp, Pro-Trp-Gly, Pro-Trp-Ala, Pro-Trp-Val, Pro-Trp-Leu, Pro-Trp-Ile, Pro-Trp-Pro, Pro-Trp-Phe, Pro-Trp-Met, Pro-Trp-Trp, Phe-Gly-Gly, Phe-Gly-Ala, Phe-Gly-Val, Phe-Gly-Leu, Phe-Gly-Ile, Phe-Gly-Pro, Phe-Gly-Phe, Phe-Gly-Met, Phe-Gly-Trp, Phe-Ala-Gly, Phe-Ala-Ala, Phe-Ala-Val, Phe-Ala-Leu, Phe-Ala-Ile, Phe-Ala-Pro, Phe-Ala-Phe, Phe-Ala-Met, Phe-Ala-Trp, Phe-Val-Gly, Phe-Val-Ala, Phe-Val-Val, Phe-Val-Leu, Phe-Val-Ile, Phe-Val-Pro, Phe-Val-Phe, Phe-Val-Met, Phe-Val-Trp, Phe-Leu-Gly, Phe-Leu-Ala, Phe-Leu-Val, Phe-Leu-Leu, Phe-Leu-Ile, Phe-Leu-Pro, Phe-Leu-Phe, Phe-Leu-Met, Phe-Leu-Trp, Phe-Ile-Gly, Phe-Ile-Ala, Phe-Ile-Val, Phe-Ile-Leu, Phe-Ile-Ile, Phe-Ile-Pro, Phe-Ile-Phe, Phe-Ile-Met, Phe-Ile-Trp, Phe-Pro-Gly, Phe-Pro-Ala, Phe-Pro-Val, Phe-Pro-Leu, Phe-Pro-Ile, Phe-Pro-Pro, Phe-Pro-Phe, Phe-Pro-Met, Phe-Pro-Trp, Phe-Phe-Gly, Phe-Phe-Ala, Phe-Phe-Val, Phe-Phe-Leu, Phe-Phe-Ile, Phe-Phe-Pro, Phe-Phe-Phe, Phe-Phe-Met, Phe-Phe-Trp, Phe-Met-Gly, Phe-Met-Ala, Phe-Met-Val, Phe-Met-Leu, Phe-Met-Ile, Phe-Met-Pro, Phe-Met-Phe, Phe-Met-Met, Phe-Met-Trp, Phe-Trp-Gly, Phe-Trp-Ala, Phe-Trp-Val, Phe-Trp-Leu, Phe-Trp-Ile, Phe-Trp-Pro, Phe-Trp-Phe, Phe-Trp-Met, Phe-Trp-Trp, Met-Gly-Gly, Met-Gly-Ala, Met-Gly-Val, Met-Gly-Leu, Met-Gly-Ile, Met-Gly-Pro, Met-Gly-Phe, Met-Gly-Met, Met-Gly-Trp, Met-Ala-Gly, Met-Ala-Ala, Met-Ala-Val, Met-Ala-Leu, Met-Ala-Ile, Met-Ala-Pro, Met-Ala-Phe, Met-Ala-Met, Met-Ala-Trp, Met-Val-Gly, Met-Val-Ala, Met-Val-Val, Met-Val-Leu, Met-Val-Ile, Met-Val-Pro, Met-Val-Phe, Met-Val-Met, Met-Val-Trp, Met-Leu-Gly, Met-Leu-Ala, Met-Leu-Val, Met-Leu-Leu, Met-Leu-Ile, Met-Leu-Pro, Met-Leu-Phe, Met-Leu-Met, Met-Leu-Trp, Met-Ile-Gly, Met-Ile-Ala, Met-Ile-Val, Met-Ile-Leu, Met-Ile-Ile, Met-Ile-Pro, Met-Ile-Phe, Met-Ile-Met, Met-Ile-Trp, Met-Pro-Gly, Met-Pro-Ala, Met-Pro-Val, Met-Pro-Leu, Met-Pro-Ile, Met-Pro-Pro, Met-Pro-Phe, Met-Pro-Met, Met-Pro-Trp, Met-Phe-Gly, Met-Phe-Ala, Met-Phe-Val, Met-Phe-Leu, Met-Phe-Ile, Met-Phe-Pro, Met-Phe-Phe, Met-Phe-Met, Met-Phe-Trp, Met-Met-Gly, Met-Met-Ala, Met-Met-Val, Met-Met-Leu, Met-Met-Ile, Met-Met-Pro, Met-Met-Phe, Met-Met-Met, Met-Met-Trp, Met-Trp-Gly, Met-Trp-Ala, Met-Trp-Val, Met-Trp-Leu, Met-Trp-Ile, Met-Trp-Pro, Met-Trp-Phe, Met-Trp-Met, Met-Trp-Trp, Trp-Gly-Gly, Trp-Gly-Ala, Trp-Gly-Val, Trp-Gly-Leu, Trp-Gly-Ile, Trp-Gly-Pro, Trp-Gly-Phe, Trp-Gly-Met, Trp-Gly-Trp, Trp-Ala-Gly, Trp-Ala-Ala, Trp-Ala-Val, Trp-Ala-Leu, Trp-Ala-Ile, Trp-Ala-Pro, Trp-Ala-Phe, Trp-Ala-Met, Trp-Ala-Trp, Trp-Val-Gly, Trp-Val-Ala, Trp-Val-Val, Trp-Val-Leu, Trp-Val-Ile, Trp-Val-Pro, Trp-Val-Phe, Trp-Val-Met, Trp-Val-Trp, Trp-Leu-Gly, Trp-Leu-Ala, Trp-Leu-Val, Trp-Leu-Leu, Trp-Leu-Ile, Trp-Leu-Pro, Trp-Leu-Phe, Trp-Leu-Met, Trp-Leu-Trp, Trp-Ile-Gly, Trp-Ile-Ala, Trp-Ile-Val, Trp-Ile-Leu, Trp-Ile-Ile, Trp-Ile-Pro, Trp-Ile-Phe, Trp-Ile-Met, Trp-Ile-Trp, Trp-Pro-Gly, Trp-Pro-Ala, Trp-Pro-Val, Trp-Pro-Leu, Trp-Pro-Ile, Trp-Pro-Pro, Trp-Pro-Phe, Trp-Pro-Met, Trp-Pro-Trp, Trp-Phe-Gly, Trp-Phe-Ala, Trp-Phe-Val, Trp-Phe-Leu, Trp-Phe-Ile, Trp-Phe-Pro, Trp-Phe-Phe, Trp-Phe-Met, Trp-Phe-Trp, Trp-Met-Gly, Trp-Met-Ala, Trp-Met-Val, Trp-Met-Leu, Trp-Met-Ile, Trp-Met-Pro, Trp-Met-Phe, Trp-Met-Met, Trp-Met-Trp, Trp-Trp-Gly, Trp-Trp-Ala, Trp-Trp-Val, Trp-Trp-Leu, Trp-Trp-Ile, Trp-Trp-Pro, Trp-Trp-Phe, Trp-Trp-Met, and Trp-Trp-Trp.

In some embodiments, the peptide is a dipeptide comprising at least one glycine residue. Suitable dipeptides include, without limitation, Gly-Ala, Gly-Arg, Gly-Asn, Gly-Asp, Gly-Cys, Gly-Glu, Gly-Gln, Gly-Gly, Gly-Ile, Gly-Leu, Gly-Lys, Gly-Met, Gly-Phe, Gly-Pro, Gly-Ser, Gly-Thr, Gly-Trp, Gly-Tyr, Gly-Val, and Gly-Nal. For example, the dipeptide may be selected from the group consisting of D-Gly-D-Ala, D-Gly-D-Arg, D-Gly-D-Asn, D-Gly-D-Asp, D-Gly-D-Cys, D-Gly-D-Glu, D-Gly-D-Gln, D-Gly-D-Gly, D-Gly-D-Ile, D-Gly-D-Leu, D-Gly-D-Lys, D-Gly-D-Met, D-Gly-D-Phe, D-Gly-D-Pro, D-Gly-D-Ser, D-Gly-D-Thr, D-Gly-D-Trp, D-Gly-D-Tyr, D-Gly-D-Val, and D-Gly-D-Nal.

Also contemplated are tetrapeptides, pentapeptides, and hexapeptides that comprises one or more of the above-noted dipeptides and/or tripeptides, optionally with one or more non-hydrophobic amino acids. For example, and without limitation, the pentapeptide Gly-Gly-Glu-Gly-Gly (SEQ ID NO: 6) contains two copies of Gly-Gly separated by a hydrophilic Glu residue. Alternatively, the tetrapeptide Gly-Gly-Gly-Gly (SEQ ID NO: 1) contains no hydrophilic residues.

As described above, the conjugated prodrug comprises a linker. The linker may be attached to the peptide at the carboxy-terminus or the amino-terminus. In some embodiments, the linker is attached to the peptide carboxy terminus via peptide bond.

Suitable antibiotic molecules may be selected from the group consisting of, e.g., aminoglycosides, aminocoumarins, β-lactams, macrolides, ketolides, lincosamides, streptogramins, quinolones, rifamycins, tetracyclines, oxazolidinones, glycylcycline, amphenicals, and polymyxins. Exemplary antibiotic molecules are listed in Table 1 below.

TABLE 1

Suitable Antibiotic Molecules

| Antibiotic Class | Exemplary Compounds |
| --- | --- |
| Aminoglycosides | amikacin, arbekacin, butirosin, dibekacin, fortimicins, gentamicin, kanamycin, meomycin, neomycin, netilmicin, ribostamycin, sisomicin, spectinomycin, streptomycin, tobramycin, verdamicin, astromicin |
| Aminocoumarins | novobiocin, coumermycin, clorobiocin |
| Beta-lactams | imipenem, meropenem, biapenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefmetazole, cefoxitin, cefotetan, azthreonam, carumonam, flomoxef, moxalactam, amidinocillin, amoxicillin, ampicillin, azlocillin, carbenicillin, carbapenem, benzylpenicillin, carfecillin, cloxacillin, dicloxacillin, methicillin, mezlocillin, nafcillin, oxacillin, benzylpenicillin (penicillin G), penicillin V, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, LY206763 |
| Macrolides | azithromycin, clarithromycin, erythromycin, oleandomycin, rokitamycin, rosaramicin, roxithromycin, troleandomycin |
| Ketolides | telithromycin, cethromycin, solithromycin |
| Lincosamides | clindamycin, lincomycin, pirlimycin |
| Streptogramins | Pristinamycin, quinupristin/dalfopristin, virginiamycin |
| Quinolones/ Fluoroquinones | amifloxacin, cinoxacin, ciprofloxacin, N-(2-hydroxyacetyl)-ciprofloxacin, enoxacin, fleroxacin, flumequine, lomefloxacin, nalidixic acid, norfloxacin, ofloxacin, levofloxacin, lomefloxacin, oxolinic acid, pefloxacin, rosoxacin, temafloxacin, tosufloxacin, sparfloxacin, clinafloxacin, gatifloxacin, moxifloxacin, gemifloxacin, garenoxacin |
| Rifamycins | rifampin, rifabutin, rifapentine, rifalazil, rifaximin |
| Tetracyclines | doxycycline, chlortetracycline, clomocycline, demeclocycline, lymecycline, meclocycline, metacycline, minocycline, omadacycline, oxytetracycline, penimepicycline, rolitetracycline, sarecycline, tetracycline |
| Oxazolidinones | linezolid, posizolid, tedizolid, radezolid, cycloserine, (S)-5-((isoxazol-3-ylamino)methyl)-3-(2,3,5-trifluoro-4-(4-oxo-3,4-dihydropyridin-1(2H)-yl)phenyl)oxazolidin-2-one (MRX-I) |
| Glycylcyclines | tigecycline |
| Amphenicols | chloramphenicol, azidamfenicol, thiamphenicol, florfenicol |
| Polymyxins | polymyxin B, polymyxin E |

In some embodiments, the antibiotic molecule is a fluoroquinone, beta-lactam, aminocoumarin, carbapenem, or polymyxin.

In some embodiments, the antibiotic molecule is selected from the group consisting of chloramphenicol, N-(2-hydroxyacetyl)-ciprofloxacin, novobiocin, and benzylpenicillin (penicillin G).

As described herein, bacterial efflux pumps contribute to multidrug resistance by expelling antibiotic molecules from the cell. Exemplary bacterial efflux pump transporters include: small multidrug resistance (SMR) transporters, major facilitator superfamily (MFS) transporters, resistance nodulation cell division (RND) transporters, multidrug and toxic compound extrusion (MATE) transporters, and ATP-binding cassette (ABC) transporters. As an energy source, ABC transporters utilize ATP to drive toxins from the cell; MFS, RND, and SMR transporters employ the proton-motive force; and the MATE transporters are characterized by either Natsubtrate or $H^+$-substrate antiport (Askoura et al., "Efflux Pump Inhibitors (EPIs) as New Antimicrobial Agents Against *Pseudomonas aeruginosa,*" *Libyan J. Med.* 10.3402 (2011) and Delmar et al., Bacterial Multi-Drug Efflux Transporters," *Annu. Rev. Biophys.* 43:93-117 (2014), which are hereby incorporated by reference in their entirety). Suitable substrates for bacterial efflux pump inhibitors are identified in Table 2 below.

TABLE 2

| Exemplary Bacterial Efflux Pumps and Their Substrates | | |
|---|---|---|
| Bacterial Efflux Pump | Energy Source | Exemplary Substrates* |
| major facilitator superfamily (MFS) | Proton motive force | norfloxacin, enoxacin, ofloxacin, ciprofloxacin, pentamidine isethionate, cetrimide, benzalkonium chloride, acriflavine, sparfloxacin, gemifloxacin, premafloxacin cetrimide, virginiamycin, novobiocin, mupirocin, fusidic acid, doxorubicin, daunorubicin, linezolid, chloramphenicol, florfenicol, erythromycin, kanamycin |
| resistance nodulation cell division (RND) | Proton motive force | aminoglycosides, β-lactams, fluoroquinolones, tetracyclines, tigecycline, macrolides, chloramphenicol, trimethoprim |
| small multidrug resistance (SMR) | Proton motive force | Erythromycin, novobiocin, aminoglycosides, quinolones, tetracycline, trimethoprim |
| multidrug and toxic compound extrusion (MATE) | $Na^+$ | aminoglycosides, quinolones, chloramphenicol, ciprofloxacin, norfloxacin, pentamidine, cetrimide, benzalkonium chloride, acriflavine |
| ATP-binding cassette (ABC) | ATP hydrolysis | doxorubicin, vinblastine, Oxacillin, imipenem, nafcillin, penicillin G, methicillin, cefotaxime, moenomycin, erythromycin, macrolides |

*See, e.g, Jang, S., "Multidrug Efflux Pumps in *Staphylococcus aureus* and Their Clinical Implications," *J. Microbiology* 54:1-8 (2016), which is hereby incorporated by reference in its entirety.

In some embodiments, the antibiotic molecule is an efflux pump inhibitor (EPI). The efflux pump inhibitor (EPI) may be a peptidomimetic compound.

In certain embodiments, the efflux pump inhibitor is selected from the group consisting of phenylalanine arginyl β-naphthylamide (PaβN; MC-207,110), Pro-D-hPhe-3-aminoquinoline (MC-04,124), pyridopyrimidine derivative (D13-9001), naphthylmethyl-piperazine (NMP), 3,3-dimethyl-5-cyano-8-morpholino-6-(phenethylthio)-3,4-dihydro-1H-pyrano[3,4-c]pyridine (MBX2319), D13-9001, and derivatives thereof. See, e.g., Askoura et al., "Efflux Pump Inhibitors (EPIs) as New Antimicrobial Agents Against *Pseudomonas aeruginosa,*" *Libyan J. Med.* 10.3402 (2011) and Lamers et al., "The Efflux Inhibitor Phenylalanine-Arginine Beta-Naphthylamide (PAβN) Permeabilizes the Outer Membrane of Gram-Negative Bacteria," *PloS One* 8(3): e60668 (2013), which are hereby incorporated by reference in its entirety.

Any suitable cleavable linker can be utilized so long as the linker is susceptible to cleavage inside of the bacterial cells following cell uptake via the transporter(s). Preferred cleavable linkers are those that form an ester bond with the antibiotic molecule (and are therefore susceptible to cleavage by esterases, particularly intrabacterial esterases).

In certain embodiments, the cleavable linker is $—C(O)—(CH_2)_n—C(O)—$ where n is an integer from 1 to 14, $—C(O)—(CH_2)_m—CH{=}CH—C(O)—$ where m is an integer from 1 to 10, $—C(O)—CH{=}CH—C(O)—$, —C(O)—(1,2-cyclohexyl)-C(O)—, and —C(O)—Ar—C(O)— where Ar is a phenyl group, naphthyl group, or other multi-ring aromatic group. As an alternative, any of the above-identified linkers can include an additional $—(CH_2)_q—C(O)—$ group where q is from 1 to 10, such as $—C(O)—(CH_2)_n—C(O)—(CH_2)_q—C(O)—$, $—C(O)—(CH_2)_m—CH{=}CH—C(O)—(CH_2)_q—C(O)—$, $—C(O)—CH{=}CH—C(O)—(CH_2)_q—C(O)—$, $—C(O)—(1,2\text{-cyclohexyl})\text{-}C(O)—(CH_2)_q—C(O)—$, and $—C(O)—Ar—C(O)—(CH_2)_q—C(O)—$ where n, m, and q are defined as above. In accordance with these embodiments, n may be 1 to 10, 1 to 8, 1 to 6, or 1 to 4; m may be 1 to 8, 1 to 6, or 1 to 4; and q may be 1 to 8, 1 to 6, or 1 to 4.

In one embodiment, the conjugated prodrug may be selected from the group consisting of:

(i)

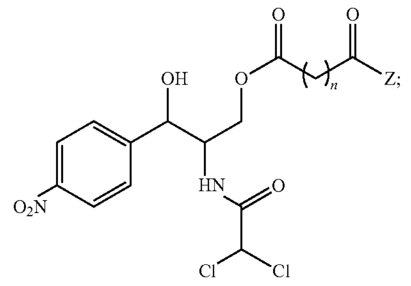

(ii)

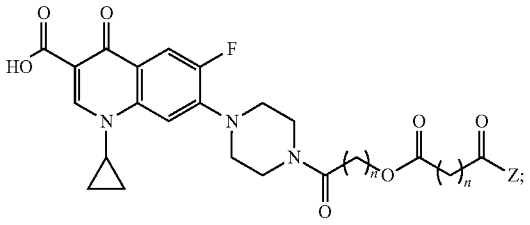

(iii)

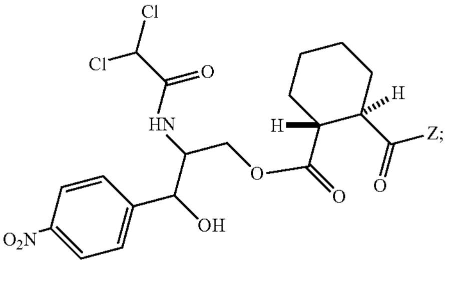

-continued (iv)

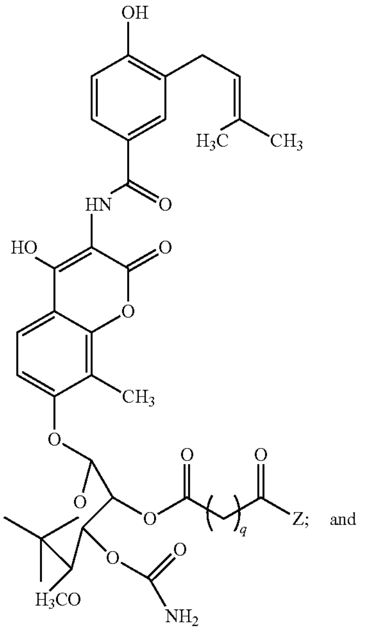

and (v)

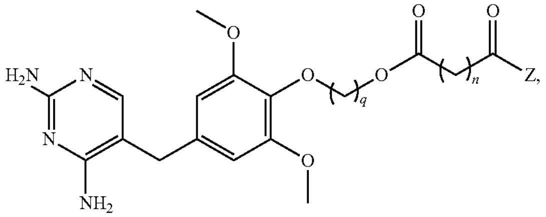

where n is an integer from 1 to 14 or, alternatively, 1 to 10, 1 to 8, 1 to 6, or 1 to 4; q is an integer from 1 to 10, 1 to 8, 1 to 6, or 1 to 4; and Z is the peptide. In certain embodiments, n is 2 or 4, q is 2, and Z is a dipeptide or tripeptide as described herein.

In certain embodiments, peptide Z is selected from the group consisting of Gly-Gly, Gly-Gly-Gly, Gly-Gly-Gly-Gly (SEQ ID NO: 1), Ala-Ala, Ala-Ala-Ala, Gly-Ser, Lys-Lys, Asp-Asp, Phe-Phe, Phe-Phe-Arg-Arg (SEQ ID NO: 2), Gly-Gly-Phe, Gly-Gly-Phe-Phe (SEQ ID NO: 3), Gly-Ala, Gly-Lys, Gly-Arg, Gly-His, Gly-Thr, Gly-Asn, Gly-Gln, Gly-Cys, Gly-Ser, Gly-Pro, Gly-Ile, Gly-Leu, Gly-Met, Gly-Phe, Gly-Trp, Gly-Tyr, Gly-Val, Gly-Asp, Gly-Phe-Gly, Gly-Glu, Phe-Phe-Gly, Phe-Phe-Gly-Gly (SEQ ID NO: 4).

Thus, the peptide Z may be selected from the group consisting of L-Gly-L-Gly, L-Gly-L-Gly-L-Gly, L-Gly-L-Gly-L-Gly-L-Gly (SEQ ID NO: 1), L-Ala-L-Ala, L-Ala-L-Ala-L-Ala, L-Gly-L-Ser, L-Lys-L-Lys, L-Asp-L-Asp, L-Phe-L-Phe, L-Phe-L-Phe-L-Arg-L-Arg (SEQ ID NO: 2), L-Gly-L-Gly-L-Phe, L-Gly-L-Phe-L-Gly, L-Phe-L-Gly-L-Gly, L-Gly-L-Gly-L-Phe-L-Phe (SEQ ID NO: 3), L-Gly-L-Gly-L-Gly-L-Gly-L-Gly (SEQ ID NO: 5), L-Gly-L-Lys, L-Asp-L-Asp, L-Gly-L-Asp, L-Gly, and L-Gly-L-Gly-NH—$CH_3$. In other embodiments, peptide Z is selected from the group of D-Gly-D-Gly, D-Gly-D-Gly-D-Gly, D-Gly-D-Gly-D-Gly-D-Gly, D-Ala-D-Ala, D-Ala-D-Ala-D-Ala, D-Gly-D-Ser, D-Lys-D-Lys, D-Asp-D-Asp, D-Phe-D-Phe, D-Phe-D-Phe-D-Arg-D-Arg, D-Gly-D-Gly-D-Phe, D-Gly-D-Phe-D-Gly, D-Phe-D-Gly-D-Gly, D-Gly-D-Gly-D-Phe-D-Phe, D-Gly-D-Gly-D-Gly-D-Gly-D-Gly, D-Gly-D-Lys, D-Asp-D-Asp, D-Gly-D-Asp, D-Gly, and D-Gly-D-Gly-NH—$CH_3$. In other embodiments, peptide Z is selected from the group of L-Gly-D-Leu, L-Gly-D-Ala, L-Gly-D-Ser, D-Ser-L-Gly, L-Gly-L-Gly-D-Phe, and L-Gly-L-Gly-D-Phe-D-Phe. Of these exemplary peptides listed, those bearing a glycine residue at the first position are generally preferred.

The conjugates of the present invention can be prepared by conjugating the antibiotic molecule to the peptide via the linker. Any suitable approach can be used to link the antibiotic molecule (or a variant thereof) to the peptide. One exemplary approach includes reacting an acid anhydride (e.g., succinic anhydride, glutaric anhydride, maleic anhydride, adipic anhydride, pimelic anhydride, suberic anhydride, azelaic anhydride, cyclohexane-1,2-dicarboxylic anhydride, phthalic anhydride, 2,3-naphthalenedicarboxylic anhydride) to an antiobiotic molecule bearing an available hydroxyl group to yield an ester-derivatized antiobiotic molecule, which is then coupled to the peptide via peptide bond formation between the N-terminal amino acid and the available carboxylic acid of the derivatized antibiotic molecule. Another exemplary approach includes first reacting a suitable monoacid containing a hydroxyl group, such as 2-hydroxyacetic acid, 3-hydroxypropanoic acid, or 4-hydroxybutanoic acid, to an available amine or ring nitrogen of the antiobiotic molecule under appropriate conditions (e.g., HBTU, DIEA, and DMF), followed by next reacting a reagent that introduces an ester group (e.g., N-hydroxy succinimide, N-hydroxy-glutarimide, N-hydroxy maleimide, 1-hydroxyazepane-2,7-dione, 1-hydroxyazocane-2,8-dione, 1-hydroxyazonane-2,9-dione, 2-hydroxyisoindoline-1,3-dione, 2-hydroxy-1H-benzo[f]isoindole-1,3(2H)-dione; polymer-supported DCC, $CH_3Cl$) to the previously introduced hydroxyl group, which is then followed by peptide coupling as above (e.g., peptide, DIEA).

Figure 15:
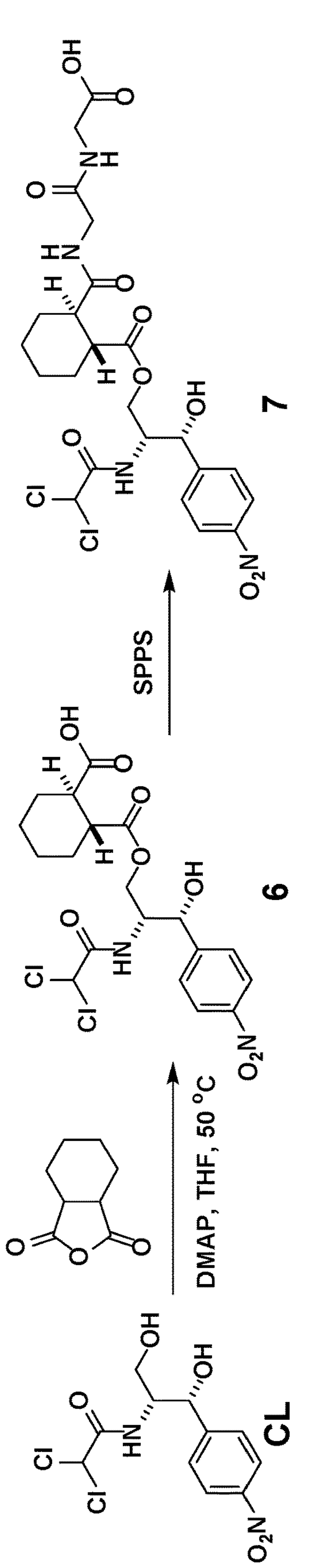
FIG. 15 is a reaction scheme showing the synthesis of chloramphenicol prodrug compounds 6 and 7 using cyclohexane-1,2-dicarboxylic acid to replace the succinate linker, thereby forming unconjugated prodrug 6 and its diglycine-conjugated derivative 7.

Exemplary synthesis schemes for (i) and (ii) are shown in FIGS. 2A-2C, 7, and 16, and described in the accompanying Examples. An exemplary synthesis scheme for (iii) is shown in FIG. 15 and described in the accompanying Examples.

Exemplary synthesis schemes for (iv) and (v) are shown below:

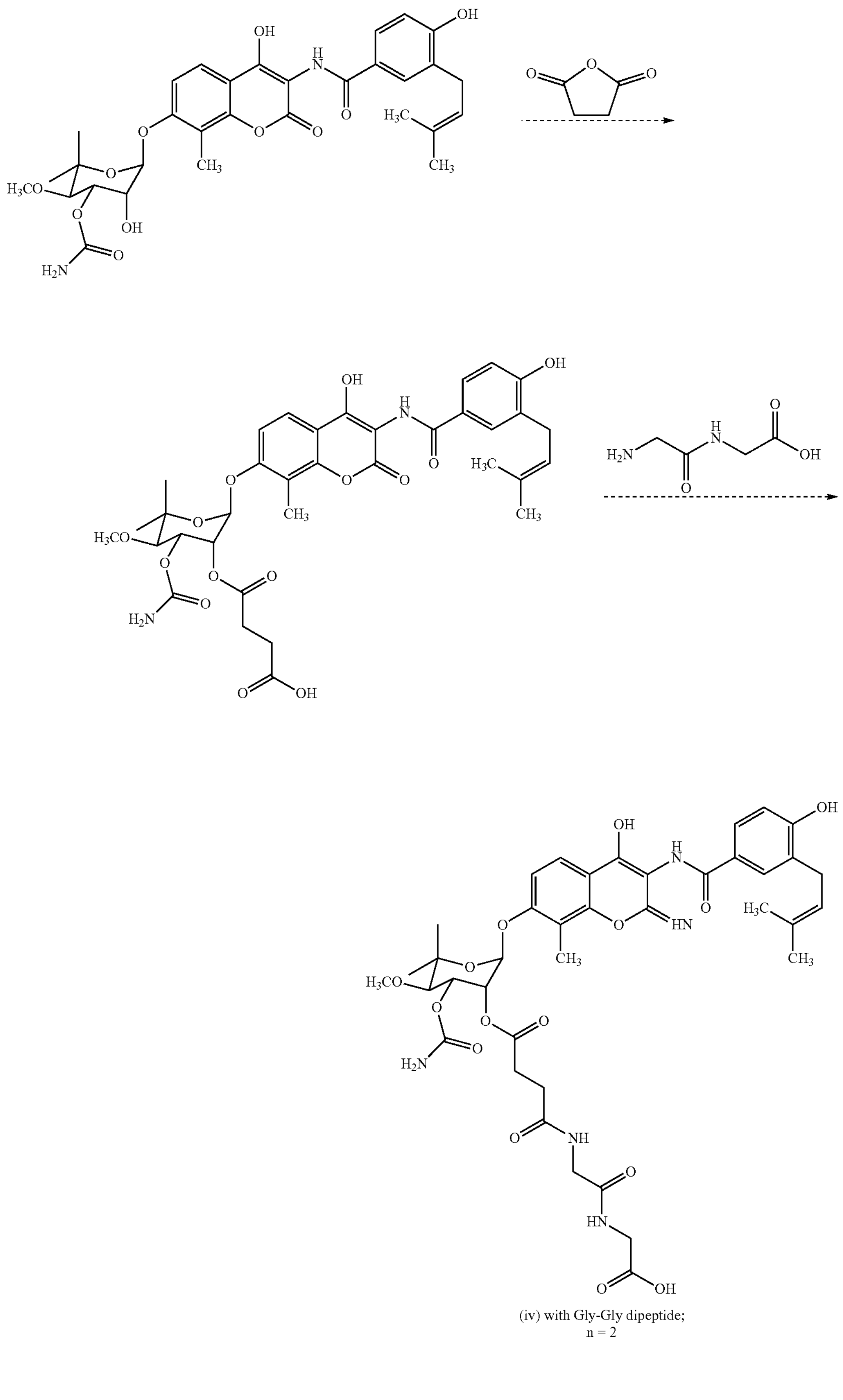
(iv) with Gly-Gly dipeptide;
n = 2

-continued

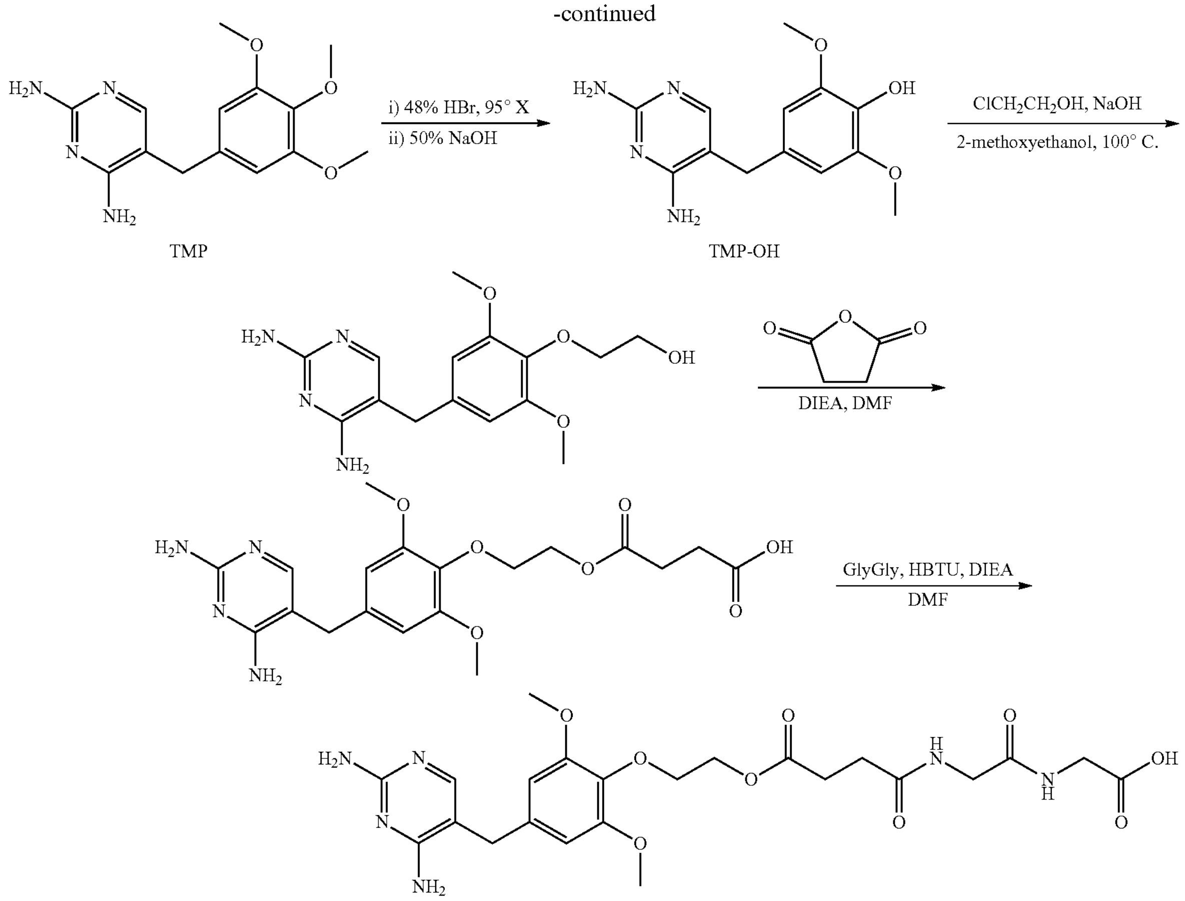

(v) with Gly-Gly dipeptide;
n = 2; q = 2

Alternatively, a number of ester-derivatized antiobiotic molecules are available commercially or readily synthesized, and can be used to prepare conjugates of the present invention. Under acidic conditions, these derivatives take the form of an acid that is reactive with the amino group of an amino acid during peptide synthesis. Examples include, without limitation, chloramphenicol succinate sodium, eromycin succinate, trimethoprim succinate, ciprofloxacin succinate, novobiocin succinate, and benzylpenicillin succinate.

As indicated above, once the ester-derivatized antibiotic molecule is obtained, the so-derivatized antibiotic molecule can be coupled to the N-terminal end of the peptide chain using any of a variety of solid- or liquid-phase peptide synthesis protocols. Exemplary conditions for linking the peptide to the antibiotic molecule are illustrated in the accompanying Examples.

A second aspect of the present disclosure relates to a pharmaceutical composition comprising a pharmaceutically acceptable carrier and a conjugated prodrug of the present disclosure.

The pharmaceutical composition may comprise one, two, three, four, five, or more conjugated prodrugs. In some embodiments, the pharmaceutical composition comprises two prodrugs. For example, the pharmaceutical composition may comprise a first prodrug comprising an efflux pump inhibitor and a second prodrug comprising an antimicrobial agent which inhibits metabolic activities.

Various suitable efflux pump inhibitors are described above.

The antimicrobial agent which inhibits metabolic activities may be selected from the group consisting of, e.g., aminoglycosides, aminocoumarins, β-lactams, macrolides, ketolides, lincosamides, streptogramins, quinolones, rifamycins, tetracyclines, oxazolidinones, glycylcycline, amphenicals, and polymyxins. Specific examples of antimicrobial agents which inhibit metabolic activities are identified above.

In some embodiments, when the pharmaceutical composition comprises two prodrugs, the first prodrug may comprise a peptide conjugated to PAβN and a peptide conjugated to a β-lactam. Suitable β-lactams are described above and include, for example, amoxicillin, ampicillin, piperacillin, cefotaxime, ceftazidime, and ciprofloxacin.

In other embodiments, when the pharmaceutical composition comprises two prodrugs, the first prodrug may comprise a peptide conjugated to PAβN and a peptide conjugated to a fluoroquinone. Suitable fluoroquinones are described above and include, e.g., ciprofloxacin, levofloxacin, gatifloxacin, moxifloxacin, ofloxacin, and norloxacin.

In certain embodiments, when the pharmaceutical composition comprises two prodrugs, the first prodrug may comprise a peptide conjugated to PAβN and a peptide conjugated to a macrolide. Suitable fluoroquinones are described above and include, e.g., azithromycin, clarithromycin, erythromycin, oleandomycin, rokitamycin, rosaramicin, roxithromycin, and troleandomycin.

In some embodiments, the pharmaceutically acceptable carrier is an aqueous medium. In one embodiment, the aqueous medium is a sterile isotonic aqueous buffer, which is typically well tolerated for administration to an individual. Additional exemplary aqueous media include, without limitation, normal saline (about 0.9% NaCl), phosphate buffered saline (PBS), sterile water/distilled autoclaved water (DAW), as well as cell growth medium (e.g., MEM, with or without serum), aqueous solutions of dimethyl sulfoxide (DMSO), polyethylene glycol (PEG), and/or dextran (less than 6% per by weight).

To improve patient tolerance to administration, the pharmaceutical composition may have a pH of about 4.5 to about 8.5. In some embodiments, sodium hydroxide or hydrochloric is added to the pharmaceutical composition to adjust the pH.

In other embodiments, the pharmaceutical composition includes a weak acid or salt as a buffering agent to maintain pH. Citric acid has the ability to chelate divalent cations and can thus also prevent oxidation, thereby serving two functions as both a buffering agent and an antioxidant stabilizing agent. Citric acid is typically used in the form of a sodium salt, typically 10-500 mM. Other weak acids or their salts can also be used.

The pharmaceutical composition may also include solubilizing agents, preservatives, stabilizers, emulsifiers, and the like. A local anesthetic (e.g., lidocaine, benzocaine, etc.) may also be included in the compositions, particularly for injectable forms, to ease pain at the site of the injection. Thus, in some embodiments, the composition is suitable for administration intravenously, parenterally, orally, mucosally, intraperitoneally, or topically.

As used herein, the term "about" when used in connection with a numerical value denotes an interval of accuracy that is ±10% in certain embodiments, ±5% in other embodiments, ±2.5% in still further embodiments, and ±1% in yet another embodiment.

Dosage forms of the conjugated prodrug of the invention can contain any suitably effective amount of the conjugated prodrug. In some embodiments, the conjugated prodrug is present at a concentration of about 1 μg/ml to about 100 mg/ml. Furthermore, the conjugated prodrug can be present in an amount from about 5 μg/ml to about 1000 μg/ml, or 5 μg/ml to about 800 μg/ml, 5 μg/ml to about 600 μg/ml, or 10 μg/ml to about 250 μg/ml.

A third aspect of the present disclosure relates to a method of enhancing the intracellular concentration of an antibiotic agent in a bacterium. This method involves contacting a bacterium with a conjugated prodrug according to the present disclosure, where the conjugated prodrug is taken up by the bacterium and the linker is cleaved intracellularly to release the antibiotic agent from the prodrug, causing an increase in the intracellular concentration of the antibiotic agent.

In carrying out the methods of the present disclosure, the contacting step may be carried out in vitro or in vivo.

Examples of bacteria that may be contacted and bacterial infections that are treatable by the conjugated prodrug and pharmaceutical compositions described herein include, without limitation, *Escherichia coli, Pseudomonas aeruginosa, Klebsiella pneumonia, Acinetobacter baumannii, Neisseria gonorrhoeae, Haemophilus influenza, Clostridium difficile* (*C. diff*), *Enterobacter faecalis, Staphylococcus aureus*, Methicillin Resistant *Staphylococcus aureus* (MRSA), *Serratia marcescens, Helicobacter pylori, Saccharomyces cervisiae, Streptococcus thermophiles, Lactococcus lactis, Streptococcus agalactiae, Beta Hemolytic streptococcus, Mycobacterium bovis, Listeria monocytogenes, Peptostreptococcus micros, Fusobacterium nucleaturm, Porphyromonas gingivalis, Salmonella tyrphimurium*, and/or *Bacciluss subtillus*, which may infect, for example, wounds, skin, eyes, ears, nose and/or the gastrointestinal (GI) tract. As used herein, the "gastrointestinal tract" refers to the entire alimentary canal, from the oral cavity to the rectum. The gastrointestinal tract includes the oral cavity (mouth or buccal cavity), pharynx (throat), esophagus, stomach, small intestine, and large intestine (cecum, colon, rectum, anus).

In some embodiments, the conjugated prodrug and pharmaceutical compositions of the present disclosure are capable of inhibiting bacterial growth and, accordingly, are useful as bactericidal, antibacterial, and anti-infective agents.

In some embodiments, the conjugated prodrug and pharmaceutical compositions of the present disclosure are capable of inhibiting bacterial growth by at least about 20%, at least about 30%, at least about 40%, at least about 50%, at least about 60%, at least about 70%, at least about 80%, at least about 90%, by at least 95%, or by 100% when compared to bacterial growth in the absence of the conjugated prodrug or pharmaceutical compositions described herein.

A fourth aspect of the present disclosure relates to a method of treating a patient for a bacterial infection. This method involves administering a conjugated prodrug or pharmaceutical composition according to the present disclosure to a patient in need of treatment.

Suitable patients that can be treated include both veterinary patients, typically but not exclusively mammals, as well as human patients.

In some embodiments, the patient is selected from the group consisting of primates (e.g., humans, monkeys), equines (e.g., horses), bovines (e.g., cattle), porcines (e.g., pigs), ovines (e.g., sheep), caprines (e.g., goats), camelids (e.g., llamas, alpacas, camels), rodents (e.g., mice, rats, guinea pigs, hamsters), canines (e.g., dogs), felines (e.g., cats), leporids (e.g., rabbits). In some embodiments, the selected patient is an agricultural animal, a domestic animal, or a laboratory animal. In other embodiments, the patient is a human.

The patient may be an infant, an adolescent, or an adult. In some embodiments, the patient has been diagnosed with pneumonia, a chronic obstructive pulmonary disease, sinusitis, bronchitis, or cystic fibrosis.

Administration of the prodrug or pharmaceutical composition of the present invention can be repeated. In some embodiments, administration of the prodrug or pharmaceutical composition is repeated on a daily schedule (i.e., once, twice, thrice, or four times daily) or according to a periodic schedule (i.e., once weekly, bimonthly, once monthly). For example, the administering may be carried out two to four times daily.

In some embodiments, the administering is repeated daily over a period of at least 3, 4, 5, 6, 7, 8, 9, 10, 11, 12, 13, 14, 15, 16, 17, 18, 19, 20, 21, 22, 23, 24, 25, 26, 27, 28, 29, 30 days, or more. Thus, the administering may be repeated daily over a period of at least three days. In another embodiment, the administering is repeated daily over a period that is up to 30 or more days.

The prodrug or the pharmaceutical composition may be administered parenterally, subcutaneously, intravenously, intradermally, intramuscularly, intraperitoneally, by implantation, by intracavitary or intravesical instillation, intraarterially, intralesionally, intradermally, peritumorally, intratumorally, or by introduction into one or more lymph nodes. In some embodiments, the administering is carried out intravenously, parenterally, orally, mucosally, intraperitoneally, or topically.

Whether present in the pharmaceutical composition or not, the conjugated prodrug may be administered in an amount of about 1 mg to about 1000 mg per dose, about 5 mg to about 800 mg per dose, about 10 mg to about 500 mg per dose, or any amount there between.

The dose of the conjugated prodrug may be higher than the tolerated dose of the unconjugated antibiotic agent.

In some embodiments, the bacterial infection is due to *Pseudomonas* spp., *Klebsiella* spp., *Enterobacter* spp., Escherichi spp., *Morganella* spp., *Citrobacter* spp., *Serratia*, spp. or Acintetobacter spp., *Streptococcus* spp., *Staphylococcus* spp., *Corynebacterium* spp., *Clostridium* spp., *Listeria* spp., and *Salmonella* spp.

EXAMPLES

The following examples are provided to illustrate embodiments of the present invention but they are by no means intended to limit its scope.

Materials and Methods for Examples 1-5

Experimental materials and instruments. All the solvents and chemical reagents were used directly as received from the commercial sources without further purification unless otherwise stated. Carboxylesterase (CES) from porcine liver was purchased from Sigma-Aldrich (lyophilized powder, >15 units/mg solid; Unit definition: One unit will hydrolyze 1.0 μmole of ethyl butyrate to butyric acid and ethanol per min at pH 8.0 at 25). CLsuGG, CLsuG, CLsuGGG were purified with Agilent 1100 Series Liquid Chromatography system, equipped with an XTerra C18 RP column and Variable Wavelength detector. The LC-MS spectra were obtained with a Waters Acquity Ultra Performance LC with Waters MICROMASS detector. $^1$H NMR spectra were obtained on Varian Unity Inova 400, and TEM images on a Morgagni 268 transmission electron microscope.

Hydrolysis assay: Wild-type *E. coli* strains (K12) were harvested by centrifugation and the cell pellets were lysed using a sonic device. After centrifugation, the supernatant was collected and the proteinase inhibitor was added in the *E. coli* lysate. The concentration of *E. coli* lysate was normalized by the fluorescence intensity of 5-carboxyfluorescein diacetate (CFDA). Briefly, different concentrations of CES (4 U/mL, 2 U/mL, 1 U/mL, 0.5 U/mL, 0.25 U/mL, 0.125 U/mL, 0.0625 U/mL, 0.03125 U/mL, 0.015625 U/mL and 0 U/mL) and different amount of *E. coli* lysates were prepared in PBS buffer. Followed by, 25 μM of CFDA was added in and incubated at room temperature for 1 hour. Then the fluorescence was tested to draw a fluorescence-concentration dependent curve for figuring out the concentration of *E. coli* lysates. Solutions of CLsuGG (200 μM) were prepared in pH 7.4 PBS buffer. CES and *E. coli* lysate (0.1 U/mL) were added and incubated with above solutions at 37° C. for 24 hours. At different time points, the solution was taken out, extracted with an equal volume of butanol, concentrated to dryness, and resuspended with butanol for HPLC analysis. HPLC was performed with Agilent 1100 Series Liquid Chromatograph equipped with an XTerra C18 reverse phase column and Variable Wavelength Detector. The hydrolyzed mixture resuspended in 1 mL of butanol was injected to HPLC mobile phase (0.1% trifluoroacetic acid, the starting ratio: 10% acetonitrile and 90% water). The system was run at a flow rate of 10 mL/min. Sample detection was achieved at 220 nm.

TEM sample preparation: A negative staining technique was used to study the TEM images. First, Applicant glowed discharged the 400 mesh copper grids coated with continuous thick carbon film (~35 nm) prior to use to increasing the hydrophilicity. After loading samples (7 μL) on the grid, the grid was rinsed using dd-water for twice or three times. Immediately after rinsing, the grid containing sample was stained with 2.0% w/v uranyl acetate for three times. Afterwards, the grid was allowed to dry in air.

Light scattering sample preparation: The static light scattering experiments were performed by using an ALV (Langen, Germany) goniometer and correlator system with a 22 mW HeNe (λ=633 nm) laser and an avalanche photodiode detector. All samples were dissolved in PBS buffer. After the addition of CES to the solution of CLsuGG for 24 hours, corresponding enzymatic hydrolyzed samples were obtained. The SLS tests were carried out at room temperature, and the angles of light scattering we chose were 30°, 60°, 90°, and 120°, respectively. The resulting intensity ratios are proportional to the amount of aggregates in the samples.

Bacteria culture and inhibitory activity assay: Single esterase (BioH, YjfP, FrsA, YbfF, YfbB, YqiA, YeiG, or and YpfH) deletion mutants were purchased from Dharmacon Horizon Discovery (Cambridge, United Kingdom). The K12 wild-type *E. coli* strain (MG1655) was cultured in autoclaved LB medium (25 g/L LB broth/water) in a shaker-incubator overnight to stationary growth phase, and then sub-cultured in the same medium after dilution to $OD_{600}$ of 0.05. Compounds were added at different concentrations. The mixture of bacteria and compounds were placed (200 μL/well) into 96-well clear flat bottom plates. In all plates, the $OD_{600}$ was measured before and after 16 hour incubation at 37° C.

Cell culture and cell viability assay: All mammalian cell lines were purchased from the American Type Culture Collection (ATCC, Manassas, VA, USA). The HS-5 and HEK293T cells were propagated in Dulbecco's Modified Eagle's Medium (DMEM) supplemented with 10% fetal bovine serum (FBS) and 1% antibiotics in a fully humidified incubator containing 5% $CO_2$ at 37° C., HepG2 cells in Eagle's Minimum Essential Media (MEM) supplemented with 10% FBS and 1% antibiotics in a fully humidified incubator containing 5% $CO_2$ at 37° C. Cells in exponential growth phase were seeded in a 96 well plate at a concentration of $1\times10^4$ cell/well, and were allowed to attach to the well for 24 hours at 37° C., 5% $CO_2$. The culture medium was removed and 100 μL culture medium containing corresponding compounds (immediately diluted from fresh prepared stock solution) at gradient concentrations (0 μM as the control) was placed into each well. After culturing at 37° C., 5% $CO_2$ for 24 hour, 48 hours, and 72 hours, each well was added with 10 μL of 5 mg/mL MTT ((3-(4,5-dimethylthiazol-2-yl)-2,5-diphenyltetrazolium bromide), and the plated cells were incubated at dark for 4 hours. 100 μL 10% SDS with 0.01M HCl was added to each well to stop the reduction and to dissolve the purple. After incubation of the cells at 37° C. for overnight, the OD at 595 nm of the solution was measured in a microplate reader. Data represent the mean±standard deviation of three independent experiments.

Figure 2A:
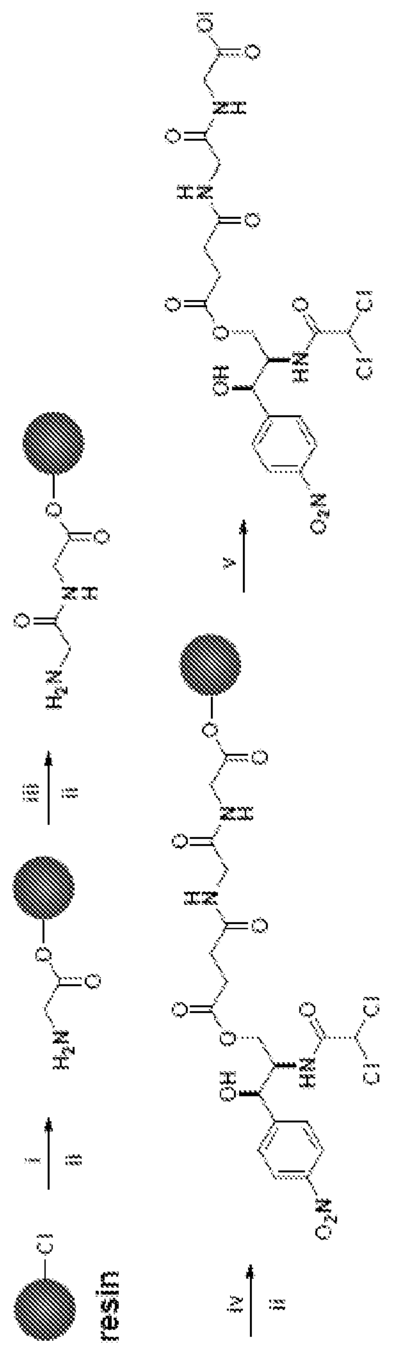
FIGS. 2A-2C are reaction schemes showing the synthesis of compound CLsuGG, compound CLsuG, and compound CLsuGGG by solid phase peptide synthesis using chloramphenicol succinate reaction with resin-bound glycine, diglycine, or tri-glycine.
Figure 2B:
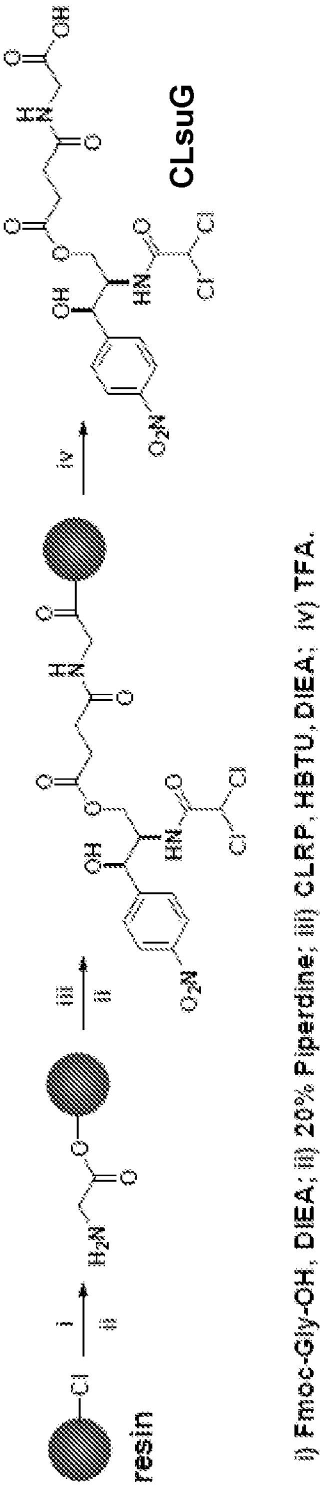
Figure 2C:
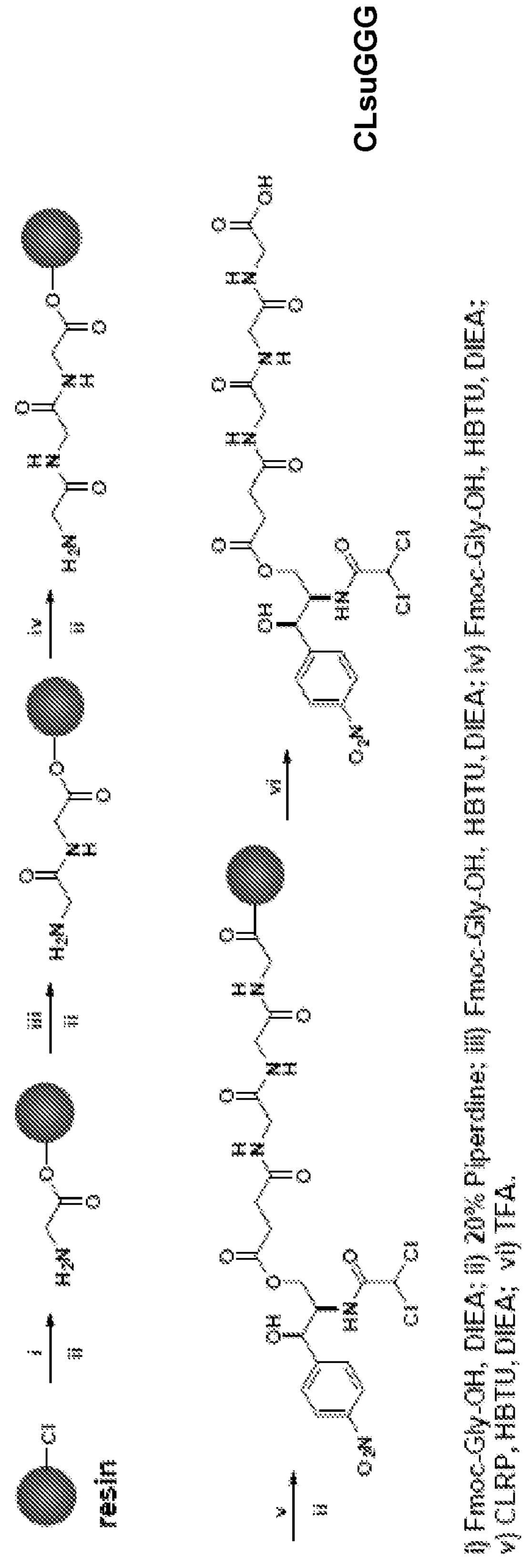

Example 1—Synthesis and Characterization of Peptide-Conjugated CL Prodrugs CLsuGG, CLsuG, CLsuGGG As shown in FIGS. 2A-C, the commercially available chloramphenicol succinate sodium (CLsu), after acidification, is suitable for solid phase peptide synthesis to produce all peptide-succinate chloramphenicol prodrugs. Briefly, chloramphenicol succinate sodium (150 mg) was dissolved in distilled water (3 mL), and HCl (1 M) was added dropwise until the pH of the mixture was adjusted to 2.0. The precipitate was washed several times with distilled water and dried for further use.

Compound CLsuGG. Solid phase peptide synthesis was used for the synthesis of CLsuGG. As shown in FIG. 2A, 2-chlorotrityl chloride resin and N-Fmoc-glycine was used for the synthesis. Then, CLsu was used to cap the N-terminal of the peptides. After cleaving the compounds from resin, CLsuGG was purified (yield: up to 90%) by reverse phase HPLC using HPLC grade acetonitrile and water with supplement of 0.1% trifluoroacetic acid as the eluents. $^1$H NMR (400 MHz, DMSO-d6, 25° C., ppm): δ 8.51 (d, J=8.0 Hz, 1H), 8.17 (m, 4H), 7.64 (d, J=12.0 Hz, 2H), 6.44 (s, 1H), 5.02 (s, 1H), 4.21 (m, 2H), 4.10 (m, 1H), 3.74 (dd, J=4.0, 8.0 Hz, 4H), 2.48 (m, 4H); $^{13}$C NMR (100 MHz, DMSO-d6, 25° C., ppm): δ 172.63, 171.53, 169.73, 164.04, 150.67, 147.02, 127.89, 123.32, 69.88, 66.70, 63.44, 53.93, 42.24, 40.97, 30.09, 29.33; ESI-MS m/z calcd. for $C_{19}H_{22}Cl_2N_4O_{10}$ [M]+: m/z=537.30, found [M-H]−535.24.

Compound CLsuG. Solid phase peptide synthesis was used for the synthesis of CLsuG. As shown in FIG. 2B, 2-chlorotrityl chloride resin and N-Fmoc-glycine was used for the synthesis. Then, CLsu was used to cap the N-terminal of the peptides. After cleaving the compounds from resin, CLsuG was purified (yield: up to 90%) by reverse phase HPLC using HPLC grade acetonitrile and water with supplement of 0.1% trifluoroacetic acid as the eluents. $^1$H NMR (400 MHz, DMSO-d6, 25° C., ppm): δ 8.51 (d, J=8.0 Hz, 1H), 8.24 (t, J=4.0 Hz, 1H), 8.17 (d, J=12.0 Hz, 2H), 7.64 (d, J=8.0 Hz, 2H), 6.44 (s, 1H), 5.03 (s, 1H), 4.21 (m, 2H), 4.10 (m, 1H), 3.75 (d, J=4.0 Hz, 2H), 2.46 (m, 4H); $^{13}$C NMR (100 MHz, DMSO-d6, 25° C., ppm): δ 172.51, 171.72, 171.55, 164.04, 150.69, 147.02, 127.89, 123.31, 69.85, 66.70, 63.40, 53.91, 41.05, 29.94, 29.31; ESI-MS m/z calcd. for $C_{17}H_{19}Cl_2N_3O_9$ [M]+: m/z=480.25, found [M-H]−478.10.

CLsuGGG. Solid phase peptide synthesis was used for the synthesis of CLsuGGG. As shown in FIG. 2C, 2-chlorotrityl chloride resin and N-Fmoc-glycine was used for the synthesis. Then, CLsu was used to cap the N-terminal of the peptides. After cleaving the compounds from resin, CLsuGGG was purified (yield: up to 90%) by reverse phase HPLC using HPLC grade acetonitrile and water with supplement of 0.1% trifluoroacetic acid as the eluents. $^1$H NMR (400 MHz, DMSO-d6, 25° C., ppm): δ 8.51 (d, J=8.0 Hz, 1H), 8.17 (m, 5H), 7.64 (d, J=8.0 Hz, 2H), 6.44 (s, 1H), 5.03 (s, 1H), 4.22 (m, 2H), 4.10 (m, 1H), 3.75 (m, 7H), 2.47 (m, 4H); $^{13}$C NMR (100 MHz, DMSO-d6, 25° C., ppm): δ 172.62, 171.70, 171.48, 169.68, 169.55, 164.05, 150.67, 147.02, 127.88, 123.32, 69.89, 66.70, 63.45, 53.93, 42.57, 42.14, 40.97, 30.09, 29.33; ESI-MS m/z calcd. for $C_{21}H_{25}Cl_2N_5O_{11}$ [M]+: m/z=594.36, found [M-H]−592.09.

Example 2—Hydrolysis Rate and MIC of Glycine Conjugates with CL

Figures 3A, 3B, 3C, 3D:
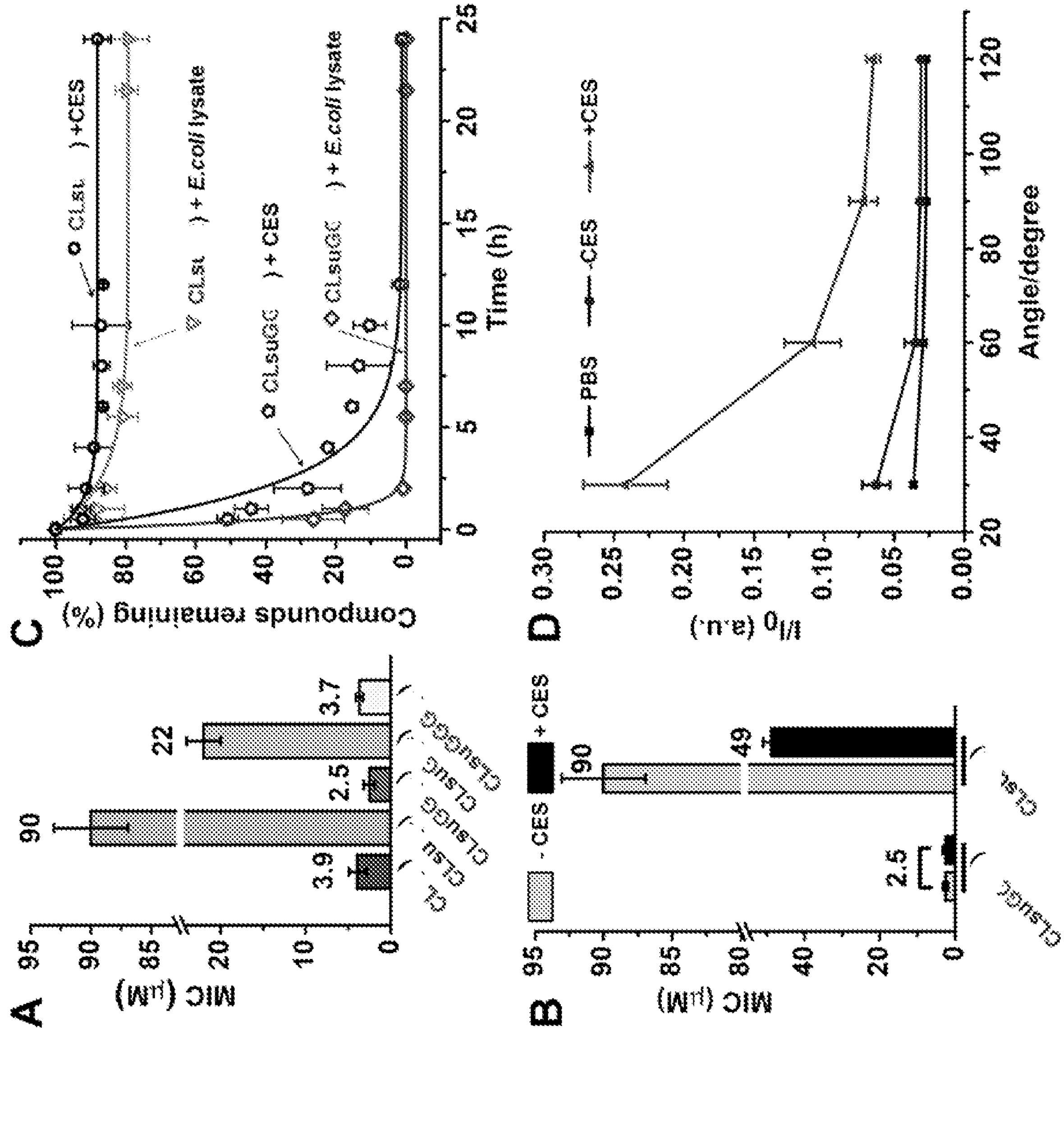
FIGS. 3A-3F show the characterization of CL, CLsu, CLsuGG, CLsuG, and CLsuGGG.

The antibacterial activities of the glycine-conjugates CLsuGG, CLsuG, and CLsuGGG against a wild-type *E. coli* was investigated (FIG. 3A). Although these conjugates differ only in the number of glycine residues, they exhibit drastically different antibacterial activity. CLsuGG shows high antibacterial activity, with the MIC value of 20 μM (10.7 μg/mL), which is comparable to that of CL (20 μM (6.5 μg/mL)). On the other hand, CLsuG exhibits the MIC of >200 μM (95.8 μg/mL), which is comparable to that of CLsu (>200 μM (84.6 μg/mL)). The conjugate CLsuGGG that contains three glycine residues exhibits similar efficacy (20 μM) than that of CLsuGG, indicating that the dipeptide GG is the smallest peptide useful for enhancing the antibacterial efficacy of the conjugates (Table 3).

TABLE 3

The Minimum Inhibitory Concentration (MIC) of Peptides-Conjugated CLsu Against *E. coli* (K-12)

| Compound | MIC (μM) | MIC (μg/mL) |
|---|---|---|
| CL | 20 | 6.5 |
| CLsu | >200 | >84.6 |
| CLsuGG | 20 | 10.7 |
| CLsuG | >200 | 95.8 |
| CLsuGGG | 20 | 11.9 |

To understand the origin of the potent antibacterial activity of CLsuGG, whether esterase is able to activate the prodrugs was examined. Surprisingly, the addition of exogenous carboxylesterase (CES) (Toone et al., "Enzymes in Organic Synthesis. 47. Active-Site Model for Interpreting and Predicting the Specificity of Pig Liver Esterase," *JACS* 112(12):4946-4952 (1990), which is hereby incorporated by reference in its entirety) only slightly increases the inhibitory efficacy of CLsu (i.e., reducing the MIC value from 90 to 49 μM) (FIG. 3B). The addition of CES, however, hardly affected the MIC value of CLsuGG, implying that CLsuGG likely is hydrolyzed by the catalysis of intrabacterial esterases. To confirm this assumption, the rate of the ester bond hydrolysis of CLsu and CLsuGG by the mammalian CES (Toone et al., "Enzymes in Organic Synthesis. 47. Active-Site Model for Interpreting and Predicting the Specificity of Pig Liver Esterase," *JACS* 112(12):4946-4952 (1990), which is hereby incorporated by reference in its entirety) and the lysates of *E. coli* was measured. FIG. 3C shows that the intrabacterial esterases (0.1 U/mL) hydrolyze CLsuGG completely within 2 hours (with the apparent first-order rate constant of $-1.868\ h^{-1}$). Although CLsuGG is able to undergo hydrolysis catalyzed by CES, it only reaches around 70% conversion after 2 hours, and the complete hydrolysis of CLsuGG catalyzed by CES takes more than 12 hours when the concentration of CES is 0.1 U/mL (with the apparent first-order rate constant of $-0.443\ h^{-1}$). On the other hand, CLsu hardly undergoes hydrolysis with the addition of CES, and less than 20% CLsu is hydrolyzed 24 hours after the addition of the *E. coli* lysate. Besides providing an explanation of the clinical failure of CLsu (Yogev et. al., "Pharmacokinetic Comparison of Intravenous and Oral Chloramphenicol in Patients with *Haemophilus influenzae* Meningitis," *Pediatrics* 67(5):656-660 (1981), which is hereby incorporated by reference in its entirety), these results indicate that the intrabacterial esterases catalyze the rapid hydrolysis of CLsuGG and contribute to the excellent inhibitory efficacy of CLsuGG against *E. coli.*

Figure 3E:
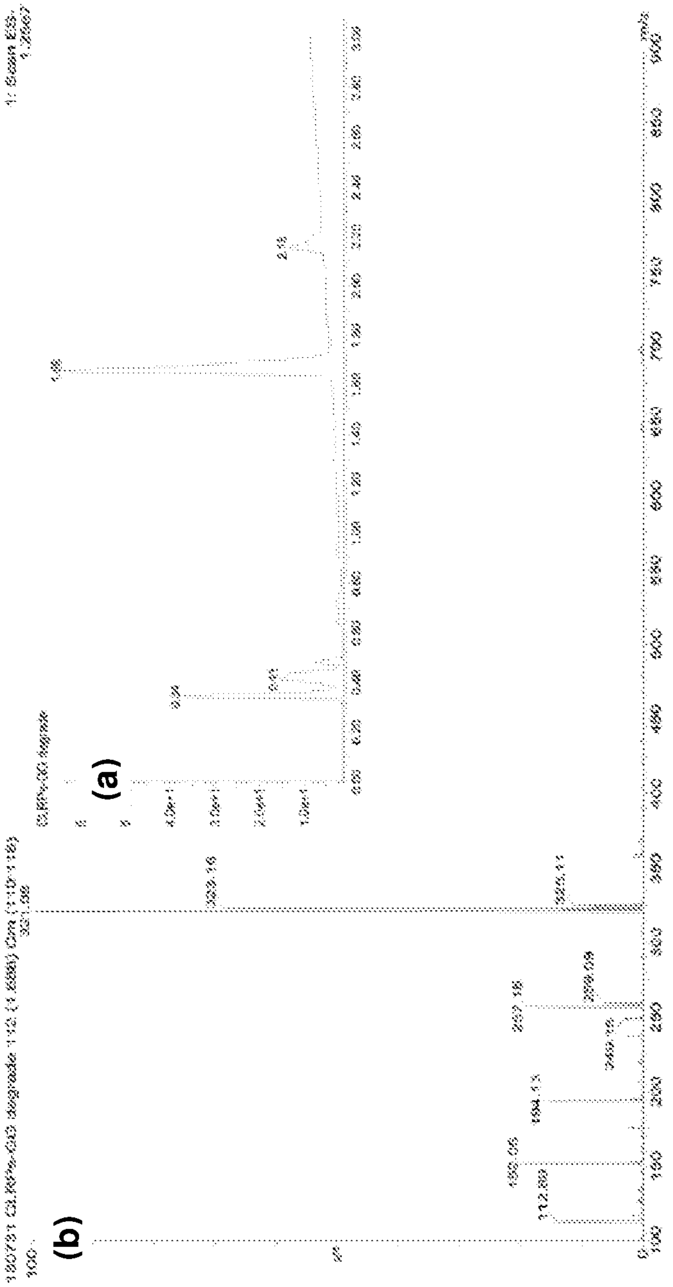
Figure 3F:
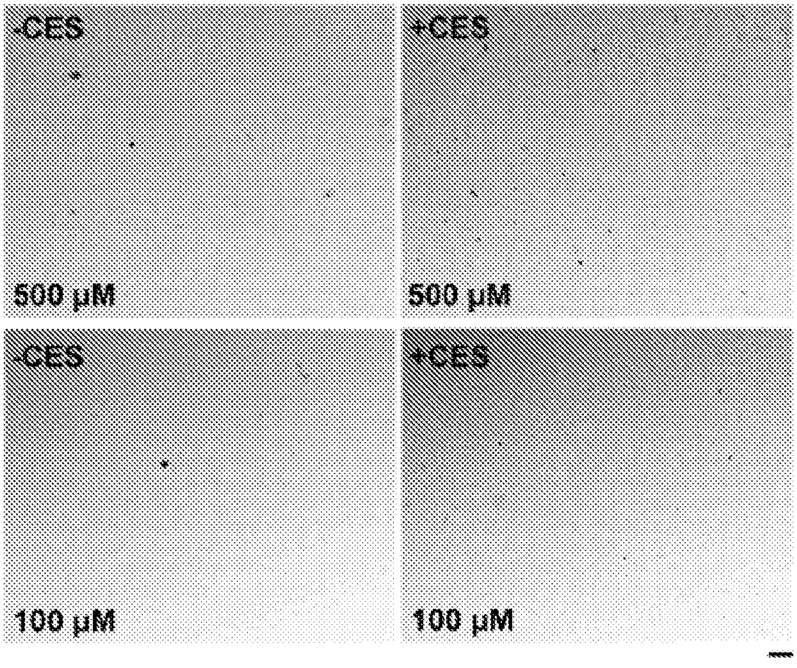

LC-MS results confirm that hydrolysis of CLsuGG regenerates CL (FIG. 3E). Moreover, the intensities of the static light scattering signals increase drastically after the addition of CES to the solutions of CLsuGG for 24 hours (FIG. 3D), agreeing with that the transmission electron microscopic (TEM) images show increased amount of nanoparticles after the addition of CES (FIG. 3F). Besides confirming that CLsuGG becomes CL after the hydrolysis catalyzed by esterases, the above results, collectively, indicate that the soluble CLsuGG is able to become CL, which has poor solubility, to favor the retention of CL inside *E. coli.*

Example 3—Uptake of CLsuGG

Figure 4A:
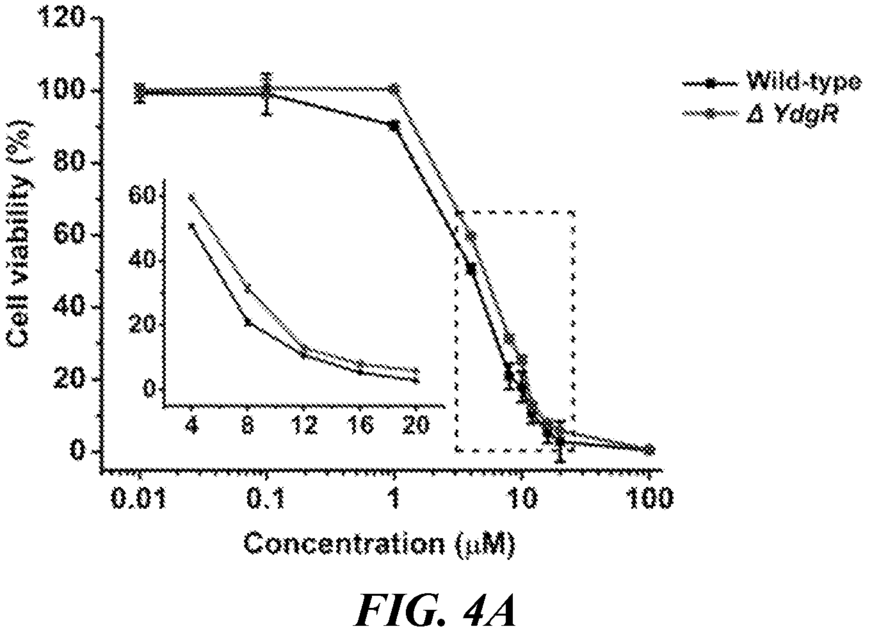
FIGS. 4A-4B show the antibacterial activity of CLsuGG against (i) YdgR transporter knockout mutants of *E. coli* (inset: corresponding magnified image of dash line square) (FIG. 4A) and (ii) FepA transporter knockout mutants of *E. coli* (inset: corresponding magnified image of dash line square) (FIG. 4B).
Figure 4B:
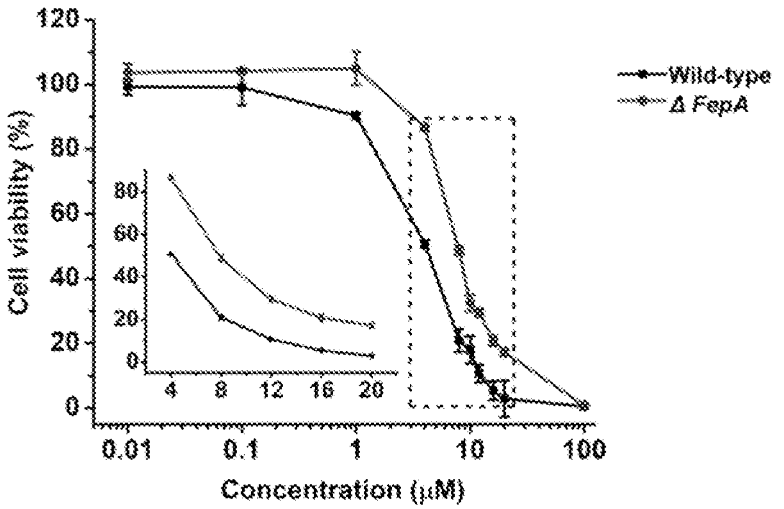

To verify whether bacterial oligopeptide transporters are involved in the uptake of CLsuGG, the activities of CLsuGG against the YdgR mutant and wild-type *E. coli* was compared (FIG. 4A). The deletion of YdgR, an inner membrane (IM) proton-coupled transporter for uptaking di- and tripeptides (Prabhala et al., "The Prototypical Proton-Coupled Oligopeptide Transporter YdgR from *Escherichia coli* Facilitates Chloramphenicol Uptake into Bacterial Cells," *J. Biol. Chem.* 293(3):1007-1017 (2018), which is hereby incorporated by reference in its entirety), indeed rescues the bacteria, i.e., increasing cell viability for about 10%. This observation suggests that YdgR assists the influx of the precursors into the bacteria, but is unlikely to be the major contributor. Further examination reveals that siderophore transporter, FepA (Hollifield & Neilands, "Ferric Enterobactin Transport System in *Escherichia coli* K-12. Extraction, Assay, and Specificity of the Outer Membrane Receptor," *Biochemistry* 17(10):1922-1928 (1978), which is hereby incorporated by reference in its entirety), also contributes to the uptake of CLsuGG (FIG. 4B). These results indicate that CLsuGG enters the bacteria via multiple paths, including diffusion.

Example 4—Role of Esterases on Hydrolysis of CLsuGG

Figure 5A:
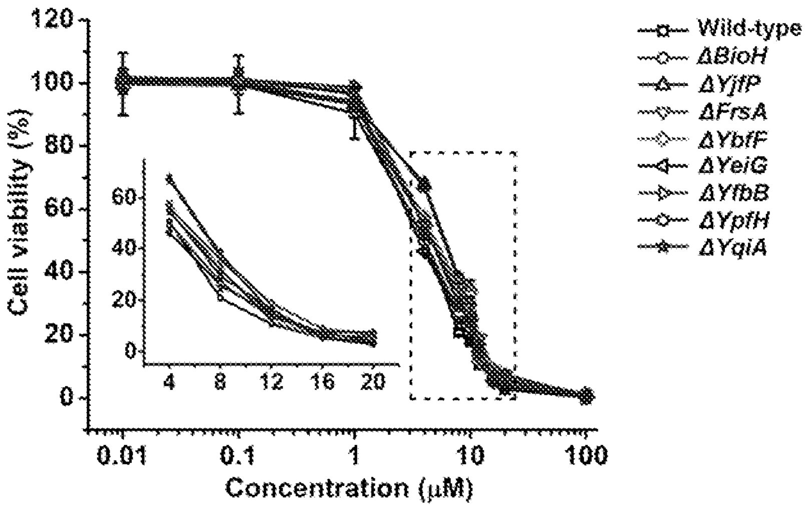
Figure 5B:
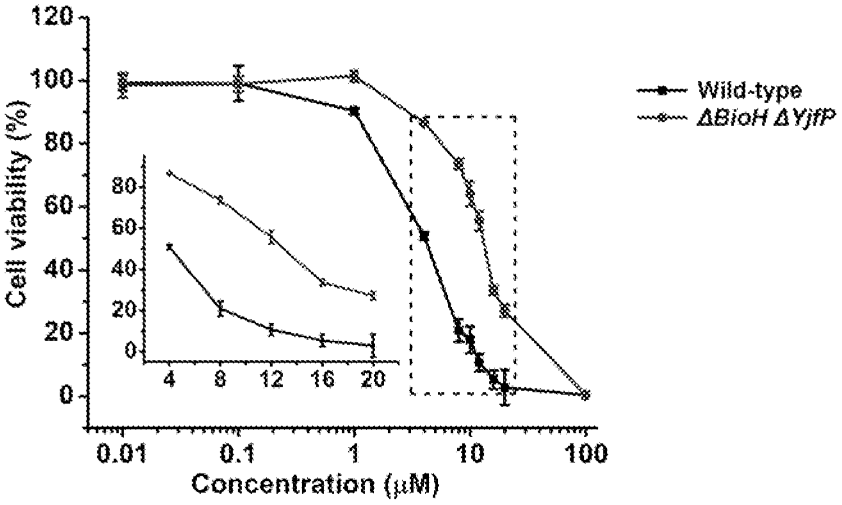
Figure 5C:
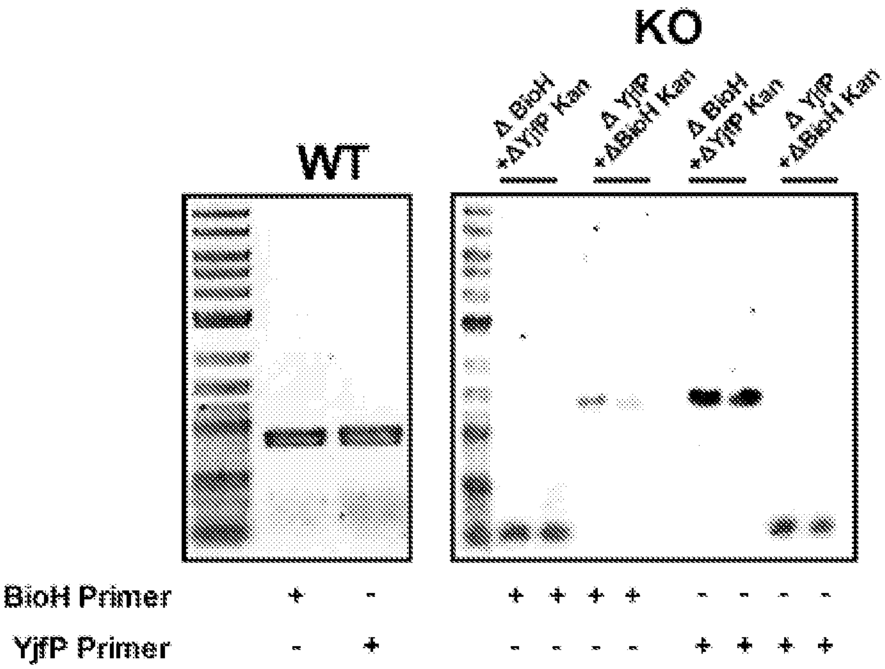
Figure 5D:
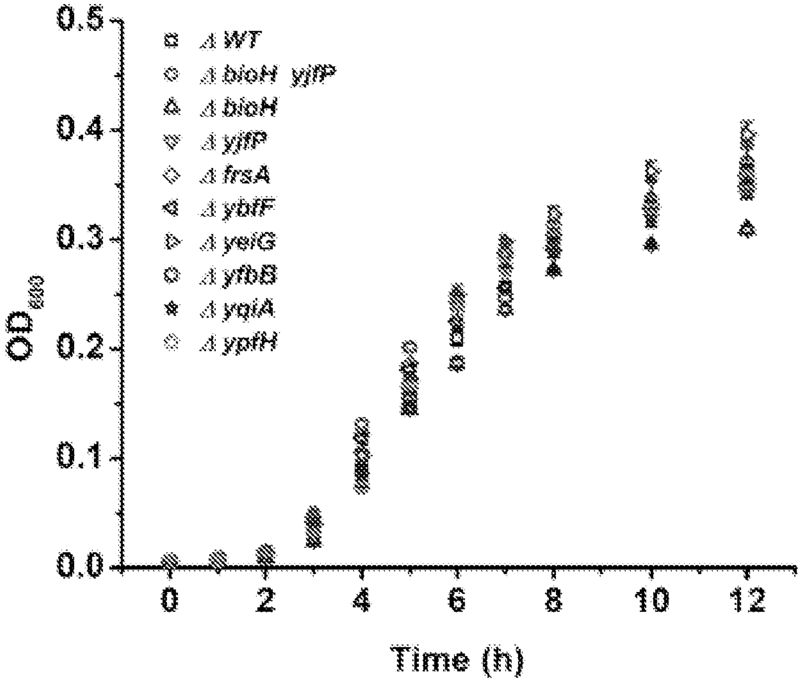

To examine the roles of different intrabacterial esterases on the hydrolysis of CLsuGG, the activities of CLsuGG against eight *E. coli* mutants that have one of bacterial esterase genes (i.e., BioH, YjfP, FrsA, YbfF, YeiG, YfbB, YpfH or YqiA) deleted was measured. As shown in FIG. 5A, the single gene deletion of the cytoplasmic esterase of *E. coli* reduces the antibacterial activities of CLsuGG slightly at different magnitudes (BioH, YjfP>FrsA, YbfF, YfbB, YqiA>YeiG, YpfH), which likely results from the specific activities of different esterases. To confirm the role of intrabacterial esterases, a double mutant *E. coli* was generated, with the deletion of BioH and YjfP genes (FIGS. 5C-5D). As shown in FIG. 5B, the double deletion of BioH and YjfP significantly attenuates the antibacterial activity of CLsuGG, down to 50% of the activity against the wild type *E. coli*. This result indicates that BioH and YjfP play a considerable role in the hydrolysis of CLsuGG. These studies confirm that, after CLsuGG enters *E. coli*, various esterases in bacterial cytoplasm rapidly convert CLsuGG to the active antibiotic agent (i.e., CL).

Example 5—Reduced Cytotoxicity of CLsuGG

Figure 6:
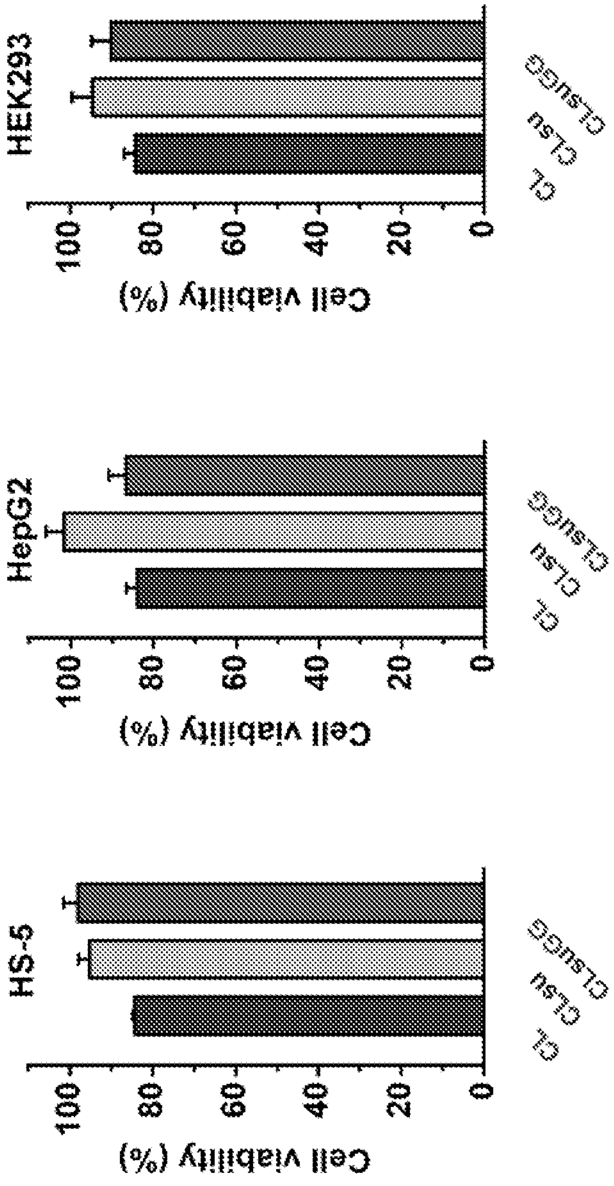
FIG. 6 is a panel of graphs showing the cell viability of HS-5 (left panel), HepG2 (middle panel), and HEK293 (right panel) cells incubated with CL, CLsu and CLsuGG for 24 hours, [CL]=[CLsu]=[CLsuGG]=20 μM.

CL inhibits the peptidyl transferase activity of the bacterial ribosome to exhibit excellent antibacterial activity, but its ability to inhibit protein synthesis also results in adverse effects against mammalian cells, including bone marrow suppression (Morley et al., "Residual Marrow Damage: Possible Explanation for Idiosyncrasy to Chloramphenicol," *British Journal of Haematology* 32(4):525-532 (1976), which is hereby incorporated by reference in its entirety). To assess the side effects of the conjugates, the cytotoxicities of CL, CLsu, and CLsuGG towards HS-5 (Roecklein & Torokstorb, "Functionally Distinct Human Marrow Stromal Cell-Lines Immortalized by Transduction with the Human Papilloma-Virus e6/e7 Genes," *Blood* 85(4):997-1005 (1995), which is hereby incorporated by reference in its entirety) and a bone marrow stromal cell line was compared. At the concentration of 20 μM (about 10 times of the MIC values), while CL reduced the viability of HS-5 cells, CLsu and CLsuGG were largely innocuous to HS-5 cells. The cytotoxicities of CL, CLsu, and CLsuGG against a hepatocyte cell line (HepG2) and a kidney cell line (HEK293) were also compared and it was found that the conjugation of GG hardly altered the cytotoxicity of CL. These results (FIG. 6) indicate that the conjugation of the dipeptide GG likely would reduce the major adverse effect of CL (i.e., bone marrow suppression).

Discussion of Examples 1-5

The evidence presented in Examples 1-5 demonstrates that conjugating the dipeptide GG to antibiotic succinate prodrugs enhances the efficacy and improves the safety of the existing antibiotics. Although the original objective was to merely utilize bacterial peptide transporters, rapid intrabacterial hydrolysis surprisingly turns out to be a major factor for boosting the efficacy of these antibiotic prodrugs. This result indicates that rapid intrabacterial hydrolysis may act as a useful approach for countering bacterial efflux pumps (Li et al., "The Challenge of Efflux-mediated Antibiotic Resistance in Gram-negative Bacteria," *Clin. Microbiol. Rev.* 28:337-418 (2015), which is hereby incorporated by reference in its entirety) or other bacterial machineries (Salomon et al., "Type VI Secretion System," *Curr. Biol* 25:R265-R266 (2015), which is hereby incorporated by reference in its entirety), which warranted further investigation in the examples below. Besides underscoring the versatile applications of intracellular enzymatic reactions, this work demonstrated that conjugation of peptides to drugs is a powerful way for developing new therapeutics.

Materials and Methods for Examples 6-12

General. 2-Chlorotrityl chloride resin (1.0-1.2 mmol/g), HBTU, and Fmoc protected amino acids were purchased from GL Biochem (Shanghai, China). Other chemical reagents and solvents were purchased from Fisher Scientific. Dulbecco's Modified Eagle Medium (DMEM), fetal bovine serum (FBS), and Gibco Penicillin-Streptomycin were purchased from Life Technologies. All precursors were purified with Agilent 1100 Series Liquid Chromatograph system, equipped with an XTerra C18 RP column and Variable Wavelength Detector. The LC-MS spectra were obtained with a Waters Acquity Ultra Performance LC with Waters MICROMASS detector.

Experimental materials and instruments: All the solvents and chemical reagents were used directly as received from the commercial sources without further purification unless otherwise stated. Porcine liver esterase (PLE) was purchased from Sigma-Aldrich (lyophilized powder, >15 units/mg solid; Unit definition: One unit will hydrolyze 1.0 μmole of ethyl butyrate to butyric acid and ethanol per minute at pH 8.0 at 25° C.). All conjugates were purified with Agilent 1100 Series Liquid Chromatography system, equipped with an XTerra C18 RP column and Variable Wavelength detector. The LC-MS spectra were obtained with a Waters Acquity Ultra Performance LC with Waters MICROMASS detector. $^{1}H$ NMR spectra were obtained on Varian Unity Inova 400, and TEM images on a Morgagni 268 transmission electron microscope.

Hydrolysis assay: Wild-type *E. coli* strains (K12) were harvested by centrifugation and the cell pellets were lysed using a sonic device. After centrifugation, the supernatant was collected and the proteinase inhibitor was added in the *E. coli* lysate. The concentration of *E. coli* lysate was normalized by the fluorescence intensity of 5-carboxyfluorescein diacetate (CFDA). Briefly, different concentrations of CES (4 U/mL, 2 U/mL, 1 U/mL, 0.5 U/mL, 0.25 U/mL, 0.125 U/mL, 0.0625 U/mL, 0.03125 U/mL, 0.015625 U/mL and 0 U/mL) and different amount of *E. coli* lysates were prepared in PBS buffer. Followed by, 25 μM of CFDA was added in and incubated at room temperature for 1 hour. Then the fluorescence was tested to draw a fluorescence-concentration dependent curve for figuring out the concentration of *E. coli* lysates. Solutions of CLsuGG (200 μM) were prepared in pH 7.4 PBS buffer. CES and *E. coli* lysate (0.1 U/mL) were added and incubated with above solutions at 37° C. for 24 hours. At different time points, the solution was taken out, extracted with an equal volume of butanol, concentrated to dryness, and resuspended with butanol for HPLC analysis.

Transmission electron microscopy (TEM) sample preparation: A negative staining technique was used to study the TEM images. Applicant first glow discharged the 400 mesh copper grids coated with continuous thick carbon film (~35 nm) prior to use to increase the hydrophilicity. After loading samples (7 μL) on the grid, the grid was rinsed with dd-water for twice or three times. Immediately after rinsing, the grid containing sample was stained with 2.0% w/v uranyl acetate for three times. Afterwards, the grid was allowed to dry in air.

Light scattering sample preparation: The static light scattering experiments were performed by using an ALV (Langen, Germany) goniometer and correlator system with a 22 mW HeNe (λ=633 nm) laser and an avalanche photodiode detector. All samples were dissolved in PBS buffer. The addition of PLE to the solution of the conjugates for 24 hours allowed corresponding enzymatic hydrolyzed samples to be obtained. The SLS tests were carried out at room temperature, and the angles of light scattering we chose were 30°, 60°, 90° and 120°, respectively. The resulting intensity ratios are proportional to the amount of aggregates in the samples.

Bacteria culture and inhibitory activity assay: Single esterase (bioH, frsA, ybfF, yfbB, yqiA, yeiG, or ypfH) deletion mutants, bacterial transporter (ydgR, fepA and ompF) deletion mutants and the efflux pump (acrA) deletion mutant were all purchased from Dharmacon Horizon Discovery (Cambridge, United Kingdom). The K12 wild-type *E. coli* strain (MG1655) was cultured in autoclaved LB medium (25 g/L LB broth/water) in a shaker-incubator overnight to stationary growth phase, and then sub-cultured in the same medium after dilution to $OD_{600}$ of 0.05. Compounds were added at different concentrations. The mixture of bacteria and compounds were placed (200 μL/well) into 96-well clear flat bottom plates. In all plates, the $OD_{600}$ was measured before and after a 16 hour incubation at 37° C. (Ghafourian et al., "Extended Spectrum Beta-Lactamases: Definition, Classification and Epidemiology," *Curr. Issues Mol. Biol.* 17 (1):11-22 (2014), which is hereby incorporated by reference in its entirety).

Cell culture and cell viability assays: All cell lines were purchased from the American Type Culture Collection (ATCC, Manassas, VA, USA). The HS-5 cells were propagated in Dulbecco's Modified Eagle's Medium (DMEM) supplemented with 10% fetal bovine serum (FBS) and 1% antibiotics in a fully humidified incubator containing 5% $CO_2$ at 37° C., HepG2 and HEK293 cells in Eagle's Minimum Essential Media (MEM) supplemented with 10% FBS and 1% antibiotics in a fully humidified incubator containing 5% $CO_2$ at 37° C. Cells in exponential growth phase were seeded in a 96 well plate at a concentration of $1\times10^4$ cell/well, and were allowed to attach to the well for 24 hours at 37° C., 5% $CO_2$. The culture medium was removed and 100 μL culture medium containing corresponding compounds (immediately diluted from fresh prepared stock solution) at gradient concentrations (0 μM as the control) was placed into each well. After culturing at 37° C., 5% $CO_2$ for 24 hours, 48 hours, and 72 hours, each well was added with 10 μL of 5 mg/mL MTT ((3-(4,5-dimethylthiazol-2-yl)-2,5-diphenyltetrazolium bromide), and the plated cells were incubated at dark for 4 hours. 100 μL 10% SDS with 0.01M HCl was added to each well to stop the reduction and to dissolve the purple. After incubation of the cells at 37° C. for overnight, the OD at 595 nm of the solution was measured in a microplate reader. Data represent the mean±standard deviation of three independent experiments.

Example 6—Molecular Design of CLsuGG Analogues

The peptide conjugated chloramphenicol was designed in a straightforward manner for easy production and convenient optimization. As shown in Table 4, the conjugates have a general formula of antibiotic—succinate—peptide (or amino acid). The peptides fall into three main categories: a variety of neutral peptides (1a-1q), from dipeptides to pentapeptides, for studying the influence of numbers of same amino acid residues or the side chains of the amino acid residues on the activity; charged peptides (e.g., arginine, lysine, glutamic acid, or aspartic acid (2a-2j)) for investigating the effect of charges; and naphthyl containing peptides (3a-3c) for understanding the roles of strong hydrophobicity. Besides peptide conjugates, there are conjugates bearing a single amino acid (4a), or only capping the C-terminal of CLsu using a methyl (4b), sulfate (4c), or phosphate (4d) group. Moreover, considering the stereochemistry of the peptides as a determining factor for biological activities, D-peptide conjugates were generated in the first two categories (e.g., 1g, 1i, 2b, and 2h).

TABLE 4
Structures of Chloramphenicol (CL), Chloramphenicol Succinate (CLsu), and Peptide-Conjugated Prodrugs
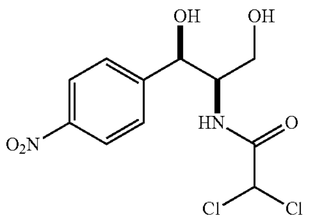
CL
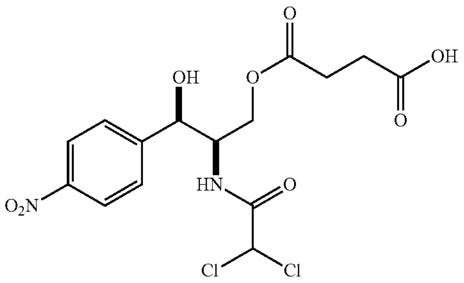
CLsu
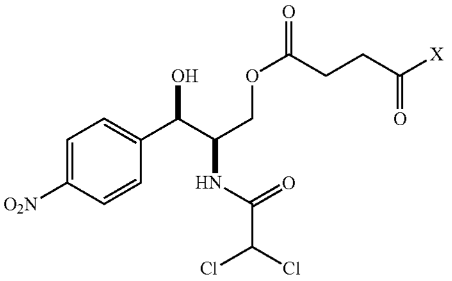
| # | X |
|---|---|
| 1a | 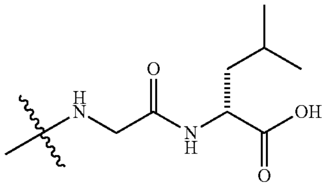 [SMILES: *NCC(=O)N[C@H](CC(C)C)C(=O)O] |
| 1b | 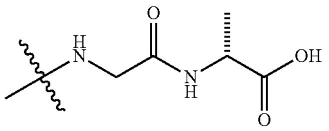 [SMILES: *NCC(=O)N[C@H](C)C(=O)O] |
| 1c | 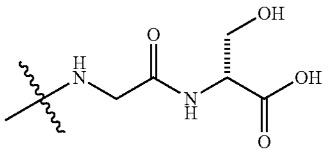 [SMILES: *NCC(=O)N[C@H](CO)C(=O)O] |
| 1d | 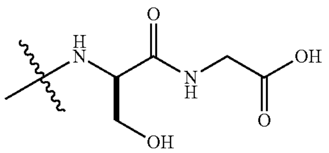 [SMILES: *N[C@H](CO)C(=O)NCC(=O)O] |

TABLE 4-continued
1e
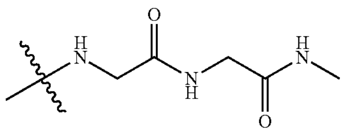 [SMILES: *NCC(=O)NCC(=O)NC]
1f
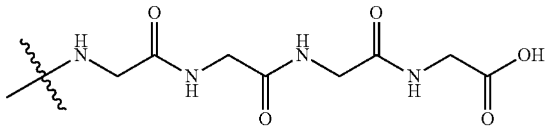 [SMILES: *NCC(=O)NCC(=O)NCC(=O)NCC(=O)O]
1g
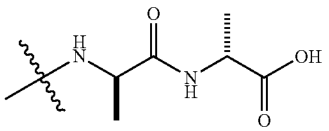 [SMILES: *N[C@H](C)C(=O)N[C@H](C)C(=O)O]
1h
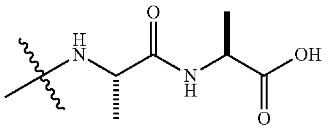 [SMILES: *N[C@@H](C)C(=O)N[C@@H](C)C(=O)O]
1i
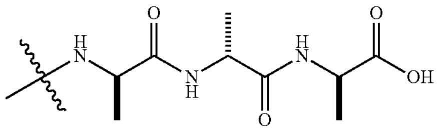 [SMILES: *N[C@H](C)C(=O)N[C@H](C)C(=O)N[C@H](C)C(=O)O]
1j
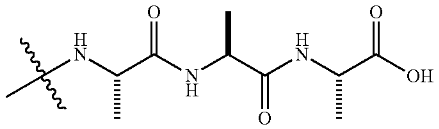 [SMILES: *N[C@@H](C)C(=O)N[C@@H](C)C(=O)N[C@@H](C)C(=O)O]
1k
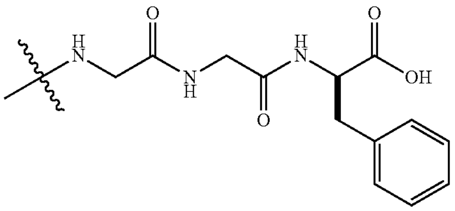 [SMILES: *NCC(=O)NCC(=O)N[C@H](Cc1ccccc1)C(=O)O]
1l
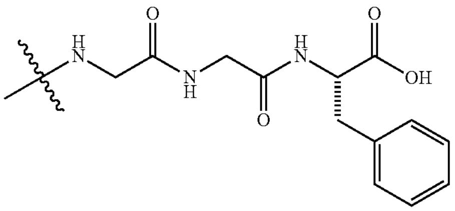 [SMILES: *NCC(=O)NCC(=O)N[C@@H](Cc1ccccc1)C(=O)O]
1m
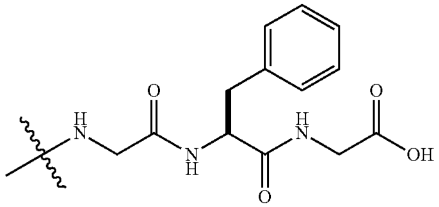 [SMILES: *NCC(=O)N[C@@H](Cc1ccccc1)C(=O)NCC(=O)O]

TABLE 4-continued
1n
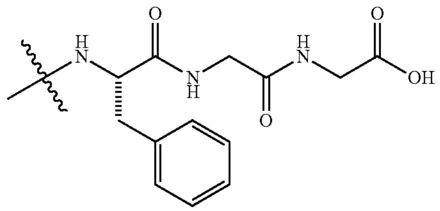 [SMILES: *N[C@@H](Cc1ccccc1)C(=O)NCC(=O)NCC(=O)O]
1o
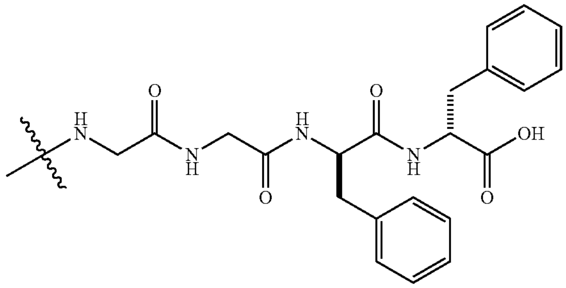 [SMILES: *NCC(=O)NCC(=O)N[C@H](Cc1ccccc1)C(=O)N[C@H](Cc1ccccc1)C(=O)O]
1p
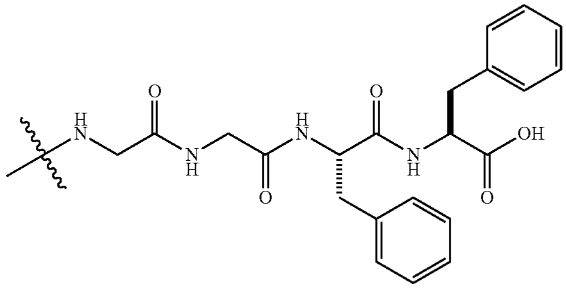 [SMILES: *NCC(=O)NCC(=O)N[C@@H](Cc1ccccc1)C(=O)N[C@@H](Cc1ccccc1)C(=O)O]
1q
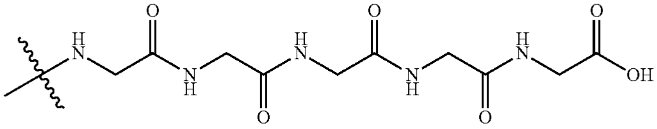 [SMILES: *NCC(=O)NCC(=O)NCC(=O)NCC(=O)NCC(=O)O]
2a
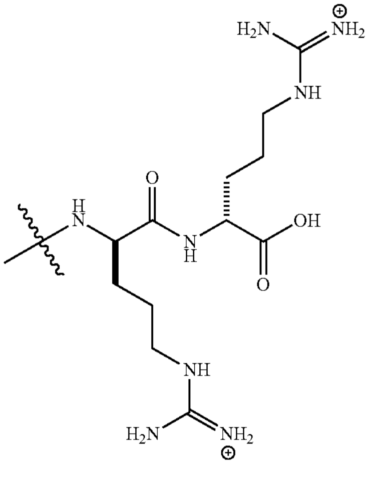 [SMILES: *N[C@H](CCCNC(N)=[NH2+])C(=O)N[C@H](CCCNC(N)=[NH2+])C(=O)O]

TABLE 4-continued
2b
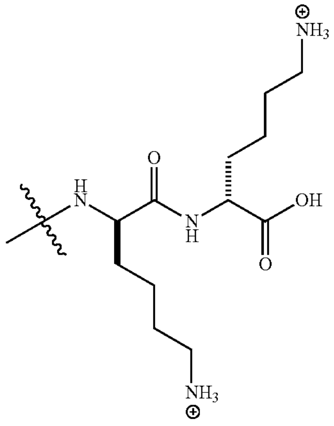 [SMILES: *N[C@H](CCCC[NH3+])C(=O)N[C@H](CCCC[NH3+])C(=O)O]
2c
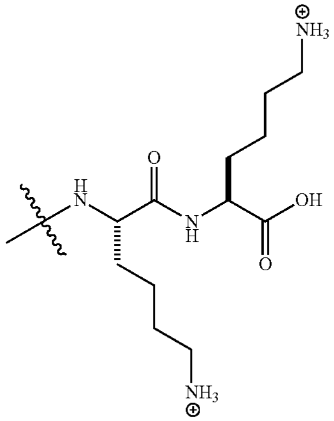 [SMILES: *N[C@@H](CCCC[NH3+])C(=O)N[C@@H](CCCC[NH3+])C(=O)O]
2d
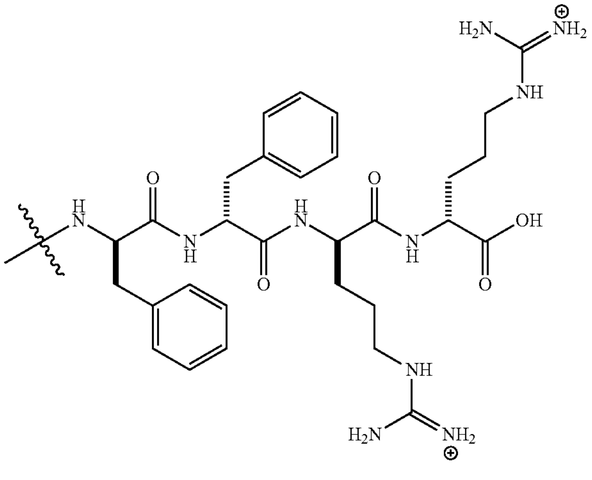 [SMILES: *N[C@H](Cc1ccccc1)C(=O)N[C@H](Cc1ccccc1)C(=O)N[C@H](CCCNC(N)=[NH2+])C(=O)N[C@H](CCCNC(N)=[NH2+])C(=O)O]

TABLE 4-continued
2e
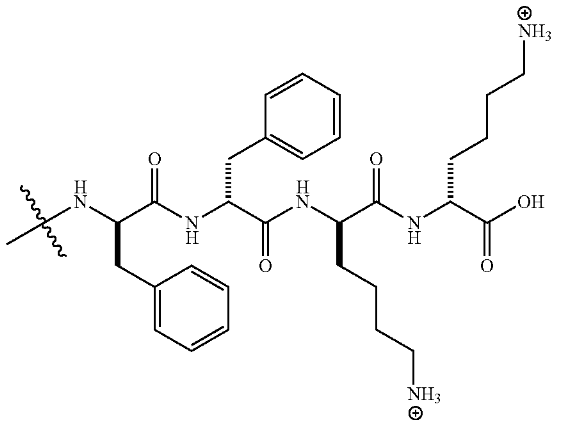 [SMILES: *N[C@H](Cc1ccccc1)C(=O)N[C@H](Cc1ccccc1)C(=O)N[C@H](CCCC[NH3+])C(=O)N[C@H](CCCC[NH3+])C(=O)O]
2f
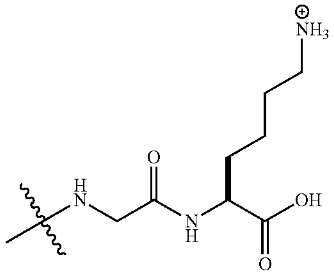 [SMILES: *NCC(=O)N[C@@H](CCCC[NH3+])C(=O)O]
2g
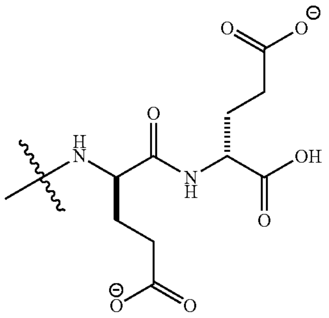 [SMILES: *N[C@H](CCC(=O)[O-])C(=O)N[C@H](CCC(=O)[O-])C(=O)O]
2h
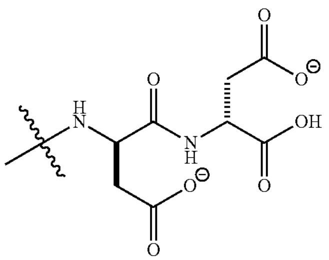 [SMILES: *N[C@H](CC(=O)[O-])C(=O)N[C@H](CC(=O)[O-])C(=O)O]
2i
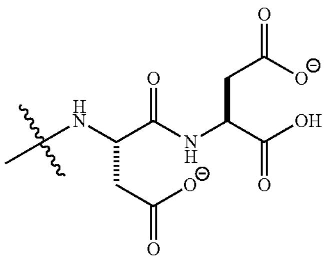 [SMILES: *N[C@@H](CC(=O)[O-])C(=O)N[C@@H](CC(=O)[O-])C(=O)O]

TABLE 4-continued
| | |
|---|---|
| 2j | 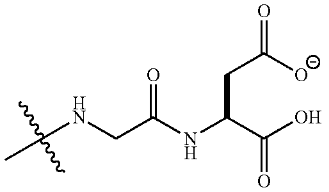 [SMILES: *NCC(=O)N[C@@H](CC(=O)[O-])C(=O)O] |
| 3a | 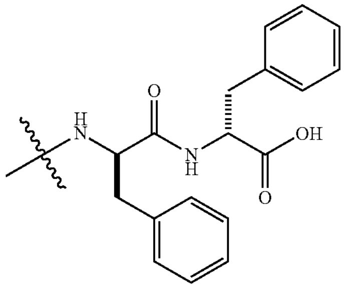 [SMILES: *N[C@H](Cc1ccccc1)C(=O)N[C@H](Cc1ccccc1)C(=O)O] |
| 3b | 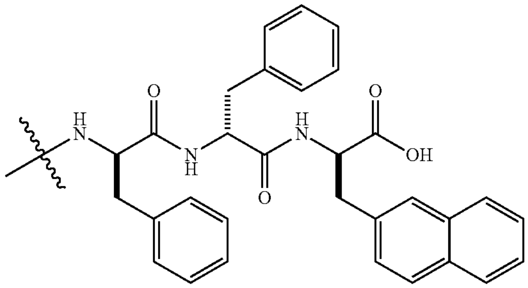 [SMILES: *N[C@H](Cc1ccccc1)C(=O)N[C@H](Cc1ccccc1)C(=O)N[C@H](Cc1ccc2ccccc2c1)C(=O)O] |
| 3c | 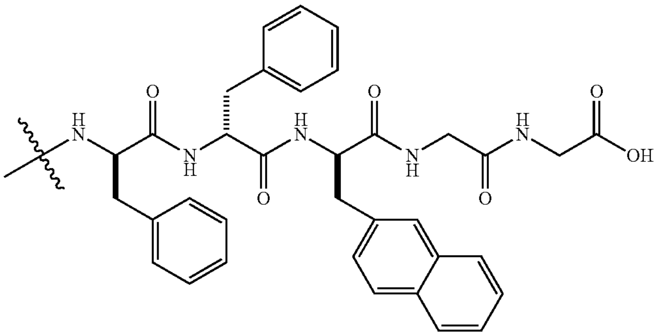 [SMILES: *N[C@H](Cc1ccccc1)C(=O)N[C@H](Cc1ccccc1)C(=O)N[C@H](Cc1ccc2ccccc2c1)C(=O)NCC(=O)NCC(=O)O] |
| 4a | 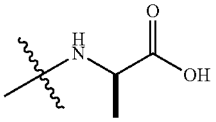 [SMILES: *N[C@H](C)C(=O)O] |
| 4b | 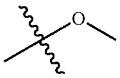 |
| 4c | 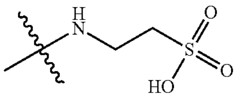 [SMILES: *NCCS(=O)(=O)O] |
| 4d | 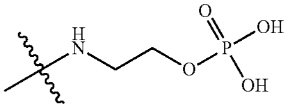 [SMILES: *NCCOP(=O)(O)O] |

Figure 7:
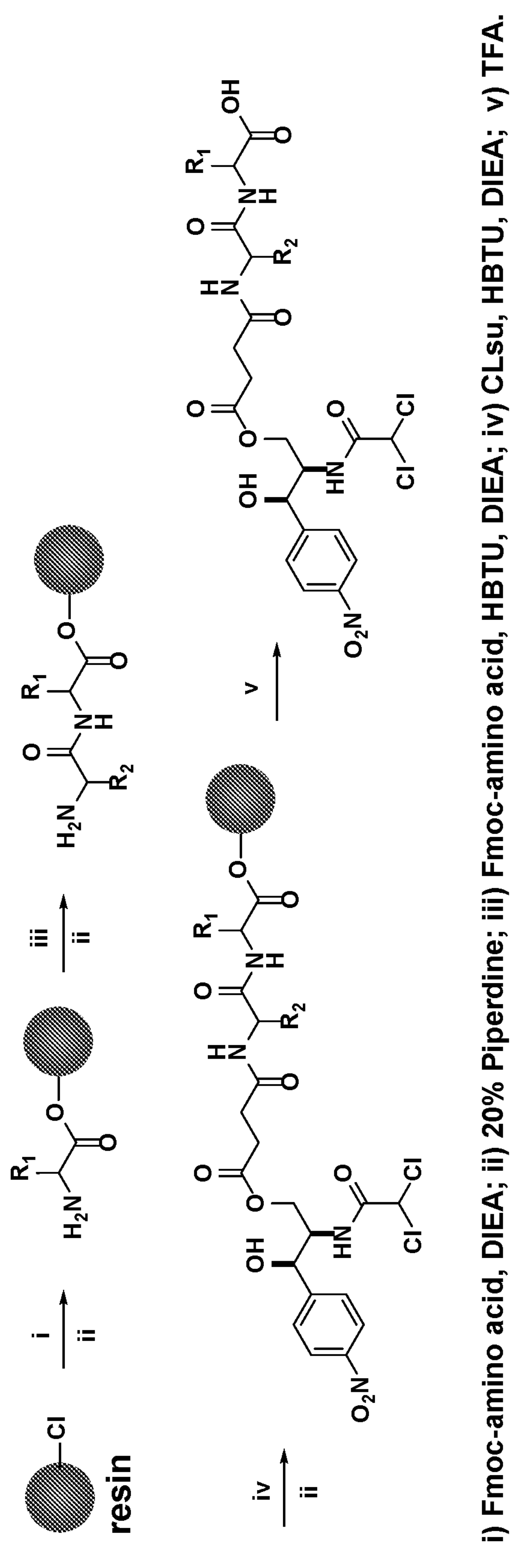
FIG. 7 is a reaction scheme showing the synthesis of peptide conjugated chloramphenicol by solid phase peptide synthesis using chloramphenicol succinate reaction with resin-bound di-, tri-, tetra-, or penta-peptides (1a-1q, 2a-2j, 3a-3c, and 4a) whose structures are shown in Table 4.

Example 7—Synthesis of Chloramphenicol (CL), Chloramphenicol Succinate (CLsu), and Peptide-Conjugated Prodrugs As discussed in Examples 1-2 and shown in FIGS. 2A-2C, as well as FIG. 7, the commercially available chloramphenicol succinate sodium, after acidification, is suitable for solid phase peptide synthesis to produce peptide-conjugated analogues of CLsuGG that are designated as 1a-1q, 2a-2j, 3a-3c, and 4a as shown in Table 4 above. Briefly, chloramphenicol succinate sodium (150 mg) was dissolved in distilled water (3 mL), and HCl (1 M) was added dropwise until the pH of the mixture was adjusted to 2.0. The precipitate was washed several times with distilled water and dried for further use.

Solid phase peptide synthesis (Chan & White, "Fmoc Solid Phase Peptide Synthesis: A Practical Approach," Oxford: Oxford University Press: 20001, which is hereby incorporated by reference in its entirety) was used for the synthesis of all peptide-conjugated prodrugs. 2-chlorotrityl chloride resin (500 mg, 0.5 mmol) was swelled in 10 mL of DCM for 20 minutes. The attachment of the first Fmoc protected amino acid (0.5 mmol) to the resin was achieved by adding N,N-diisopropylethylamine (DIPEA) (413 μL, 2.5 mmol) to the beads in the reaction vessel, which was allowed to shake at room temperature for 1 hour. After that, the reaction solution was drained, followed by washing with DMF (10 mL×3) and DCM (10 mL×3). The unreacted 2-chlorotrityl chloride moieties were capped with a solution of methanol/DIPEA/DCM (v/v/v: 3/1/16) for 30 minutes. The beads were washed with DMF (10 mL×3). The Fmoc group was removed by treating beads with 20% piperidine/DMF (v/v) solution for 20 minutes at room temperature. The solution was drained and washed with DMF (10 mL×3). The beads were reacted with the next Fmoc protected amino acid or CLsu (0.5 mmol) by adding HBTU (190 mg, 0.5 mmol) and N,N-diisopropylethylamine (DIPEA) (413 μL, 2.5 mmol) to the beads in the reaction vessel, which was allowed to shake at room temperature for 1 hour, and the solution was drained. Then the product was cleaved from resin with 10 mL of trifluoroacetic acid for 2 hours. The solution was collected, and the remaining beads were washed with 5 mL of trifluoroacetic acid three times. All the solution was combined and trifluoroacetic acid was removed with the $N_2$ flow. The residue was then precipitated with diethyl ether. The crude product was purified by reverse phase HPLC using HPLC grade acetonitrile and water with supplement of 0.1% trifluoroacetic acid as the eluents.

To form 1e, CLsuGG (134.02 mg, 0.25 mmol), methylamine hydrochloride (25.32 mg, 0.375 mmol), HBTU (104.3 mg, 0.275 mmol), and DIEA (80.78 mg, 0.625 mmol) were dissolved in DMF (2 mL) and then stirred overnight at room temperature. Next, the solvent was removed and 1e was purified by reverse hase HPLC using HPLC grade acetonitrile and water with supplement of 0.1% trifluoroacetic acid as the eluents.

Figure 8:
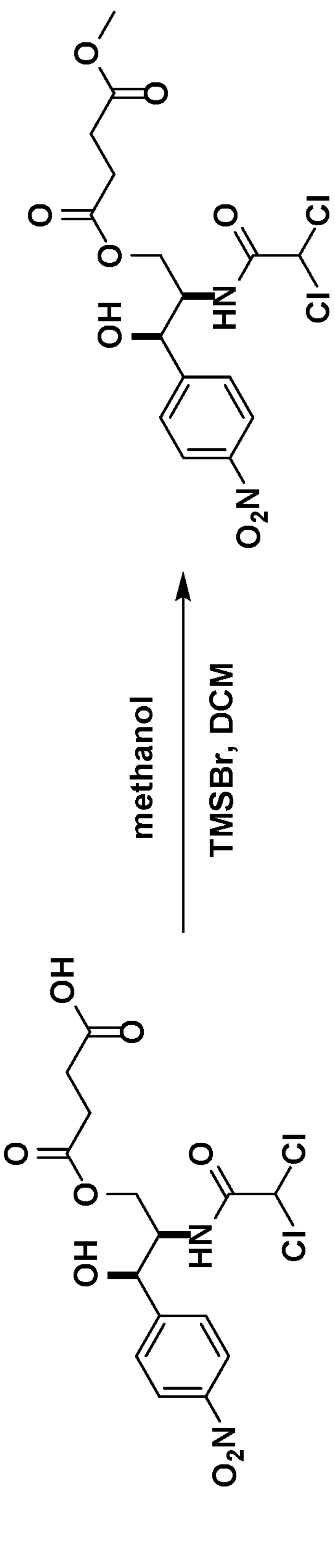
FIG. 8 is a reaction scheme showing the synthesis of CLsu-OMe (4b).

Solution phase synthesis was used to prepare 4b-4d as follows:

Synthesis of compound 4b: CLsu was dissolved in DCM. After that, bromotrimethylsilane (TMSBr) was added dropwise to afford compound 4b, which was purified by reversed phase HPLC using HPLC grade acetonitrile and water with supplement of 0.1% trifluoroacetic acid as the eluents (FIG. 8).

Figure 9:
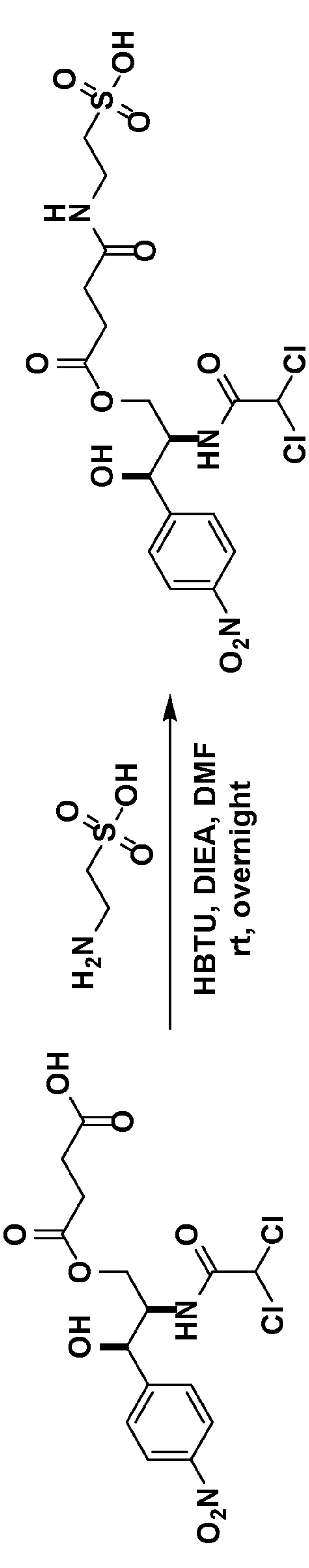
FIG. 9 is a reaction scheme showing the synthesis of CLsu-Tau (4c).

Synthesis of compound 4c: CLsu (0.1 mmol), HBTU (0.11 mmol) and DIEA (0.5 mmol) were dissolved in DMF (1 mL) (FIG. 9). The mixture was stirred at room temperature for 30 minutes. Followed by, taurine (0.2 mmol) was added to the stirring mixture and stirred continually at room temperature for overnight (FIG. 9). The solvent was removed by air dry, and then final product was purified by reversed phase HPLC using HPLC grade acetonitrile and water with supplement of 0.1% trifluoroacetic acid as the eluents.

Figure 10:
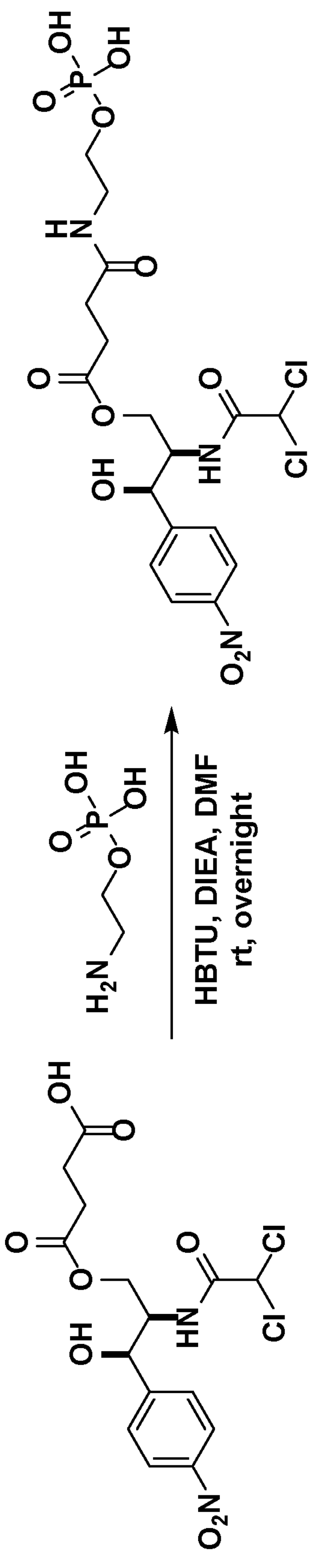
FIG. 10 is a reaction scheme showing the synthesis of CLsu-ep (4d).

Synthesis of compound 4d: CLsu (0.1 mmol), HBTU (0.11 mmol) and DIEA (0.5 mmol) were dissolved in DMF (1 mL) (FIG. 10). The mixture was stirred at room temperature for 30 minutes. Followed by, o-phosphorylethanolamine (0.2 mmol) was added to the stirring mixture and stirred continually at room temperature for overnight (FIG. 10). The solvent was removed by air dry, and then final product was purified by reversed phase HPLC using HPLC grade acetonitrile and water with supplement of 0.1% trifluoroacetic acid as the eluents.

The purity of the compounds was determined to be >95% by LC-MS with a Waters Acquity Ultra Performance LC (Table 5).

TABLE 5

LC-MS Purities of Compounds 1a-4d

| Compound | Purity (based on LC-MS) (%) | Retention time (min) | Calculated mass | Observed mass |
|---|---|---|---|---|
| 1a | 95.33 | 2.02 | 592.13 | 591.27 |
| 1b | 98.80 | 1.74 | 550.09 | 549.28 |
| 1c | 95.21 | 1.64 | 566.08 | 565.27 |
| 1d | 97.16 | 1.60 | 566.08 | 565.27 |
| 1e | 95.86 | 1.60 | 549.10 | 548.20 |
| 1f | 99.29 | 1.77 | 650.11 | 649.20 |
| 1g | 97.86 | 1.80 | 564.10 | 563.35 |
| 1h | 98.64 | 1.77 | 564.10 | 563.06 |
| 1i | 98.41 | 1.77 | 635.14 | 634.30 |
| 1j | 96.19 | 1.74 | 635.14 | 634.30 |
| 1k | 95.45 | 2.10 | 683.14 | 682.30 |
| 1l | 94.90 | 2.01 | 683.14 | 682.39 |
| 1m | 96.89 | 2.01 | 683.14 | 682.17 |
| 1n | 97.54 | 2.08 | 683.14 | 682.30 |
| 1o | 97.62 | 2.25 | 830.21 | 829.29 |
| 1p | 98.76 | 2.27 | 830.21 | 829.29 |
| 1q | 99.70 | 1.63 | 707.14 | 706.22 |
| 2a | 94.89 | 1.18 | 736.25 | 733.43 |
| 2b | 97.50 | 1.06 | 680.23 | 677.27 |
| 2c | 95.91 | 1.11 | 680.23 | 677.42 |
| 2d | 97.60 | 1.87 | 1030.38 | 1027.59 |
| 2e | 99.50 | 1.64 | 974.37 | 971.37 |
| 2f | 97.60 | 1.38 | 608.15 | 606.33 |
| 2g | 97.74 | 1.66 | 680.11 | 679.23 |
| 2h | 99.26 | 1.63 | 652.08 | 651.15 |
| 2i | 99.60 | 1.62 | 652.08 | 651.25 |
| 2j | 97.22 | 1.66 | 594.08 | 593.32 |
| 3a | 98.28 | 2.47 | 716.17 | 715.39 |
| 3b | 98.33 | 2.82 | 913.25 | 912.45 |
| 3c | 97.26 | 2.60 | 1027.29 | 1026.49 |
| 4a | 97.64 | 1.84 | 493.07 | 492.29 |
| 4b | 98.94 | 2.18 | 436.04 | 435.15 |
| 4c | 95.79 | 1.50, 1.57, 1.62 | 529.03 | 528.25 |
| 4d | 97.21 | 1.47 | 545.04 | 544.24 |

Subsequently, the structure of the intermediates and prodrugs was confirmed by $^{1}H$ NMR and $^{13}C$ NMR spectra as follows:

Compound 1a. $^{1}H$ NMR (400 MHz, DMSO-$d_6$, 25° C., ppm): δ 8.51 (d, J=8.0 Hz, 1H), 8.16 (m, 3H), 8.04 (d, J=8.0 Hz, 1H), 7.64 (d, J=8.0 Hz, 2H), 6.44 (m, 1H), 5.03 (s, 1H), 4.22 (m, 3H), 4.08 (m, 2H), 3.73 (m, 2H), 2.44 (m, 4H), 1.56 (m, 3H), 0.84 (m, 6H); $^{13}C$ NMR (100 MHz, DMSO-$d_6$, 25° C., ppm): δ 174.34 (CO carboxyl), 172.63 (CO carboxyl), 171.47 (CONH amide), 169.26 (CONH amide), 164.02

(CONH chloramphenicol), 150.65 (CCH phenyl), 146.99 ($CNO_2$ phenyl), 127.87 (CH phenyl), 123.30 (CH phenyl), 69.85 (CH chloramphenicol), 66.67 (CH chloramphenicol), 63.38 ($CH_2$ chloramphenicol), 53.90 (CH), 50.25 ($CH_2$), 42.08 ($CH_2$), 30.05 ($CH_2$), 29.33 ($CH_2$), 24.61 ($CH_2$), 23.19 (CH), 21.73 ($CH_3$); ESI-MS m/z calcd. for $C_{23}H_{30}Cl_2N_4O_{10}$ [M]+: m/z=592.13, found $[M-H]^-$ 591.27.

Compound 1b. $^1H$ NMR (400 MHz, DMSO-$d_6$, 25° C., ppm): δ 8.51 (d, J=12.0 Hz, 1H), 8.16 (m, 3H), 8.10 (d, J=8.0 Hz, 1H), 7.64 (d, J=8.0 Hz, 2H), 6.44 (s, 1H), 5.03 (s, 1H), 4.20 (m, 3H), 4.09 (m, 2H), 3.72 (m, 2H), 2.45 (m, 4H), 1.25 (d, J=8.0 Hz, 3H); $^{13}C$ NMR (100 MHz, DMSO-$d_6$, 25° C., ppm); $^{13}C$ NMR (100 MHz, DMSO-$d_6$, 25° C., ppm): δ 174.38 (CO carboxyl), 172.66 (CO carboxyl), 171.51 (CONH amide), 169.04 (CONH amide), 164.05 (CONH chloramphenicol), 150.67 (CCH phenyl), 147.02 ($CNO_2$ phenyl), 127.89 (CH phenyl), 123.33 (CH phenyl), 69.88 (CH chloramphenicol), 66.70 (CH chloramphenicol), 63.42 ($CH_2$ chloramphenicol), 53.91 (CH, chloramphenicol), 47.84 (CH), 42.11 ($CH_2$), 30.07 ($CH_2$), 29.35 ($CH_2$), 17.63 ($CH_3$); ESI-MS m/z calcd. for $C_{20}H_{24}Cl_2N_4O_{10}$ [M]+: m/z=550.09, found $[M-H]^-$ 549.28.

Compound 1c. $^1H$ NMR (400 MHz, DMSO-$d_6$, 25° C., ppm): δ 12.63 (s, 1H), 8.51 (d, J=8.0 Hz, 1H), 8.15 (m, 3H), 7.99 (d, J=8.0 Hz, 1H), 7.63 (d, J=12.0 Hz, 2H), 6.44 (s, 1H), 6.20 (s, 1H), 5.02 (s, 1H), 4.24 (m, 3H), 4.09 (m, 1H), 3.77 (m, 2H), 3.69 (m, 1H), 3.60 (m, 1H), 2.43 (m, 4H); $^{13}C$ NMR (100 MHz, DMSO-$d_6$, 25° C., ppm); $^{13}C$ NMR (100 MHz, DMSO-$d_6$, 25° C., ppm): δ 172.58 (CO carboxyl), 172.23 (CO carboxyl), 171.46 (CONH amide), 169.34 (CONH amide), 164.04 (CONH chloramphenicol), 150.66 (CCH phenyl), 147.01 ($CNO_2$ phenyl), 127.88 (CH phenyl), 123.32 (CH phenyl), 69.88 (CH chloramphenicol), 66.69 (CH chloramphenicol), 63.44 ($CH_2$ chloramphenicol), 61.72 ($CH_2$), 54.95 (CH), 53.92 (CH, chloramphenicol), 42.17 ($CH_2$), 30.07 ($CH_2$), 29.36 ($CH_2$); ESI-MS m/z calcd. for $C_{20}H_{24}Cl_2N_4O_{11}$ [M]+: m/z=566.08, found $[M-H]^-$ 565.27.

Compound 1d. $^1H$ NMR (400 MHz, DMSO-$d_6$, 25° C., ppm): δ 8.53 (m, 1H), 8.15 (m, 3H), 8.01 (m, 1H), 7.64 (m, 2H), 6.43 (m, 1H), 5.03 (d, J=8.0 Hz, 1H), 4.22 (m, 6H), 3.73 (m, 2H), 3.57 (m, 2H), 2.48 (m, 4H)(FIG. 10D); $^{13}C$ NMR (100 MHz, DMSO-$d_6$, 25° C., ppm): δ 172.70 (CO carboxyl), 171.49 (CO carboxyl), 171.38 (CONH amide), 170.83 (CONH amide), 164.04 (CONH chloramphenicol), 150.67 (CCH phenyl), 147.01 ($CNO_2$phenyl), 127.89 (CH phenyl), 123.32 (CH phenyl), 69.85 (CH chloramphenicol), 66.69 (CH chloramphenicol), 63.38 ($CH_2$ chloramphenicol), 62.16 ($CH_2$), 55.49 (CH), 53.90 (CH, chloramphenicol), 41.12 ($CH_2$), 30.15 ($CH_2$), 29.35 ($CH_2$); ESI-MS m/z calcd. for $C_{20}H_{24}Cl_2N_4O_{11}$ [M]+: m/z=566.08, found $[M-H]^-$ 565.27.

Compound 1e. $^1H$ NMR (400 MHz, DMSO-$d_6$, 25° C., ppm): δ 8.51 (d, J=8.0 Hz, 1H), 8.22 (m, 1H), 8.17 (d, J=8.0 Hz, 2H), 8.11 (m, 1H), 7.63 (d, J=8.0 Hz, 2H), 6.44 (s, 1H), 5.02 (s, 1H), 4.21 (m, 2H), 4.09 (m, 1H), 3.72 (m, 3H), 3.63 (d, J=4.0 Hz, 1H), 2.57 (d, J=4.0 Hz, 2H), 2.45 (d, 4H); $^{13}C$ NMR (100 MHz, DMSO-$d_6$, 25° C., ppm): δ 172.63 (CO carboxyl), 171.90 (CO carboxyl), 171.53 (CONH amide), 169.69 (CONH amide), 164.05 (CONH chloramphenicol), 150.66 (CCH phenyl), 147.02 ($CNO_2$phenyl), 127.88 (CH phenyl), 123.33 (CH phenyl), 69.89 (CH chloramphenicol), 66.70 (CH chloramphenicol), 63.48 ($CH_2$ chloramphenicol), 53.93 (CH, chloramphenicol), 49.02 ($CH_2$), 42.42 ($CH_2$), 30.08 ($CH_2$), 29.32 ($CH_2$), 25.86 ($CH_3$); ESI-MS m/z calcd. for $C_{20}H_{25}Cl_2N_5O_9$ [M]+: m/z=549.10, found $[M-H]^-$ 548.20.

Compound 1f. $^1H$ NMR (400 MHz, DMSO-$d_6$, 25° C., ppm): δ 8.51 (d, J=8.0 Hz, 1H), 8.16 (m, 6H), 7.63 (d, J=8.0 Hz, 2H), 6.44 (s, 1H), 5.02 (s, 1H), 4.20 (m, 2H), 4.09 (m, 2H), 3.74 (dd, J=4.0, 8.0 Hz, 8H), 2.46 (m, 4H); $^{13}C$ NMR (100 MHz, DMSO-$d_6$, 25° C., ppm): δ 172.71 (CO carboxyl), 171.82 (CO carboxyl), 171.58 (CONH amide), 169.90 (CONH amide), 169.62 (CONH amide), 164.14 (CONH chloramphenicol), 150.75 (CCH phenyl), 147.10 ($CNO_2$ phenyl), 127.97 (CH phenyl), 123.42 (CH phenyl), 69.98 (CH chloramphenicol), 66.78 (CH chloramphenicol), 63.55 ($CH_2$ chloramphenicol), 54.02 (CH chloramphenicol), 42.65 ($CH_2$), 42.51 ($CH_2$), 42.24 ($CH_2$), 41.07 ($CH_2$), 30.16 ($CH_2$), 29.40 ($CH_2$); ESI-MS m/z calcd. for $C_{23}H_{28}Cl_2N_6O_{12}$ [M]+: m/z=650.11, found $[M-H]^-$ 649.20.

Compound 1g. $^1H$ NMR (400 MHz, DMSO-$d_6$, 25° C., ppm): δ 8.51 (d, J=8.0 Hz, 1H), 8.17 (d, J=12.0 Hz, 2H), 8.13 (d, J=8.0 Hz, 1H), 8.07 (d, J=8.0 Hz, 1H), 7.64 (d, J=8.0 Hz, 2H), 6.44 (s, 1H), 5.03 (s, 1H), 4.31 (m, 1H), 4.17 (m, 3H), 4.09 (m, 1H), 2.44 (m, 4H), 1.23 (d, J=4.0 Hz, 3H), 1.19 (d, J=8.0 Hz, 3H); $^{13}C$ NMR (100 MHz, DMSO-$d_6$, 25° C., ppm): δ 174.50 (CO carboxyl), 172.76 (CO carboxyl), 172.66 (CONH amide), 170.94 (CONH amide), 164.13 (CONH chloramphenicol), 150.79 (CCH phenyl), 147.11 ($CNO_2$phenyl), 128.00 (CH phenyl), 123.43 (CH phenyl), 69.91 (CH chloramphenicol), 66.79 (CH chloramphenicol), 63.38 ($CH_2$ chloramphenicol), 53.97 (CH chloramphenicol), 48.29 (CH), 47.88 (CH), 30.12 ($CH_2$), 29.41 ($CH_2$), 18.72 ($CH_3$), 17.54 ($CH_3$); ESI-MS m/z calcd. for $C_{21}H_{26}Cl_2N_4O_{10}$ [M]+: m/z=564.10, found $[M-H]^-$ 563.35.

Compound 1h. $^1H$ NMR (400 MHz, DMSO-$d_6$, 25° C., ppm): δ 8.51 (d, J=12.0 Hz, 1H), 8.17 (d, J=8.0 Hz, 2H), 8.12 (d, J=8.0 Hz, 1H), 8.06 (d, J=8.0 Hz, 1H), 7.64 (d, J=8.0 Hz, 2H), 6.44 (s, 1H), 5.03 (s, 1H), 4.31 (m, 1H), 4.18 (m, 3H), 4.09 (m, 1H), 2.44 (m, 4H), 1.26 (d, J=8.0 Hz, 3H), 1.18 (d, J=8.0 Hz, 3H); $^{13}C$ NMR (100 MHz, DMSO-$d_6$, 25° C., ppm): δ 174.41 (CO carboxyl), 172.61 (CO carboxyl), 172.54 (CONH amide), 170.82 (CONH amide), 164.07 (CONH chloramphenicol), 150.65 (CCH phenyl), 147.02 ($CNO_2$phenyl), 127.89 (CH phenyl), 123.32 (CH phenyl), 69.93 (CH chloramphenicol), 66.70 (CH chloramphenicol), 63.47 ($CH_2$ chloramphenicol), 53.95 (CH chloramphenicol), 48.15 (CH), 47.81 (CH), 30.05 ($CH_2$), 29.36 ($CH_2$), 18.65 ($CH_3$), 17.46 ($CH_3$); ESI-MS m/z calcd. for $C_{21}H_{26}Cl_2N_4O_{10}$ [M]+: m/z=564.10, found $[M-H]^-$ 563.06.

Compound 1i. $^1H$ NMR (400 MHz, DMSO-$d_6$, 25° C., ppm): δ 8.51 (d, J=8.0 Hz, 1H), 8.17 (d, J=8.0 Hz, 2H), 8.12 (d, J=8.0 Hz, 1H), 7.98 (d, J=4.0 Hz, 1H), 7.91 (d, J=8.0 Hz, 1H), 7.64 (d, J=8.0 Hz, 2H), 6.43 (s, 1H), 5.02 (s, 1H), 4.21 (m, 5H), 4.09 (m, 1H), 2.45 (m, 4H), 1.22 (m, 9H); $^{13}C$ NMR (100 MHz, DMSO-$d_6$, 25° C., ppm): δ 174.33 (CO carboxyl), 172.69 (CO carboxyl), 172.28 (CONH amide), 171.14 (CONH amide), 164.02 (CONH chloramphenicol), 150.67 (CCH phenyl), 147.00 ($CNO_2$phenyl), 127.89 (CH phenyl), 123.33 (CH phenyl), 69.84 (CH chloramphenicol), 66.68 (CH chloramphenicol), 63.37 ($CH_2$ chloramphenicol), 53.87 (CH chloramphenicol), 49.01 ($CH_3$ methanol), 48.64 (CH), 48.08 (CH), 47.83 (CH), 30.01 ($CH_2$), 29.29 ($CH_2$), 18.44 ($CH_3$), 17.50 ($CH_3$); ESI-MS m/z calcd. for $C_{24}H_{31}Cl_2N_5O_{11}$ [M]+: m/z=635.14, found $[M-H]^-$ 634.30.

Compound 1j. $^1H$ NMR (400 MHz, DMSO-$d_6$, 25° C., ppm): δ 8.51 (d, J=12.0 Hz, 1H), 8.17 (d, J=8.0 Hz, 2H), 8.11 (d, J=8.0 Hz, 1H), 8.00 (d, J=4.0 Hz, 1H), 7.90 (d, J=8.0 Hz, 1H), 7.63 (d, J=8.0 Hz, 2H), 6.43 (s, 1H), 5.02 (s, 1H), 4.22 (m, 5H), 4.08 (m, 1H), 2.44 (m, 4H), 1.22 (m, 9H); $^{13}C$ NMR (100 MHz, DMSO-$d_6$, 25° C., ppm): δ 174.45 (CO carboxyl), 172.76 (CO carboxyl), 172.40 (CONH amide), 171.26 (CONH amide), 164.18 (CONH chloramphenicol), 150.74 (CCH phenyl), 147.13 ($CNO_2$phenyl), 127.99 (CH phenyl), 123.43 (CH phenyl), 70.07 (CH chloramphenicol), 66.80 (CH chloramphenicol), 63.68 ($CH_2$ chloramphenicol), 54.07 (CH chloramphenicol), 49.12 ($CH_3$ methanol), 48.73 (CH), 48.24 (CH), 47.94 (CH), 30.15 ($CH_2$), 29.44 ($CH_2$), 18.56 ($CH_3$), 17.62 ($CH_3$); ESI-MS m/z calcd. for $C_{24}H_{31}Cl_2N_5O_{11}$ [M]+: m/z=635.14, found $[M-H]^-$ 634.30.

Compound 1k. $^1H$ NMR (400 MHz, DMSO-$d_6$, 25° C., ppm): δ 8.51 (d, J=8.0 Hz, 1H), 8.16 (m, 4H), 8.03 (dd, J=4.0, 8.0 Hz, 1H), 7.63 (d, J=8.0 Hz, 2H), 7.27 (m, 2H), 7.20 (m, 3H), 6.44 (s, 1H), 5.02 (s, 1H), 4.41 (m, 1H), 4.20 (m, 2H), 4.08 (m, 1H), 3.68 (m, 4H), 3.04 (m, 1H), 2.88 (m, 1H), 2.46 (m, 4H); $^{13}C$ NMR (100 MHz, DMSO-$d_6$, 25° C., ppm): δ 173.14 (CO carboxyl), 172.61 (CO carboxyl), 171.71 (CONH amide), 169.56 (CONH amide), 169.05 (CONH amide), 164.05 (CONH chloramphenicol), 150.65 (CCH phenyl), 147.01 ($CNO_2$ phenyl), 137.85 ($CCH_2$ phenyl), 129.52 (CH phenyl), 128.62 (CH phenyl), 127.87 (CH phenyl), 126.86 (CH phenyl), 123.32 (CH phenyl), 69.89 (CH chloramphenicol), 66.68 (CH chloramphenicol), 63.45 ($CH_2$ chloramphenicol), 53.90 (CH chloramphenicol), 42.52 ($CH_2$), 41.97 ($CH_2$), 37.19 ($CH_2$), 30.06 ($CH_2$), 29.29 ($CH_2$); ESI-MS m/z calcd. for $C_{28}H_{31}Cl_2N_5O_{11}$ [M]+: m/z=683.14, found $[M-H]^-$ 682.30.

Compound 11. $^1H$ NMR (400 MHz, DMSO-$d_6$, 25° C., ppm): δ 8.51 (d, J=8.0 Hz, 1H), 8.16 (m, 4H), 8.03 (dd, J=4.0, 8.0 Hz, 1H), 7.63 (d, J=8.0 Hz, 2H), 7.27 (m, 2H), 7.20 (m, 3H), 6.43 (s, 1H), 5.02 (s, 1H), 4.41 (m, 1H), 4.20 (m, 2H), 4.08 (m, 1H), 3.67 (m, 4H), 3.04 (dd, J=4.0, 8.0 Hz, 1H), 2.87 (dd, J=8.0, 4.0 Hz, 1H), 2.46 (m, 4H); $^{13}C$ NMR (100 MHz, DMSO-$d_6$, 25° C., ppm): δ 173.14 (CO carboxyl), 172.61 (CO carboxyl), 171.71 (CONH amide), 169.56 (CONH amide), 169.05 (CONH amide), 164.05 (CONH chloramphenicol), 150.65 (CCH phenyl), 147.01 ($CNO_2$ phenyl), 137.85 ($CCH_2$ phenyl), 129.52 (CH phenyl), 128.61 (CH phenyl), 127.87 (CH phenyl), 126.86 (CH phenyl), 123.32 (CH phenyl), 69.89 (CH chloramphenicol), 66.69 (CH chloramphenicol), 63.45 ($CH_2$ chloramphenicol), 53.90 (CH chloramphenicol), 42.52 ($CH_2$), 41.97 ($CH_2$), 37.19 ($CH_2$), 30.06 ($CH_2$), 29.29 ($CH_2$); ESI-MS m/z calcd. for $C_{28}H_{31}Cl_2N_5O_{11}$ [M]+: m/z=683.14, found $[M-H]^-$ 682.39.

Compound 1m. $^1H$ NMR (400 MHz, DMSO-$d_6$, 25° C., ppm): δ 8.50 (d, J=12.0 Hz, 1H), 8.36 (s, 1H), 8.16 (m, 2H), 8.06 (m, 2H), 7.63 (d, J=8.0 Hz, 2H), 7.20 (m, 5H), 6.44 (s, 1H), 5.01 (s, 1H), 4.53 (m, 1H), 4.21 (m, 2H), 4.08 (m, 1H), 3.73 (m, 3H), 3.56 (m, 1H), 3.03 (d, J=12.0 Hz, 1H), 2.76 (t, J=12.0, 1H), 2.43 (m, 4H); $^{13}C$ NMR (100 MHz, DMSO-$d_6$, 25° C., ppm): δ 172.62 (CO carboxyl), 171.80 (CO carboxyl), 171.53 (CONH amide), 171.44 (CONH amide), 169.08 (CONH amide), 164.05 (CONH chloramphenicol), 150.63 (CCH phenyl), 147.01 ($CNO_2$phenyl), 138.20 ($CCH_2$ phenyl), 129.56 (CH phenyl), 128.45 (CH phenyl), 127.87 (CH phenyl), 126.68 (CH phenyl), 123.32 (CH phenyl), 69.92 (CH chloramphenicol), 66.69 (CH chloramphenicol), 63.49 ($CH_2$ chloramphenicol), 54.13 (CH), 53.94 (CH chloramphenicol), 42.32 ($CH_2$), 41.06 ($CH_2$), 38.03 ($CH_2$), 30.01 ($CH_2$), 29.30 ($CH_2$); ESI-MS m/z calcd. for $C_{28}H_{31}Cl_2N_5O_{11}$ [M]+: m/z=683.14, found $[M-H]^-$ 682.17.

Compound 1n. $^1H$ NMR (400 MHz, DMSO-$d_6$, 25° C., ppm): δ 8.50 (d, J=8.0 Hz, 1H), 8.29 (t, J=4.0 Hz, 1H), 8.17 (m, 3H), 8.05 (dd, J=8.0, 4.0 Hz, 1H), 7.63 (d, J=8.0 Hz, 2H), 7.21 (m, 5H), 6.43 (s, 1H), 5.01 (s, 1H), 4.50 (m, 1H), 4.20 (m, 2H), 4.07 (m, 1H), 3.74 (m, 4H), 3.04 (dd, J=4.0, 8.0 Hz, 1H), 2.76 (m, 1H), 2.35 (m, 4H); $^{13}C$ NMR (100 MHz, DMSO-$d_6$, 25° C., ppm): δ 172.53 (CO carboxyl), 171.94 (CO carboxyl), 171.48 (CONH amide), 171.29 (CONH amide), 169.46 (CONH amide), 164.07 (CONH chloramphenicol), 150.64 (CCH phenyl), 147.01 ($CNO_2$ phenyl), 138.36 ($CCH_2$ phenyl), 129.54 (CH phenyl), 128.43 (CH phenyl), 127.88 (CH phenyl), 126.63 (CH phenyl), 123.32 (CH phenyl), 69.93 (CH chloramphenicol), 66.69 (CH chloramphenicol), 63.51 ($CH_2$ chloramphenicol), 54.54 (CH), 53.93 (CH chloramphenicol), 42.22 ($CH_2$), 41.00 ($CH_2$), 37.86 ($CH_2$), 30.13 ($CH_2$), 29.35 ($CH_2$); ESI-MS m/z calcd. for $C_{28}H_{31}Cl_2N_5O_{11}$ [M]+: m/z=683.14, found $[M-H]^-$ 682.30.

Compound 1o. $^1H$ NMR (400 MHz, DMSO-$d_6$, 25° C., ppm): δ 8.51 (d, J=8.0 Hz, 1H), 8.32 (d, J=8.0 Hz, 1H), 8.15 (m, 3H), 7.99 (m, 2H), 7.63 (d, J=8.0 Hz, 2H), 7.21 (m, 11H), 6.43 (d, J=4.0 Hz, 1H), 5.02 (s, 1H), 4.53 (m, 1H), 4.42 (m, 1H), 4.20 (m, 2H), 4.09 (m, 1H), 3.69 (m, 3H), 2.99 (m, 5H), 2.71 (m, 2H), 2.44 (m, 2H); $^{13}C$ NMR (100 MHz, DMSO-$d_6$, 25° C., ppm): δ 173.08 (CO carboxyl), 172.60 (CO carboxyl), 171.69 (CONH amide), 171.43 (CONH amide), 169.60 (CONH amide), 168.74 (CONH amide), 164.05 (CONH chloramphenicol), 150.64 (CCH phenyl), 147.01 ($CNO_2$phenyl), 138.10 ($CCH_2$ phenyl), 137.81 (CH phenyl), 129.60 (CH phenyl), 129.52 (CH phenyl), 128.63 (CH phenyl), 128.41 (CH phenyl), 127.87 (CH phenyl), 126.87 (CH phenyl), 126.65 (CH phenyl), 123.32 (CH phenyl), 69.89 (CH chloramphenicol), 66.68 (CH chloramphenicol), 63.45 ($CH_2$ chloramphenicol), 53.96 (CH chloramphenicol), 42.50 ($CH_2$), 42.10 ($CH_2$), 37.94 ($CH_2$), 37.06 ($CH_2$), 30.05 ($CH_2$), 29.28 ($CH_2$); ESI-MS m/z calcd. for $C_{37}H_{40}Cl_2N_6O_{12}$ [M]+: m/z=830.21, found $[M-H]^-$ 829.29.

Compound 1p. $^1H$ NMR (400 MHz, DMSO-$d_6$, 25° C., ppm): δ 8.51 (m, 1H), 8.31 (m, 1H), 8.14 (m, 3H), 7.98 (m, 2H), 7.62 (m, 2H), 7.23 (m, 10H), 6.42 (d, J=16.0 Hz, 1H), 5.00 (d, J=16.0 Hz, 1H), 4.46 (m, 4H), 4.14 (m, 2H), 3.68 (m, 3H), 3.55 (m, 1H), 2.97 (m, 3H), 2.68 (m, 1H), 2.47 (m, 4H); $^{13}C$ NMR (100 MHz, DMSO-$d_6$, 25° C., ppm): δ 173.08 (CO carboxyl), 172.60 (CO carboxyl), 171.68 (CONH amide), 171.42 (CONH amide), 169.59 (CONH amide), 168.73 (CONH amide), 164.04 (CONH chloramphenicol), 150.64 (CCH phenyl), 147.01 ($CNO_2$phenyl), 138.10 ($CCH_2$ phenyl), 137.82 (CH phenyl), 129.60 (CH phenyl), 129.52 (CH phenyl), 128.63 (CH phenyl), 128.41 (CH phenyl), 127.87 (CH phenyl), 126.87 (CH phenyl), 126.65 (CH phenyl), 123.32 (CH phenyl), 69.88 (CH chloramphenicol), 66.68 (CH chloramphenicol), 63.44 ($CH_2$ chloramphenicol), 53.95 (CH chloramphenicol), 42.49 ($CH_2$), 42.09 ($CH_2$), 37.94 ($CH_2$), 37.05 ($CH_2$), 30.05 ($CH_2$), 29.28 ($CH_2$); ESI-MS m/z calcd. for $C_{37}H_{40}Cl_2N_6O_{12}$ [M]+: m/z=830.21, found $[M-H]^-$ 829.29.

Compound 1q. $^1H$ NMR (400 MHz, DMSO-$d_6$, 25° C., ppm): δ 12.54 (s, 1H), 8.51 (d, J=12.0 Hz, 1H), 8.16 (m, 7H), 7.64 (d, J=8.0 Hz, 2H), 6.43 (d, J=4 Hz, 1H), 6.20 (s, 1H), 5.03 (s, 1H), 4.21 (m, 2H), 4.11 (m, 1H), 3.74 (s, 10H), 2.46 (m, 4H); $^{13}C$ NMR (100 MHz, DMSO-$d_6$, 25° C., ppm): δ 172.63 (CO carboxyl), 171.73 (CO carboxyl), 171.49 (CONH amide), 169.84 (CONH amide), 169.63 (CONH amide), 169.53 (CONH amide), 169.47 (CONH amide), 164.05 (CONH chloramphenicol), 150.66 (CCH phenyl), 147.01 ($CNO_2$phenyl), 127.88 (CH phenyl), 123.32 (CH phenyl), 69.89 (CH chloramphenicol), 66.69 (CH chloramphenicol), 63.47 ($CH_2$ chloramphenicol), 53.93 (CH chloramphenicol), 42.56 ($CH_2$), 42.43 ($CH_2$), 42.13 ($CH_2$), 40.97 ($CH_2$), 30.07 ($CH_2$), 29.30 ($CH_2$); ESI-MS m/z calcd. for $C_{25}H_{31}Cl_2N_7O_{13}$ [M]+: m/z=707.14, found $[M-H]^-$ 706.22.

Compound 2a. $^1H$ NMR (400 MHz, DMSO-$d_6$, 25° C., ppm): δ 8.55 (d, J=8.0 Hz, 1H), 8.22 (d, J=8.0 Hz, 1H), 8.17

(d, J=8.0 Hz, 2H), 8.09 (d, J=8.0 Hz, 1H), 7.59 (m, 4H), 6.45 (s, 1H), 5.03 (s, 1H), 4.32 (m, 2H), 4.20 (m, 4H), 4.09 (m, 2H), 3.08 (m, 4H), 2.44 (m, 4H), 1.64 (m, 8H); $^{13}C$ NMR (100 MHz, DMSO-$d_6$, 25° C., ppm): δ 173.62 (CO carboxyl), 172.01 (CO carboxyl), 171.18 (CONH amide), 164.13 (CONH amide), 164.10 (CO trifluoroacetic acid) 158.95 ($NH_2C(NH)_2$), 157.10 (CONH amide), 150.61 (CCH phenyl), 147.02 ($CNO_2$phenyl), 127.87 (CH phenyl), 123.33 (CH phenyl), 109.99 ($CF_3$ trifluoroacetic acid), 69.93 (CH chloramphenicol), 66.68 (CH chloramphenicol), 63.53 ($CH_2$ chloramphenicol), 53.93 (CH chloramphenicol), 52.28 (CH), 51.92 (CH), 49.01 ($CH_3$ methanol), 40.93 ($CH_2$), 40.70 ($CH_2$), 30.02 ($CH_2$), 29.84 ($CH_2$), 29.30 ($CH_2$), 28.46 ($CH_2$), 25.56 ($CH_2$), 25.34 ($CH_2$); ESI-MS m/z calcd. for $C_{27}H_{42}Cl_2N_{10}O_{10}$ [M]+: m/z=736.25, found $[M-3H]^{3-}$ 733.43.

Compound 2b. $^1H$ NMR (400 MHz, DMSO-$d_6$, 25° C., ppm): δ 8.55 (d, J=8.0 Hz, 1H), 8.17 (t, J=8.0 Hz, 3H), 8.05 (d, J=8.0 Hz, 1H), 7.70 (s, 6H), 7.64 (d, J=8.0 Hz, 2H), 6.45 (s, 1H), 6.24 (d, J=8.0 Hz, 1H), 5.03 (s, 1H), 4.19 (m, 5H), 2.74 (m, 4H), 2.44 (m, 4H), 1.53 (m, 6H), 1.34 (m, 6H); $^{13}C$ NMR (100 MHz, DMSO-$d_6$, 25° C., ppm): δ 173.84 (CO carboxyl), 172.65 (CO carboxyl), 172.22 (CONH amide), 171.16 (CONH amide), 164.10 (CONH amide), 150.64 (CCH phenyl), 147.02 ($CNO_2$ phenyl), 127.88 (CH phenyl), 123.34 (CH phenyl), 69.89 (CH chloramphenicol), 66.69 (CH chloramphenicol), 63.45 ($CH_2$ chloramphenicol), 53.91 (CH chloramphenicol), 52.48 (CH), 52.00 (CH), 39.17 ($CH_2$), 39.02 ($CH_2$), 32.01 ($CH_2$), 30.74 ($CH_2$), 30.06 ($CH_2$), 29.35 ($CH_2$), 27.14 ($CH_2$), 26.92 ($CH_2$), 22.79 ($CH_2$), 22.63 ($CH_2$); ESI-MS m/z calcd. for $C_{27}H_{42}Cl_2N_6O_{10}$ [M]+: m/z=680.23, found $[M-3H]^{3-}$ 677.27.

Compound 2c. $^1H$ NMR (400 MHz, DMSO-$d_6$, 25° C., ppm): δ 12.61 (s, 1H), 8.56 (d, J=8.0 Hz, 1H), 8.17 (d, J=8.0 Hz, 3H), 8.06 (d, J=8.0 Hz, 1H), 7.73 (s, 6H), 7.63 (d, J=12.0 Hz, 2H), 6.45 (s, 1H), 6.24 (d, J=8.0 Hz, 1H), 5.02 (s, 1H), 4.20 (m, 5H), 2.74 (s, 4H), 2.43 (m, 4H), 1.51 (m, 6H), 1.35 (m, 6H); $^{13}C$ NMR (100 MHz, DMSO-$d_6$, 25° C., ppm): δ 173.84 (CO carboxyl), 172.60 (CO carboxyl), 172.21 (CONH amide), 171.15 (CONH amide), 164.13 (CONH amide), 150.62 (CCH phenyl), 147.02 ($CNO_2$ phenyl), 127.88 (CH phenyl), 123.34 (CH phenyl), 69.98 (CH chloramphenicol), 66.70 (CH chloramphenicol), 63.61 ($CH_2$ chloramphenicol), 53.97 (CH chloramphenicol), 52.46 (CH), 52.02 (CH), 39.12 ($CH_2$), 39.01 ($CH_2$), 31.99 ($CH_2$), 30.71 ($CH_2$), 30.07 ($CH_2$), 29.40 ($CH_2$), 27.11 ($CH_2$), 26.92 ($CH_2$), 22.79 ($CH_2$), 22.60 ($CH_2$); ESI-MS m/z calcd. for $C_{27}H_{42}Cl_2N_6O_{10}$ [M]+: m/z=680.23, found $[M-3H]^{3-}$ 677.42.

Compound 2d. $^1H$ NMR (400 MHz, DMSO-$d_6$, 25° C., ppm): δ 12.71 (s, 1H), 8.52 (d, J=8.0 Hz, 1H), 8.22 (d, J=8.0 Hz, 1H), 8.14 (m, 3H), 8.05 (m, 2H), 7.62 (m, 3H), 7.57 (t, J=4.0 Hz, 1H), 7.19 (m, 14H), 6.42 (m, 1H), 5.01 (s, 1H), 4.50 (m, 2H), 4.32 (m, 1H), 4.18 (m, 3H), 4.08 (m, 1H), 2.94 (m, 8H), 2.67 (m, 2H), 2.32 (m, 4H), 1.75 (m, 2H), 1.57 (m, 6H); $^{13}C$ NMR (100 MHz, DMSO-$d_6$, 25° C., ppm): δ 173.58 (CO carboxyl), 172.51 (CO carboxyl), 171.68 (CONH amide), 171.53 (CONH amide), 171.22 (CONH amide), 171.11 (CONH amide), 164.11 (CONH amide), 157.10 ($NH_2C(NH)_2$), 157.07 ($NH_2C(NH)_2$), 150.58 (CCH phenyl), 147.01 ($CNO_2$phenyl), 138.16 ($CCH_2$ phenyl), 137.88 ($CCH_2$ phenyl), 129.59 (CH phenyl), 129.48 (CH phenyl), 128.45 (CH phenyl), 128.39 (CH phenyl), 127.86 (CH phenyl), 123.32 (CH phenyl), 69.99 (CH chloramphenicol), 66.68 (CH chloramphenicol), 54.17 ($CH_2$ chloramphenicol), 53.95 (CH chloramphenicol), 52.34 (CH), 52.00 (CH), 30.13 ($CH_2$), 29.32 ($CH_2$), 25.56 ($CH_2$), 25.25 ($CH_2$); ESI-MS m/z calcd. for $C_{45}H_{60}Cl_2N_{12}O_{12}$ [M]+: m/z=1030.38, found $[M-3H]^{3-}$1027.59.

Compound 2e. $^1H$ NMR (400 MHz, DMSO-$d_6$, 25° C., ppm): δ 8.52 (d, J=8.0 Hz, 1H), 8.16 (d, J=8.0 Hz, 2H), 8.06 (m, 3H), 7.70 (s, 5H), 7.62 (d, J=8.0 Hz, 2H), 7.19 (m, 10H), 6.44 (s, 1H), 5.01 (s, 1H), 4.49 (m, 2H), 4.19 (m, 5H), 3.03 (m, 1H), 2.93 (m, 1H), 2.73 (m, 6H), 2.32 (m, 4H), 1.67 (m, 4H), 1.52 (m, 4H), 1.35 (m, 2H), 1.24 (s, 2H); $^{13}C$ NMR (100 MHz, DMSO-$d_6$, 25° C., ppm): δ 173.77 (CO carboxyl), 172.76 (CO carboxyl), 172.50 (CONH amide), 171.52 (CONH amide), 171.15 (CONH amide), 171.06 (CONH amide), 164.09 (CONH amide), 150.60 (CCH phenyl), 147.02 ($CNO_2$ phenyl), 138.20 ($CCH_2$ phenyl), 137.99 ($CCH_2$ phenyl), 129.60 (CH phenyl), 129.49 (CH phenyl), 128.45 (CH phenyl), 127.87 (CH phenyl), 126.71 (CH phenyl), 126.60 (CH phenyl), 123.33 (CH phenyl), 69.98 (CH chloramphenicol), 66.69 (CH chloramphenicol), 63.65 ($CH_2$ chloramphenicol), 54.18 (CH), 53.95 (CH chloramphenicol), 52.31 (CH), 52.15 (CH), 52.04 (CH), 37.66 ($CH_2$), 31.95 ($CH_2$), 30.79 ($CH_2$), 30.14 ($CH_2$), 29.34 ($CH_2$), 27.11 ($CH_2$), 26.94 ($CH_2$), 26.90 ($CH_2$), 22.77 ($CH_2$), 22.67 ($CH_2$), 22.48 ($CH_2$); ESI-MS m/z calcd. for $C_{45}H_{60}Cl_2N_8O_{12}$ [M]+: m/z=974.37, found $[M-3H]^{3-}$ 971.37.

Compound 2f. $^1H$ NMR (400 MHz, DMSO-$d_6$, 25° C., ppm): δ 12.67 (s, 1H), 8.52 (m, 1H), 8.13 (m, 4H), 7.63 (m, 5H), 6.44 (d, J=8.0 Hz, 1H), 6.22 (t, J=4.0 Hz, 1H), 5.03 (s, 1H), 4.15 (m, 4H), 3.73 (m, 2H), 2.75 (dd, J=8.0, 4.0 Hz, 2H), 2.44 (m, 4H), 1.71 (m, 2H), 1.54 (m, 2H), 1.33 (m, 2H); $^{13}C$ NMR (100 MHz, DMSO-$d_6$, 25° C., ppm): δ 173.82 (CO carboxyl), 172.62 (CO carboxyl), 171.56 (CONH amide), 169.34 (CONH amide), 164.08 (CONH amide), 150.64 (CCH phenyl), 147.02 ($CNO_2$ phenyl), 127.88 (CH phenyl), 123.33 (CH phenyl), 69.92 (CH chloramphenicol), 66.70 (CH chloramphenicol), 63.50 ($CH_2$ chloramphenicol), 53.95 (CH chloramphenicol), 51.88 (CH), 42.16 ($CH_2$), 39.06 ($CH_2$), 30.92 ($CH_2$), 30.07 ($CH_2$), 29.35 ($CH_2$), 26.90 ($CH_2$), 22.69 ($CH_2$); ESI-MS m/z calcd. for $C_{23}H_{32}Cl_2N_5O_{10}$ [M]+: m/z=608.15, found $[M-2H]^{2-}$ 606.33.

Compound 2g. $^1H$ NMR (400 MHz, DMSO-$d_6$, 25° C., ppm): δ 8.51 (d, J=8.0 Hz, 1H), 8.17 (d, J=8.0 Hz, 3H), 8.06 (d, J=8.0 Hz, 1H), 7.64 (d, J=8.0 Hz, 2H), 6.44 (s, 1H), 6.19 (d, J=4.0 Hz, 1H), 5.02 (s, 1H), 4.20 (m, 5H), 2.42 (m, 4H), 2.26 (t, J=8.0 Hz, 4H), 1.92 (m, 2H), 1.75 (m, 2H); $^{13}C$ NMR (100 MHz, DMSO-$d_6$, 25° C., ppm): δ 174.43 (CO carboxyl), 174.11 (CO carboxyl), 173.50 (CO carboxyl), 172.64 (CO carboxyl), 171.81 (CONH amide), 171.16 (CONH amide), 164.05 (CONH amide), 150.63 (CCH phenyl), 147.01 ($CNO_2$ phenyl), 127.87 (CH phenyl), 123.32 (CH phenyl), 69.89 (CH chloramphenicol), 66.69 (CH chloramphenicol), 63.45 ($CH_2$ chloramphenicol), 53.91 (CH chloramphenicol), 51.99 (CH), 51.60 (CH), 30.46 ($CH_2$), 30.41 ($CH_2$), 30.04 ($CH_2$), 29.32 ($CH_2$), 28.02 ($CH_2$), 26.50 ($CH_2$); ESI-MS m/z calcd. for $C_{25}H_{30}Cl_2N_4O_{14}$ [M]+: m/z=680.11, found $[M-H]^-$ 679.23.

Compound 2h. $^1H$ NMR (400 MHz, DMSO-$d_6$, 25° C., ppm): δ 12.44 (s, 3H), 8.52 (d, J=8.0 Hz, 1H), 8.23 (d, J=8.0 Hz, 1H), 8.17 (d, J=8.0 Hz, 2H), 8.05 (d, J=8.0 Hz, 1H), 7.64 (d, J=8.0 Hz, 2H), 6.44 (s, 1H), 5.04 (s, 1H), 4.60 (m, 1H), 4.50 (m, 1H), 4.22 (m, 2H), 4.10 (t, J=8.0 Hz, 1H), 2.66 (m, 4H), 2.43 (m, 4H); $^{13}C$ NMR (100 MHz, DMSO-$d_6$, 25° C., ppm): δ 172.62 (CO carboxyl), 172.54 (CO carboxyl), 172.09 (CO carboxyl), 172.05 (CO carboxyl), 171.25 (CONH amide), 170.96 (CONH amide), 164.06 (CONH amide), 150.65 (CCH phenyl), 147.01 ($CNO_2$ phenyl), 127.89 (CH phenyl), 123.32 (CH phenyl), 69.89 (CH chloramphenicol), 66.68 (CH chloramphenicol), 63.53 ($CH_2$ chloramphenicol), 53.91 (CH chloramphenicol), 49.62 (CH), 48.97 (CH), 36.57 ($CH_2$), 36.23 ($CH_2$), 30.14 ($CH_2$), 29.31 ($CH_2$); ESI-MS m/z calcd. for $C_{23}H_{26}Cl_2N_4O_{14}$ [M]+: m/z=652.08, found $[M-H]^-$ 651.15.

Compound 2i. $^1H$ NMR (400 MHz, DMSO-$d_6$, 25° C., ppm): δ 12.40 (s, 2H), 8.52 (d, J=8.0 Hz, 1H), 8.23 (d, J=8.0 Hz, 1H), 8.16 (d, J=8.0 Hz, 2H), 8.01 (d, J=4.0 Hz, 1H), 7.63 (d, J=8.0 Hz, 2H), 6.44 (s, 1H), 6.21 (s, 1H), 5.03 (s, 1H), 4.58 (dd, J=8.0, 4.0 Hz, 1H), 4.49 (m, 1H), 4.22 (m, 2H), 4.10 (m, 1H), 2.66 (m, 2H), 2.55 (m, 2H), 2.42 (m, 4H); $^{13}C$ NMR (100 MHz, DMSO-$d_6$, 25° C., ppm): δ 172.59 (CO carboxyl), 172.11 (CO carboxyl), 172.05 (CO carboxyl), 171.25 (CONH amide), 170.90 (CONH amide), 164.08 (CONH amide), 150.62 (CCH phenyl), 147.02 ($CNO_2$ phenyl), 127.88 (CH phenyl), 123.32 (CH phenyl), 69.97 (CH chloramphenicol), 66.69 (CH chloramphenicol), 63.62 ($CH_2$ chloramphenicol), 53.95 (CH chloramphenicol), 49.62 (CH), 49.00 (CH), 36.56 ($CH_2$), 30.15 ($CH_2$), 29.35 ($CH_2$); ESI-MS m/z calcd. for $C_{23}H_{26}Cl_2N_4O_{14}$ [M]+: m/z=652.08, found $[M-H]^-$ 651.25.

Compound 2j. $^1H$ NMR (400 MHz, DMSO-$d_6$ 25° C., ppm): δ 8.51 (d, J=4.0 Hz, 1H), 8.17 (m, 4H), 7.63 (m, 2H), 6.43 (d, J=4.0 Hz, 1H), 5.03 (s, 1H), 4.54 (m, 1H), 4.22 (m, 2H), 4.09 (m, 1H), 3.16 (d, J=4.0 Hz, 3H), 2.65 (m, 2H), 2.44 (m, 4H); $^{13}C$ NMR (100 MHz, DMSO-$d_6$, 25° C., ppm): δ 172.63 (CO carboxyl), 172.60 (CO carboxyl), 172.05 (CO carboxyl), 171.47 (CONH amide), 169.17 (CONH amide), 164.05 (CONH amide), 150.64 (CCH phenyl), 147.02 ($CNO_2$phenyl), 127.88 (CH phenyl), 123.32 (CH phenyl), 69.91 (CH chloramphenicol), 66.69 (CH chloramphenicol), 63.49 ($CH_2$ chloramphenicol), 53.93 (CH chloramphenicol), 49.01 (CH), 42.09 ($CH_2$), 36.42 ($CH_2$), 30.06 ($CH_2$), 29.32 ($CH_2$); ESI-MS m/z calcd. for $C_{21}H_{24}Cl_2N_4O_{12}$ [M]+: m/z=594.08, found $[M-H]^-$ 593.32.

Compound 3a. $^1H$ NMR (400 MHz, DMSO-$d_6$, 25° C., ppm): δ 8.50 (d, J=8.0 Hz, 1H), 8.26 (d, J=8.0 Hz, 1H), 8.17 (m, 2H), 8.07 (d, J=8.0 Hz, 1H), 7.63 (d, J=8.0 Hz, 2H), 7.22 (m, 10H), 6.44 (s, 1H), 5.01 (s, 1H), 4.53 (m, 1H), 4.43 (m, 1H), 4.20 (m, 2H), 4.09 (m, 1H), 2.98 (m, 3H), 2.69 (t, J=12.0 Hz, 1H), 2.33 (m, 4H); $^{13}C$ NMR (100 MHz, DMSO-$d_6$, 25° C., ppm): δ 173.12 (CO carboxyl), 172.51 (CO carboxyl), 171.66 (CONH amide), 170.88 (CONH amide), 164.05 (CONH amide), 150.63 (CCH phenyl), 147.01 ($CNO_2$phenyl), 138.24 ($CCH_2$ phenyl), 137.80 ($CCH_2$ phenyl), 129.57 (CH phenyl), 129.53 (CH phenyl), 128.60 (CH phenyl), 128.37 (CH phenyl), 127.89 (CH phenyl), 126.87 (CH phenyl), 126.59 (CH phenyl), 123.33 (CH phenyl), 69.94 (CH chloramphenicol), 66.70 (CH chloramphenicol), 63.49 ($CH_2$ chloramphenicol), 53.91 (CH chloramphenicol), 37.92 ($CH_2$), 37.06 ($CH_2$), 30.14 ($CH_2$), 29.38 ($CH_2$); ESI-MS m/z calcd. for $C_{33}H_{34}Cl_2N_4O_{10}$ [M]+: m/z=716.17, found $[M-H]^-$ 715.39.

Compound 3b. $^1H$ NMR (400 MHz, DMSO-$d_6$, 25° C., ppm): δ 8.49 (d, J=8.0 Hz, 1H), 8.34 (d, J=8.0 Hz, 1H), 8.15 (d, J=8.0 Hz, 2H), 8.01 (dd, J=8.0, 12.0 Hz, 2H), 7.83 (m, 3H), 7.74 (s, 1H), 7.61 (d, J=8.0 Hz, 2H), 7.44 (m, 3H), 7.15 (m, 9H), 6.43 (s, 1H), 6.18 (d, J=4.0 Hz, 1H), 4.99 (s, 1H), 4.56 (m, 2H), 4.43 (m, 1H), 4.21 (m, 2H), 4.07 (m, 1H), 3.24 (m, 1H), 3.11 (m, 1H), 2.99 (m, 1H), 2.88 (m, 1H), 2.76 (m, 1H), 2.62 (m, 1H), 2.30 (m, 4H), 1.23 (s, 1H); $^{13}C$ NMR (100 MHz, DMSO-$d_6$, 25° C., ppm): δ 173.03 (CO carboxyl), 172.47 (CO carboxyl), 171.39 (CONH amide), 171.30 (CONH amide), 170.84 (CONH amide), 164.05 (CONH amide), 150.61 (CCH phenyl), 147.00 ($CNO_2$ phenyl), 138.24 ($CCH_2$ naphthyl), 137.97 ($CCH_2$ phenyl), 135.43 ($CCH_2$ phenyl), 133.39 (C naphthyl), 132.30 (C naphthyl), 129.60 (CH phenyl), 129.50 (CH phenyl), 128.39 (CH phenyl), 128.28 (CH phenyl), 128.11 (CH phenyl), 128.04 (CH phenyl), 127.90 (CH phenyl), 127.87 (CH phenyl), 127.84 (CH phenyl), 126.64 (CH naphthyl), 126.48 (CH naphthyl), 126.37 (CH naphthyl), 125.90 (CH naphthyl), 123.31 (CH phenyl), 69.96 (CH chloramphenicol), 66.70 (CH chloramphenicol), 63.53 ($CH_2$ chloramphenicol), 54.08 (CH), 54.01 (CH), 53.91 (CH chloramphenicol), 37.93 ($CH_2$), 37.76 ($CH_2$), 37.31 ($CH_2$), 30.11 ($CH_2$), 29.35 ($CH_2$); ESI-MS m/z calcd. for $C_{46}H_{45}Cl_2N_5O_{11}$ [M]+: m/z=913.25, found $[M-H]^-$ 912.45.

Compound 3c. $^1H$ NMR (400 MHz, DMSO-$d_6$, 25° C., ppm): δ 8.50 (d, J=8.0 Hz, 1H), 8.24 (m, 2H), 8.15 (m, 2H), 8.08 (m, 2H), 8.01 (d, J=8.0 Hz, 1H), 7.82 (m, 3H), 7.75 (s, 1H), 7.62 (m, 2H), 7.44 (m, 2H), 7.15 (m, 10H), 6.43 (s, 1H), 5.00 (s, 1H), 4.68 (m, 1H), 4.48 (m, 2H), 4.19 (m, 2H), 4.07 (m, 1H), 3.75 (d, J=4.0 Hz, 4H), 3.23 (m, 1H), 3.00 (m, 2H), 2.86 (m, 1H), 2.76 (m, 1H), 2.61 (m, 1H), 2.30 (m, 4H); $^{13}C$ NMR (100 MHz, DMSO-$d_6$, 25° C., ppm): δ 172.49 (CO carboxyl), 171.49 (CO carboxyl), 171.44 (CONH amide), 171.37 (CONH amide), 170.89 (CONH amide), 169.39 (CONH amide), 164.07 (CONH amide), 150.60 (CCH phenyl), 147.01 ($CNO_2$phenyl), 138.23 ($CCH_2$ naphthyl), 137.98 ($CCH_2$ phenyl), 135.72 ($CCH_2$ phenyl), 133.39 (C naphthyl), 132.25 (C naphthyl), 129.56 (CH phenyl), 129.51 (CH phenyl), 128.41 (CH phenyl), 128.28 (CH phenyl), 127.88 (CH phenyl), 127.82 (CH phenyl), 126.63 (CH naphthyl), 126.50 (CH naphthyl), 126.29 (CH naphthyl), 125.79 (CH naphthyl), 123.32 (CH phenyl), 69.98 (CH chloramphenicol), 66.70 (CH chloramphenicol), 63.55 ($CH_2$ chloramphenicol), 54.36 (CH), 54.29 (CH), 53.99 (CH), 53.95 (CH chloramphenicol), 42.24 ($CH_2$), 41.00 ($CH_2$), 38.04 ($CH_2$), 37.81 ($CH_2$), 37.74 ($CH_2$), 30.11 ($CH_2$), 29.35 ($CH_2$); ESI-MS m/z calcd. for $C_{50}H_{51}Cl_2N_7O_{13}$ [M]+: m/z=1027.29, found $[M-H]^-$ 1026.49.

Compound 4a. $^1H$ NMR (400 MHz, DMSO-$d_6$, 25° C., ppm): δ 8.51 (d, J=8.0 Hz, 1H), 8.18 (m, 3H), 7.63 (d, J=12.0 Hz, 2H), 6.43 (m, 1H), 5.03 (s, 1H), 4.14 (m, 5H), 2.44 (m, 4H), 1.24 (m, 3H); $^{13}C$ NMR (100 MHz, DMSO-$d_6$, 25° C., ppm): δ 174.69 (CO carboxyl), 172.62 (CO carboxyl), 171.06 (CONH amide), 164.13 (CONH amide), 150.78 (CCH phenyl), 147.10 ($CNO_2$phenyl), 127.98 (CH phenyl), 123.40 (CH phenyl), 69.93 (CH chloramphenicol), 66.78 (CH chloramphenicol), 63.48 ($CH_2$ chloramphenicol), 54.00 (CH chloramphenicol), 48.00 (CH), 30.00 ($CH_2$), 29.37 ($CH_2$), 17.72 ($CH_3$); ESI-MS m/z calcd. for $C_{18}H_{21}Cl_2N_3O_9$ [M]+: m/z=493.07, found $[M-H]^-$ 492.29.

Compound 4b. $^1H$ NMR (400 MHz, DMSO-$d_6$, 25° C., ppm): δ 8.52 (d, J=4.0 Hz, 1H), 8.17 (m, 2H), 7.62 (m, 2H), 6.43 (d, J=4.0 Hz, 1H), 6.22 (d, J=4.0 Hz, 1H), 5.01 (s, 1H), 4.24 (m, 2H), 4.11 (m, 1H), 3.59 (d, J=4.0 Hz, 3H), 2.55 (s, 4H); $^{13}C$ NMR (100 MHz, DMSO-$d_6$, 25° C., ppm): δ 172.87 (CO carboxyl), 172.19 (CO carboxyl), 164.17 (CONH amide), 150.65 (CCH phenyl), 147.12 ($CNO_2$ phenyl), 127.94 (CH phenyl), 123.43 (CH phenyl), 70.07 (CH chloramphenicol), 66.78 (CH chloramphenicol), 63.90 ($CH_2$ chloramphenicol), 54.03 (CH chloramphenicol), 52.01 ($CH_3$), 29.09 ($CH_2$), 28.84 ($CH_2$); ESI-MS m/z calcd. for $C_{16}H_{18}Cl_2N_2O_8$ [M]+: m/z=436.04, found $[M-H]^-$ 435.15.

Compound 4c. $^1H$ NMR (400 MHz, DMSO-$d_6$, 25° C., ppm): δ 8.51 (d, J=12.0 Hz, 1H), 8.16 (m, 2H), 7.77 (s, 1H), 7.64 (m, 2H), 6.44 (d, J=4.0 Hz, 1H), 5.03 (s, 1H), 4.14 (m, 5H), 3.29 (m, 2H), 2.55 (m, 2H), 2.33 (m, 2H); $^{13}C$ NMR (100 MHz, DMSO-$d_6$, 25° C., ppm): δ 172.54 (CO carboxyl), 170.68 (CONH amide), 164.03 (CONH amide), 150.70 (CCH phenyl), 147.02 ($CNO_2$phenyl), 127.92 (CH phenyl), 123.33 (CH phenyl), 69.85 (CH chloramphenicol), 66.71 (CH chloramphenicol), 63.33 ($CH_2$ chloramphenicol), 53.97 (CH chloramphenicol), 50.93 ($CH_2$), 36.04 ($CH_2$), 30.36 ($CH_2$), 29.45 ($CH_2$); ESI-MS m/z calcd. for $C_{17}H_{21}Cl_2N_3O_{10}S$ [M]+: m/z=529.03, found $[M-H]^-$ 528.25.

Compound 4d. $^1H$ NMR (400 MHz, DMSO-$d_6$, 25° C., ppm): δ 8.51 (m, 1H), 8.16 (m, 2H), 8.03 (m, 1H), 7.63 (m, 2H), 6.43 (m, 1H), 5.02 (d, J=8.0 Hz, 1H), 4.21 (s, 2H), 4.10 (m, 1H), 3.79 (m, 2H), 3.25 (m, 2H), 2.47 (m, 2H), 2.37 (m, 2H); $^{13}C$ NMR (100 MHz, DMSO-$d_6$, 25° C., ppm): δ 172.59 (CO carboxyl), 171.40 (CONH amide), 164.05 (CONH amide), 150.66 (CCH phenyl), 147.02 ($CNO_2$ phenyl), 127.87 (CH phenyl), 123.32 (CH phenyl), 69.89 (CH chloramphenicol), 66.69 (CH chloramphenicol), 64.18 ($CH_2$), 64.13 ($CH_2$ chloramphenicol), 63.45 (CH chloramphenicol), 53.93 ($CH_2$), 30.10 ($CH_2$), 29.32 ($CH_2$); ESI-MS m/z calcd. for $C_{17}H_{22}Cl_2N_3O_{11}P$ [M]+: m/z=545.04, found $[M-H]^-$ 544.24.

Example 8—Antibacterial Activity of CLsuGG Analogues

After obtaining the pure conjugates, those analogues were tested for their antibacterial activity against a wild type *E. coli* strain (K-12). As shown in Table 6, the first category, relatively hydrophilic neutral peptides conjugated to CLsu (1a-1q), exhibits higher inhibitory activity than other categories of the conjugates, with MICs ranging from 20 to 200 μM, which is comparable to that of CL but much lower than that of CLsu (standard compounds). Examples 1-5 above demonstrated that diglycine conjugated CLsu increases the efficacy of the prodrugs most effectively. The replacement of the C-terminal glycine on CLsuGG by leucine, alanine, or serine generates 1a, 1b, and 1c, which all exhibit a MIC of 20 μM. Switching the location of glycine and serine in 1c produces 1d, which exhibits a MIC (40 μM) twice of that of 1c. These results suggest that directly linking the carboxyl group of CLsu by a glycine residue is important for the high activity of the prodrugs. Capping the carboxylic acid of CLsuGG by N-methyl group (using N-methylamine hydrochloride) forms 1e, which exhibits the MIC of 20 μM. The activity of 1e is comparable to that of CLsuGG, indicating that capping the C-terminal of CLsuGG by N-methyl group has little effect on the hydrolysis of prodrugs.

TABLE 6

The Minimum Inhibitory Concentration (MIC) of Peptides-Conjugated CLsu Against *E. coli* (K-12)

| # | Compound | MIC (μM) |
|---|---|---|
| — | CL | 20 |
| — | CLsu | >200 |
| 1a | CLsu-Gl | 20 |
| 1b | CLsu-Ga | 20 |
| 1c | CLsu-Gs | 20 |
| 1d | CLsu-sG | 40 |
| 1e | CLsu-GGNHMe | 20 |
| 1f | CLsu-GGGG | 20 |
| 1g | CLsu-aa | 80 |
| 1h | CLsu-AA | 100 |
| 1i | CLsu-aaa | 80 |
| 1j | CLsu-AAA | 100 |
| 1k | CLsu-GGf | 20 |
| 1l | CLsu-GGF | 20 |
| 1m | CLsu-GFG | 20 |
| 1n | CLsu-FGG | 80 |
| 1o | CLsu-GGff | 20 |

TABLE 6-continued

The Minimum Inhibitory Concentration (MIC) of Peptides-Conjugated CLsu Against *E. coli* (K-12)

| # | Compound | MIC (μM) |
|---|---|---|
| 1p | CLsu-GGFF | 20 |
| 1q | CLsu-GGGGG | 40 |
| 2a | CLsu-rr | 200 |
| 2b | CLsu-kk | 200 |
| 2c | CLsu-KK | 200 |
| 2d | CLsu-ffrr | 200 |
| 2e | CLsu-ffkk | 200 |
| 2f | CLsu-GK | 20 |
| 2g | CLsu-ee | >200 |
| 2h | CLsu-dd | >200 |
| 2i | CLsu-DD | 200 |
| 2j | CLsu-GD | 20 |
| 3a | CLsu-ff | 100 |
| 3b | CLsu-ff(2-Nal) | >200 |
| 3c | CLsu-ff(2-Nal)GG | >200 |
| 4a | CLsu-a | >200 |
| 4b | CLsu-OMe | >200 |
| 4c | CLsu-Tau | 40 |
| 4d | CLsu-ep | 100 |

Di-D-alanine and di-L-alanine replace the diglycine in CLsuGG to generate 1g and 1h, which exhibit MIC values of 80 μM and 100 μM, respectively. Being considerably higher than that of CLsuGG but close to each other, the MIC values of 1g and 1h indicate that the side chains on the amino acid residues of the peptides likely affect the hydrolysis of prodrugs by the esterases. 1i and 1j, containing three alanine residues and being enantiomers, exhibit MIC values of 80 and 100 μM, respectively. These results indicate that D-alanine slightly enhances the activity of the prodrugs and agrees with the previous observation that dipeptide (i.e., diglycine) is optimal for enhancing the antibacterial efficacy of the conjugates.

Inserting one phenylalanine in CLsuGG at a different position of produces 1k, 1l, 1m, and 1n, which exhibit MIC values of 20, 20, 20, and 80 μM, respectively. While the activity of 1l is comparable to that of CLsuGG, the activity of in is ten times lower than that of CLsuGG. This result indicates that phenylalanine should be away from the ester linkage to favor the hydrolysis of the prodrug. The activities of 1k and 1m are comparable to that of CLsuGG, indicating that the position of phenylalanine affects little on the activities of the prodrugs when glycine is the first residue connected to succinate. The attachment of two D- or L-diphenylalanine in the carboxylic acid end of CLsuGG generates 1o and 1p, both of which exhibit a MIC value of 20 μM, which is similar with that of 1k and 1l, indicating that the number of phenylalanine may have little effect on the hydrolysis. While the conjugate 1f, containing four glycine residues, shows a comparable activity (MIC=20 μM) to that of CLsuGG, the conjugate 1q, containing five glycine residues and exhibiting the MIC of 40 μM, is considerably less active than CLsuGG. This result again agrees with earlier conclusion that diglycine is optimal for enhancing the antibacterial efficacy of CL, although various di-, tri-, and tetra-peptides produced comparable results.

Considering the electrostatic interactions with negatively charged bacterial membrane (Dickson & Koohmaraie, "Cell Surface Charge Characteristics and their Relationship to Bacterial Attachment to Meat Surfaces," *Appl. Environ. Microbiol.* 55(4):832-836 (1989), which is hereby incorporated by reference in its entirety), the second category of conjugates (2a-2j) were designed by attaching charged peptides to CLsu. The incorporation of two D-arginine and two D-lysine residues generates 2a and 2b, with the MIC values of 200 and 200 μM, respectively, which are similar with 1g (80 μM) and 1h (100 μM) in the first category. With two L-lysine residues in the conjugates, the MIC of 2c is 200 μM. This result indicates that the D- and L-lysine residues would have similar influences on the activities of the prodrugs. Moreover, the insertion of two D-phenylalanine residues in 2a and 2b generates 2d and 2e, which still shows comparable activity with that of 2a and 2b, with both the MIC values of 200 μM. Using one glycine to replace one L-lysine in 2c leads to 2f, which shows much higher inhibitory activity (20 μM) than 2c (200 μM).

Besides introducing the above positively charged peptides, various negatively charged peptides were also attached in the conjugates and their antibacterial efficiency was compared with the positively charged ones. Containing glutamic acid or aspartic acid residues, 2g, 2h, and 2i all exhibit high MIC values (2g: >200 μM; 2h: >200 μM; 2i: 200 μM), indicating multiple negative charges decrease the activities of the prodrugs. This notion is supported by the lower MIC value (20 μM) of 2j, containing -Gly-Asp residues, than that of 2i. These results are consistent with the idea that the negatively charged bacterial membrane may electrostatically repel the prodrugs bearing multiple negative charges.

Introducing either hydrophilic neutral peptides or charged peptides to CLsu results in water soluble conjugates. To understand the roles of solubility, conjugates attached with hydrophobic peptides or steric hindrance in side chains to CLsu (3a-3c) were created. The direct attachment of diphenylalanine in the carboxylic acid end of CLsu generates 3a, which shows low inhibitory activity against *E. coli* with a MIC value of 100 μM. Furthermore, attaching a hydrophobic amino acid (i.e., naphthylalanine) produces 3b, which is more hydrophobic than 3a, hardly inhibits *E. coli* growth, and the concentration is higher than 200 μM. In addition, the insertion of diphenylalanine and naphthylalanine in CLsuGG forms 3c, which also results in a MIC value higher than 200 μM. These observations imply that the incorporation of hydrophobic peptides significantly impairs the efficiency of prodrugs, if the solubility of the conjugates is low. This observation is reasonable since low solubility increases difficulty to enter bacterial membranes and decreases the rate of hydrolysis of the ester bond by the esterases.

Besides peptide conjugates, there are conjugates bearing a single alanine (4a), or only capping the C-terminal of CLsu with a methyl (4b), sulfate (4c), or phosphate group (4d). 4a exhibits a high MIC value (>200 μM), implying that the direct attachment of one amino acid residue to CLsu has little influence on the hydrolysis of the prodrugs. Blocking the carboxyl group with methyl group generates water-insoluble 4b with two ester bonds. The high MIC value of 4b (>200 μM) suggests that multiple ester bonds and/or low solubility likely reduces the rate of hydrolysis by esterases. 4c and 4d exhibit the MIC of 40 and 100 μM, respectively, which are lower than the prodrug (i.e., CLsu (>200 μM)) but still higher than CLsuGG. The result is not only consistent with the fact that conjugating taurine (Zhou et al., "Taurine Boosts Cellular Uptake of Small D-Peptides for Enzyme-Instructed Intracellular Molecular Self-Assembly," *J. Am. Chem. Soc.* 137(32):10040-10043 (2015) and Li et al., "Enzyme-Instructed Intracellular Molecular Self-Assembly to Boost Activity of Cisplatin Against Drug-Resistant Ovarian Cancer Cells," *Angew. Chem. Int. Ed.* 54(45):13307-13311 (2015), which are hereby incorporated by reference in their entirety) plays a role in boosting cellular uptake, but also supports the conjugation of peptides to prodrugs as an effective way for enhancing efficacy of the prodrugs. Although the antibacterial activity of these peptide conjugated CL, like CL itself, is not as potent as that of some other broad-spectrum antibiotics (e.g., ciprofloxacin and trimethoprim with MIC of 0.01 μg/mL, 1 μg/mL and 0.6 μg/mL against *E. coli* K-12, respectively) (Sulavik et al., "Antibiotic Susceptibility Profiles of *Escherichia coli* Strains Lacking Multidrug Efflux Pump Genes," *Antimicrob. Agents Chemother.* 45(4):1126-1136 (2001); Greenwood & O'Grady, "Activity and Interaction of Trimethoprim and Sulphamethoxazole Against *Escherichia coli,*" *J. Clin. Pathol.* 29(2): 162-166 (1976); and Glassford et al., "Desmethyl Macrolides: Synthesis and Evaluation of 4-Desmethyl Telithromycin," *ACS Med. Chem. Lett.* 5(9):1021-1026 (2014), which are hereby incorporated by reference in their entirety), they not only show improved potency in the comparison of CLsu, the clinically failed prodrug of CL (Yogev et al., "Pharmacokinetic Comparison of Intravenous and Oral Chloramphenicol in Patients with *Haemophilus influenzae* Meningitis," *Pediatrics* 67(5): 656-660 (1981), which is hereby incorporated by reference in its entirety), but also exhibit better water-solubility than that of CL. This discovery may provide potentially clinical application for intravenous injection of the new prodrugs of CL.

Example 9—Hydrolysis Rate

Figures 11A, 11B, 11C:
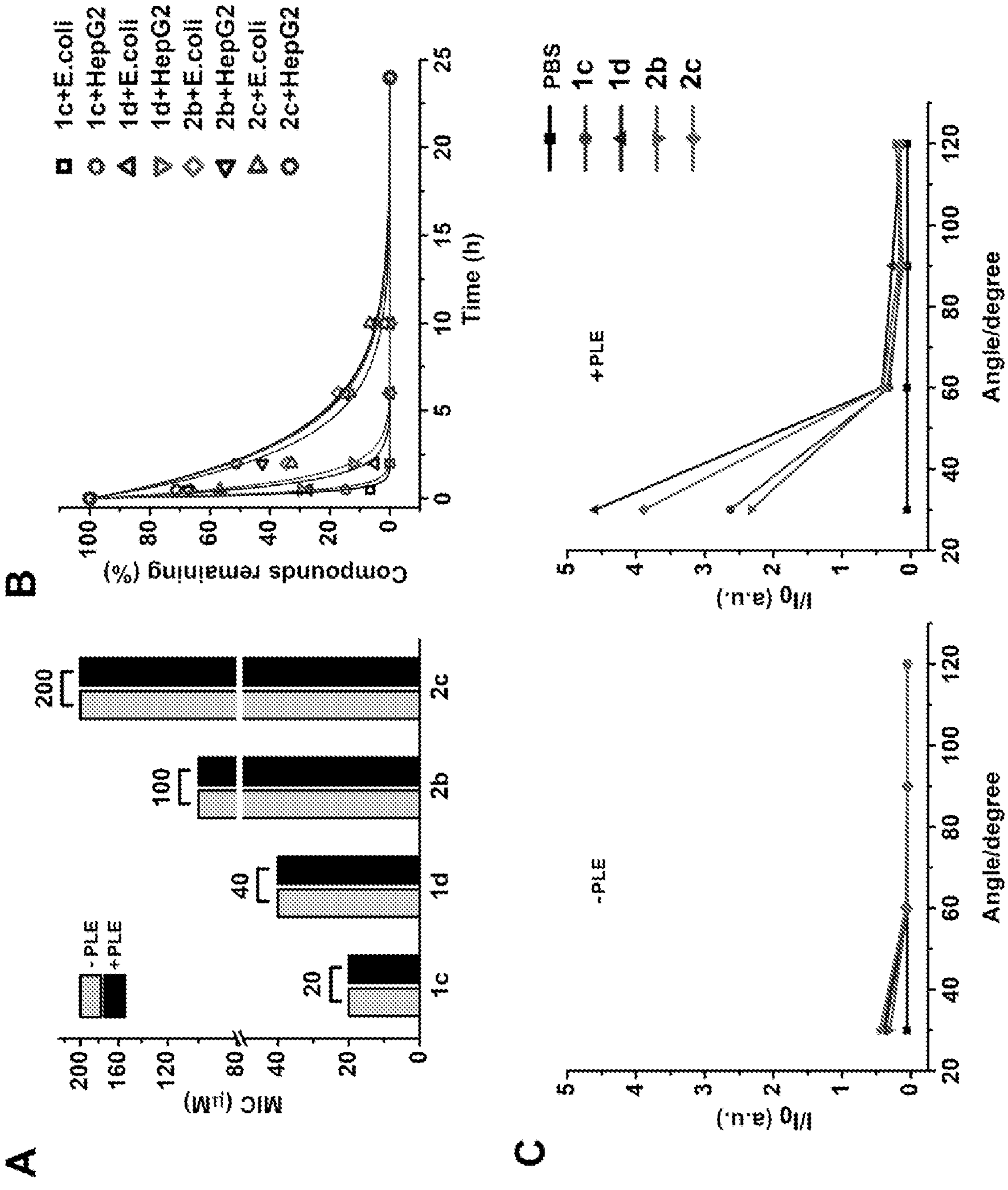
FIGS. 11A-11D show the characterization of 1c, 1d, 2b, and 2c.

To further understand the effects of the structures of conjugated-peptides on hydrolysis, as well as on the antibacterial activity, first, the antibacterial activity of 1c, 1d, 2b and 2c before and after the treatment of commercially available mammalian esterase (porcine liver esterase, PLE) (1U/mL) was compared. It was found that the addition of exogenous PLE hardly changes the inhibitory efficacy of 1c, 1d, 2b and 2c (FIG. 11A). Next, the hydrolysis rate of the ester bond of 1c, 1d, 2b and 2c was measured using *E. coli* or HepG2 (a hepatocyte cell which overexpress mammalian esterases—see Li et al., "Selectively Inducing Cancer Cell Death by Intracellular Enzyme-Instructed Self-Assembly (EISA) of Dipeptide Derivatives," *Adv. Healthc. Mater.* 6(15):1601400 (2017), which is hereby incorporated by reference in its entirety) lysates, after normalizing their activities. As shown in FIG. 11B, catalyzed by the lysate of either *E. coli* or HepG2, all peptide conjugated prodrugs are able to undergo complete hydrolysis for regenerating the active drug, which further supports the conclusion that the attachment of peptides to CLsu enhances the efficacy of the prodrugs. In detail, under the condition of *E. coli* lysates, the different conjugated peptides (with slightly different apparent first-order rate constant of 1c: 3.763 $h^{-1}$, 1d: 1.267 $h^{-1}$, 2b: 0.317 $h^{-1}$ and 2c: 0.310 $h^{-1}$) leads to different inhibitory activity of prodrugs with the tendency that the faster hydrolysis results in higher efficacy (1c: 20 μM, 1d: 40 μM, 2b: 200 μM and 2c: 200 μM).

Figure 11D:
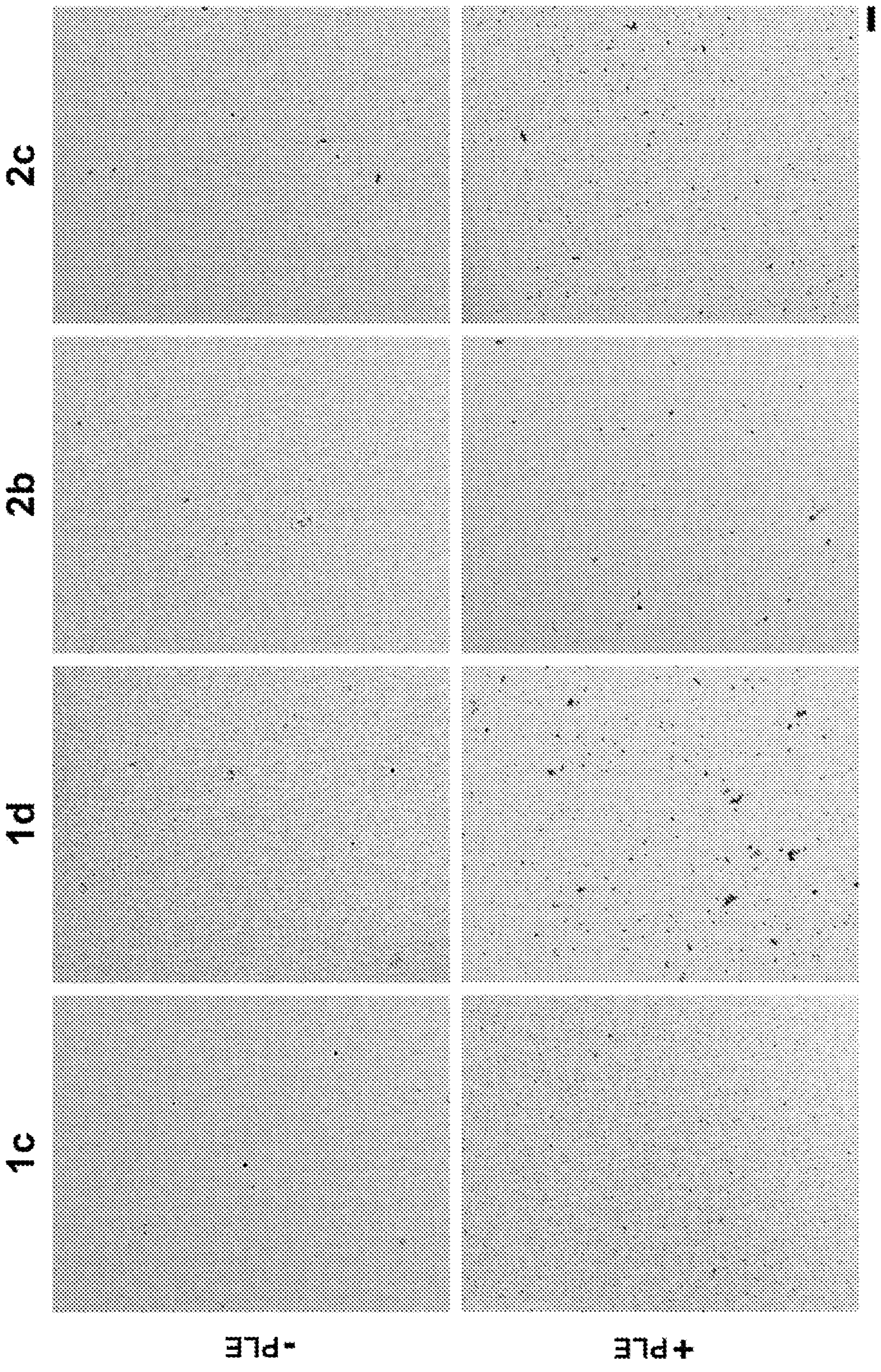

The intensities of the static light scattering signals increase drastically at different magnitudes after the addition of PLE to the solutions of 1c, 1d, 2b and 2c for 24 h (FIG. 11C), agreeing with the transmission electron microscopy (TEM) images, which show increased amount of nanoparticles after the addition of PLE (FIG. 11D). Besides confirming that the precursors become active antibiotics (i.e., CL) after the hydrolysis catalyzed by esterases, these results indicate that soluble precursors are able to undergo intrabacterial hydrolysis to form CL. Because of the poor solubility of CL, such a conversion enhances the retention of CL inside *E. coli.*

Furthermore, the serum stability of CLsu, 1c, 1d, 2b, 2c and several other most effective conjugates (e.g., 1k, 1o and 2f) was examined. CLsu and these conjugates were incubated in human serum (from human male AB plasma) at the concentration at 200 μM, 37° C. for 2 hours and 24 hours, respectively (Table 7). The LC-MS results show that all the conjugates hydrolyzed to form CL after 24 hours while the conversion of CLsu only achieved less than 15% after 24 hours. Furthermore, 1c, 1k, and 2f were able to hydrolyze completely within 2 hours. The discovery is consistent with earlier results confirming that the faster hydrolysis results in higher efficacy and further confirms that the attachment of peptides to CLsu would enhance the efficacy of prodrugs. In addition, the results also show that the different conjugated-peptides may lead to slightly different stability in serum environment. Therefore, these conjugates may achieve adequate serum concentration in a short time when administrated intravenously, which may address the shortcoming of CLsu and its clinical failure. However, the balance between serum stability outside of bacteria and targeting hydrolysis inside bacteria remains an area for further optimization of the peptide-antibiotic conjugates.

TABLE 7

The stability of CLsu, 1c, 1d, 1k, 1o, 2b, 2c and 2f in human serum.[a]

| | Compounds remaining (%) | | |
|---|---|---|---|
| Compound | 0 h | 2 h | 24 h |
| CLsu | 100 | 96.2 | 87.0 |
| 1c | 100 | 0 | 0 |
| 1d | 100 | 16.7 | 0 |
| 1k | 100 | 0 | 0 |
| 1o | 100 | 7.2 | 0 |
| 2b | 100 | 52.9 | 0 |
| 2c | 100 | 49.2 | 0 |
| 2f | 100 | 0 | 0 |

[a]All compounds were incubated in human serum (from human male AB plasma) at the concentration at 200 μM, 37° C. for 2 hours and 24 hours, respectively.

Example 10—Uptake Mechanism

Examples 1-5 demonstrated that diglycine conjugated CLsu enters the bacteria via multiple paths, including ydgR (i.e., inner membrane oligopeptide transporters involving in the uptake of di- and tripeptides) (Prabhala et al., "The Prototypical Proton-Coupled Oligopeptide Transporter YdgR from *Escherichia coli* Facilitates Chloramphenicol Uptake into Bacterial Cells," *J. Biol. Chem.* 293(3):1007-1017 (2018), which is hereby incorporated by reference in its entirety), fepA (i.e., siderophore transporter) (Buchanan et al., "Crystal Structure of the Outer Membrane Active Transporter FepA from *Escherichia coli,*" *Nat. Struct. Biol.* 6(1):56-63 (1999), which is hereby incorporated by reference in its entirety), and passive diffusion.

Figure 12:
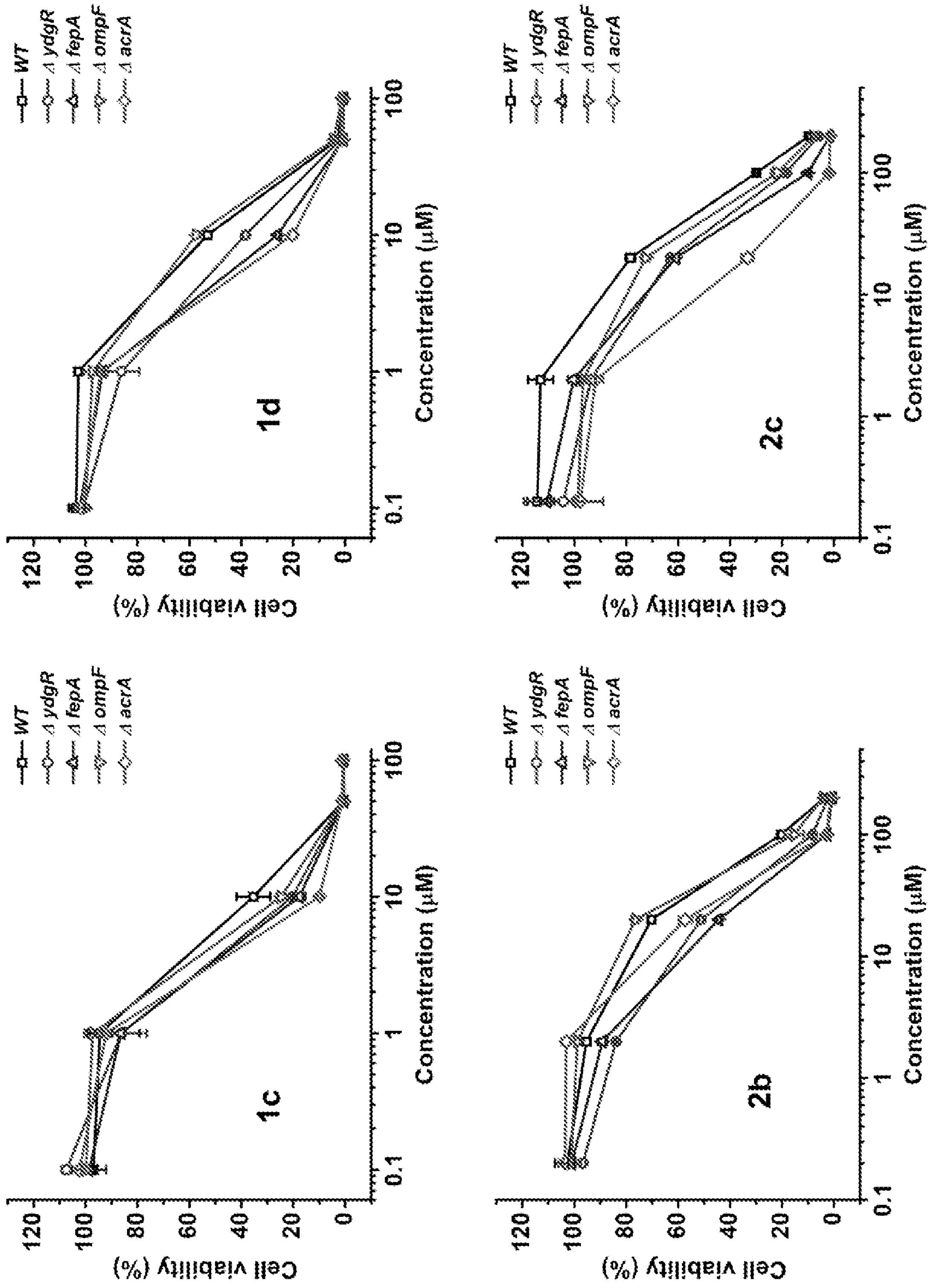
FIG. 12 is a panel of graphs showing the antibacterial activity of 1c, 1d, 2b, and 2c against ydgR, fepA, ompF transporter deletion mutants or acrA efflux pump deletion mutant of *E. coli.*

Several representative peptides conjugating CLsu (e.g., 1c, 1d, 2b and 2c) were chosen to study the effects of conjugated peptides on the uptake of the prodrugs. In addition to testing the activities of these conjugates against *E. coli* mutants that have ydgR or fepA deleted, the activities of these conjugates against *E. coli* mutants that have deletions of ompF (i.e., outer membrane porin transporters mediating the non-specific diffusion of small solutes) (Masi & Pages, "Structure, Function and Regulation of Outer Membrane Proteins Involved in Drug Transport in Enterobactericeae: The OmpF/C—To1C Case," *Open Microbiol. J.* 7:22-33 (2013), which is hereby incorporated by reference in its entirety) or acrA (i.e., the periplasmic lipoprotein component of multidrug efflux pumps) (Nishino & Yamaguchi, "Analysis of a Complete Library of Putative Drug Transporter Genes in *Escherichia coli,*" *J. Bacteriol.* 183(20):5803-5812 (2001) and Tikhonova et al., "AcrA, AcrB, and TolC of *Escherichia coli* form a Stable Intermembrane Multidrug Efflux Complex," *J. Biol. Chem.* 279(31):32116-32124 (2004), which are hereby incorporated by reference in its entirety) were also measured. As shown in FIG. 12, the activities of 1c, 1d, 2b and 2c were compared against ydgR, fepA, ompF, acrA mutants and wild-type *E. coli*. When the mutants are treated by 1c, 1d, 2b and 2c, the deletion of ydgR, fepA, or ompF reduces the viability of bacteria at different magnitudes and hardly rescues the bacteria, indicating that ydgR, fepA, and ompF are unlikely to be the major contributors for the precursors entering the bacteria, and mutation of one transporter may not lead to drug resistance of these precursors. However, the deletion of acrA significantly reduces the viabilities of the mutant treated by the conjugates (1c: 30%, 1d: 40%, 2b: 20%, 2c: 50%), indicating that acrA likely plays a key role in pumping out the precursors and contributes to bacterial resistance (Li et al., "The Challenge of Efflux-Mediated Antibiotic Resistance in Gram-Negative Bacteria," *Clin. Microbiol. Rev.* 28(2):337-418 (2015), which is hereby incorporated by reference in its entirety).

Example 11—Intrabacterial Hydrolysis

Figure 13:
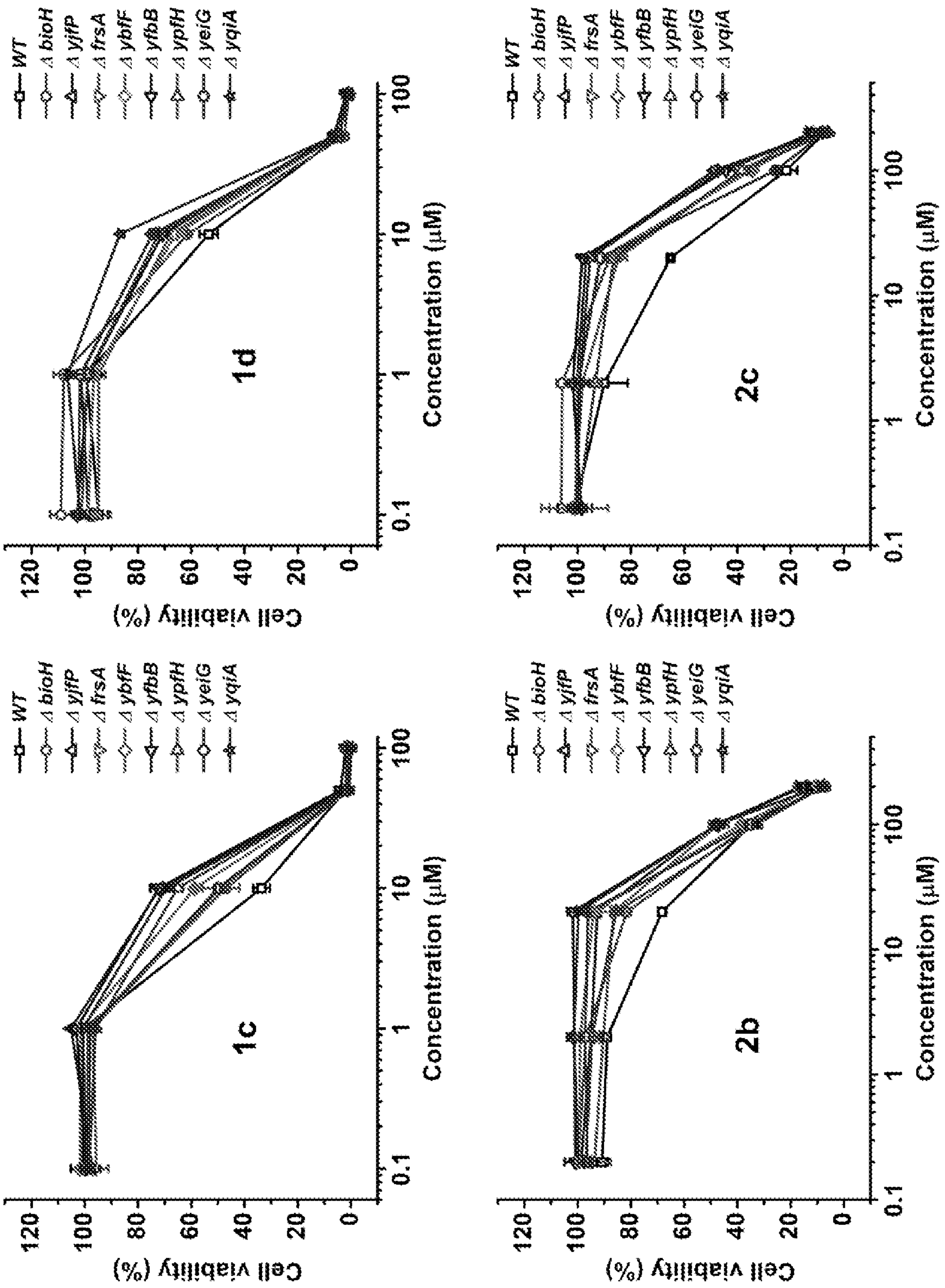
FIG. 13 is a panel of graphs showing the antibacterial activity of 1c, 1d, 2b, and 2c against esterase (bioH, yjfP, frsA, ybfF, yfbB, ypfH, yeiG, or yqiA) deletion mutants of *E. coli.*

To examine the role of different bacterial esterases on the hydrolysis of different peptides conjugated to CLsu, the activities of 1c, 1d, 2b, and 2c were measured against eight *E. coli* mutants that have deletions of one of the bacterial esterase genes (i.e., bioH, yjfP, frsA, ybfF, yfbB, ypfH, yeiG, or yqiA) (Godinho et al., "Discovery of an *Escherichia coli* Esterase with High Activity and Enantioselectivity Toward 1,2-O-isopropylideneglycerol Esters," *Appl. Environ. Microbiol.* 77(17):6094-6099 (2011); Tomczyk et al., "Purification and Characterisation of the BIOH Protein from the Biotin Biosynthetic Pathway," *FEBS Lett.* 513 (2-3):299-304 (2002); and Kuznetsova et al., "Enzyme Genomics: Application of General Enzymatic Screens to Discover New Enzymes," *FEMS Microbiol. Rev.* 29(2):263-279 (2005), which are hereby incorporated by reference in their entirety). As shown in FIG. 13, the deletion of the cytoplasmic esterase of *E. coli* reduces the antibacterial activities of 1c, 1d, 2b, and 2c moderately, at about 20%, 10%, 20% and 20%, respectively. This confirms that various esterases in the bacterial cytoplasm convert precursors to the active antibiotic agent (i.e., CL) after the precursors enter *E. coli.*

Example 12—Cytotoxicity Study

Figures 14A, 14B, 14C, 14D:
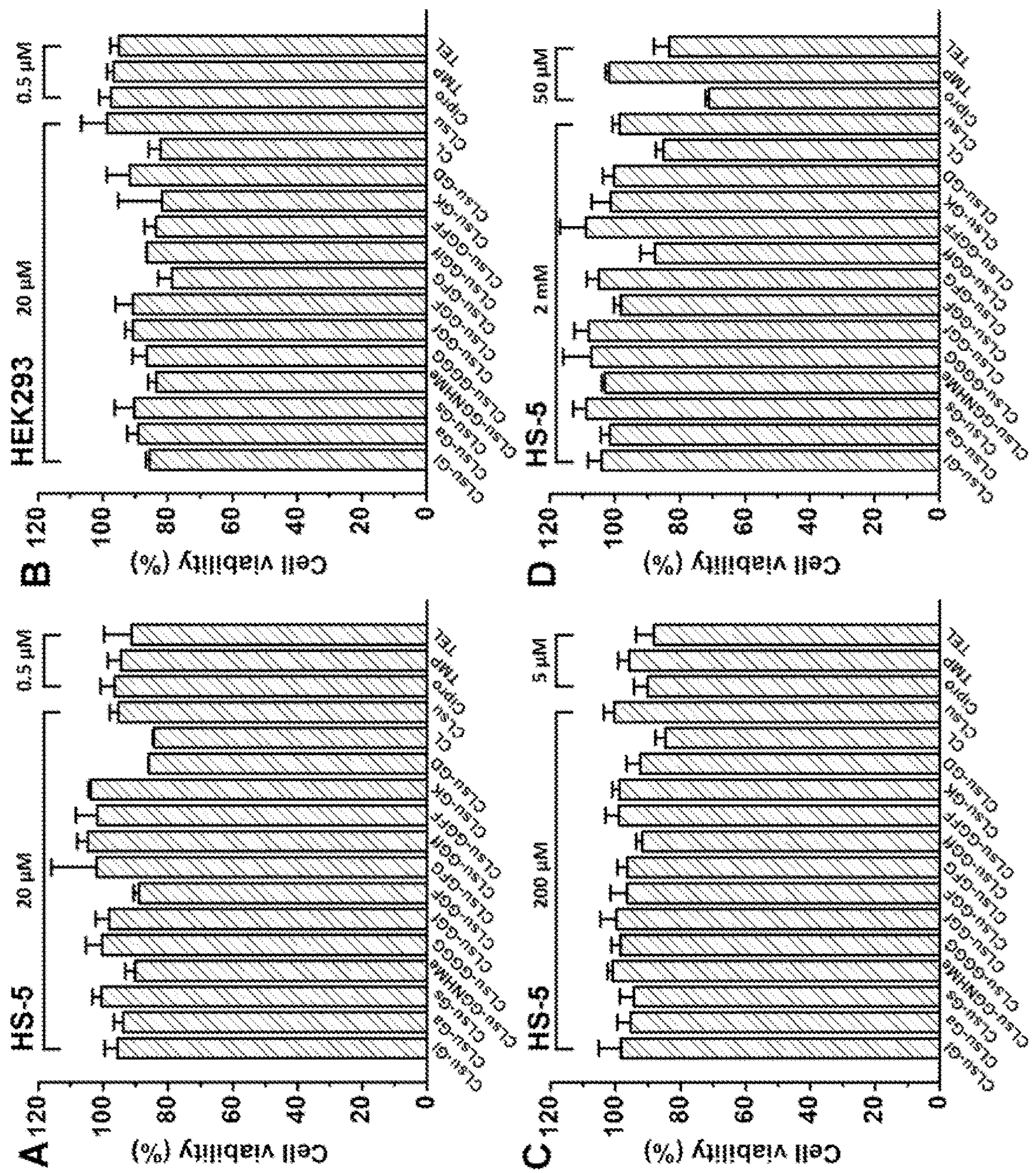
FIGS. 14A-14D show the cell viability of cells incubated with 1a, 1b, 1c, 1e, 1f, 1k, 1l, 1m, 1o, 1p, 2f, and 2j.

The results of Example 5 demonstrate that diglycine conjugating CLsu likely would reduce the major adverse effect of CL (i.e., bone marrow suppression), whereas it hardly alters the cytotoxicity of CL against HepG2 and HEK293. To assess the major side effects of additional conjugates, the cytotoxicities of the most effective conjugates with MIC values of 20 μM (i.e., 1a, 1b, 1c, 1e, 1f, 1k, 1l, 1m, 1o, 1p, 2f, and 2j) was compared to the control compounds (i.e., ciprofloxacin, trimethoprim, and telithromycin) against HS-5 and HEK293 cells. As shown in FIGS. 14A-14B, like prodrug CLsu, most of the conjugates show lower cytotoxicity than CL against HS-5 cells, confirming that peptide-conjugated CLsu likely would reduce the major adverse effect of CL. Meanwhile, ciprofloxacin (Cipro), trimethoprim (TMP), and telithromycin (TEL) also show relatively low cytotoxicity against HS-5 cells at the concentration of around MIC values. In addition, all conjugates show about the same cytotoxicity as CL against HEK293 cells, further confirming that peptide-conjugated CLsu scarcely alters the cytotoxicity of CL against HEK293. Furthermore, the concentration of these conjugates was increased to 10-fold and 100-fold of MIC values (i.e., 200 μM and 2 mM) to examine their cytotoxicities against HS-5 cells. As shown in FIGS. 14C-14D, all of them still show relatively lower cytotoxicity than CL against HS-5 cells, indicating their suitability for clinical administration.

Discussion of Examples 6-12

The results of Examples 6-12 demonstrate the further development of a series of peptide-conjugated prodrugs of chloramphenicol via a linker having an ester bond, which modulate the properties of the prodrugs. The antibacterial activity study of these conjugates against *E. coli* demonstrated the structure-activity relationship of these peptide conjugated chloramphenicols, which affords a powerful approach for developing antibiotic agents that treat bacterial infections. In addition, further hydrolysis investigation of the conjugates indicates that rapid intrabacterial hydrolysis is a useful way to increase the retention of active drugs inside bacteria and enhance the efficacy of prodrugs. Additionally, the Examples described herein demonstrate that acrA efflux pumps normally lead to the bacterial resistance, but various cytoplasmic esterases contributed to form active antibiotic agents after precursors entered *E. coli*, which indicates the future direction of molecular design based on the functions of bacterial esterases (Arpigny & Jaeger, "Bacterial Lipolytic Enzymes: Classification and Properties," *Biochem. J.* 343(1):177-183 (1999) and Bornscheuer, U. T., "Microbial Carboxyl Esterases: Classification, Properties and Application in Biocatalysis," *FEMS Microbiol. Rev.* 26(1):73-81 (2002), which are hereby incorporated by reference in their entirety) or bacterial efflux pumps (Sjuts et al., "Molecular Basis for Inhibition of AcrB Multidrug Efflux Pump by Novel and Powerful Pyranopyridine Derivatives," *Proc. Natl. Acad. Sci.* 113(13):3509-3514 (2016), which is hereby incorporated by reference in its entirety).

Example 13—Synthesis and Characterization of Chloramphenicol Prodrugs 6 and 7, and Ciprofloxacin Prodrugs 8, 9, 10, and 11

Given the success with chloramphenicol-peptide conjugates, several different peptide-conjugated prodrugs were prepared using (i) cyclohexane-1,2-dicarboxylic acid to replace the succinate linker, thereby forming unconjugated prodrug 6 and is diglycine derivative 7; (ii) ciprofloxacin to replace chloramphenicol while retaining use of succinate linker (forming unconjugated prodrugs 8 and 9, and its diglycine derivative 10); and (iii) omission of the succinate linker by forming a diglycine derivative of ciprofloxacin 11. See FIGS. 15-17. These prodrugs were prepared as described below, purified with Agilent 1100 Series Liquid Chromatography system, equipped with an XTerra C18 RP column and Variable Wavelength detector. The LC-MS spectra were obtained with a Waters Acquity Ultra Performance LC with Waters MICROMASS detector. $^1$H NMR spectra were obtained on Varian Unity Inova 400.

Compound 6. As shown in FIG. 15, chloramphenicol (323.1 mg, 1.0 mmol), trans-1,2-cyclohexanedicarboxylic anhydride (169.6 mg, 1.1 mmol), and 4-(dimethylamino) pyridine (24.4 mg, 0.2 mmol) were dissolved in THF (4 mL) and stirred at 50 overnight. After that, the solution was cooled to the room temperature, and THF was removed. The crude product was used for SPPS without further purification. The cell culture grade of compound 6 (yield: 79%) was purified by reverse phase HPLC using HPLC grade acetonitrile and water with supplement of 0.1% trifluoroacetic acid as the eluents. Subsequently, the structure of the prodrug was confirmed by $^1$H NMR and $^{13}$C NMR spectra as follows: $^1$H NMR (400 MHz, DMSO-d6, 25° C., ppm): δ 8.53 (dd, J=12.0, 8.0 Hz, 1H), 8.16 (d, J=8.0 Hz, 2H), 7.62 (d, J=8.0 Hz, 2H), 6.43 (m, 1H), 5.01 (s, 1H), 4.24 (m, 2H), 4.16 (d, J=8.0 Hz, 1H), 4.00 (t, J=8.0 Hz, 1H), 2.45 (m, 2H), 1.93 (d, J=28.0 Hz, 2H), 1.67 (s, 2H), 1.23 (s, 4H); $^{13}$C NMR (100 MHz, DMSO-d6, 25, ppm): δ 176.24, 174.55, 163.95, 150.57, 147.03, 127.87, 123.32, 69.89, 66.72, 63.31, 54.08, 53.78, 44.65, 44.51, 28.78, 25.22; ESI-MS m/z calcd. for $C_{19}H_{22}Cl_2N_2O_8$ [M]+: m/z=477.29, found [M-H]−475.13.

Compound 7. As shown in FIG. 15, 2-chlorotrityl chloride resin and N-Fmoc-glycine were used along with 6 to cap the N-terminal of the peptides. After cleaving the compounds from resin, compound 7 (yield: 71%) was purified by reverse phase HPLC using HPLC grade acetonitrile and water with supplement of 0.1% trifluoroacetic acid as the eluents. Subsequently, the structure of the prodrug was confirmed by $^1$H NMR and $^{13}$C NMR spectra as follows: $^1$H NMR (400 MHz, DMSO-d6, 25° C., ppm): δ 8.51 (dd, J=8.0, 24.0 Hz, 1H), 8.15 (m, 3H), 7.94 (m, 1H), 7.63 (m, 2H), 6.44 (d, J=12.0 Hz, 1H), 5.00 (d, J=16.0 Hz, 1H), 4.08 (m, 3H), 3.71 (m, 4H), 2.45 (m, 2H), 1.92 (s, 2H), 1.68 (s, 2H), 1.22 (m, 4H); $^{13}$C NMR (100 MHz, DMSO-d6, 25, ppm): δ 174.97, 174.79, 171.53, 169.69, 164.02, 150.74, 147.01, 127.87, 123.32, 69.76, 66.72, 63.29, 53.71, 45.44, 44.79, 42.10, 40.98, 29.75, 29.07, 25.36; ESI-MS m/z calcd. for $C_{23}H_{28}Cl_2N_4O_{10}$ [M]+: m/z=591.40, found [M-H]−589.23.

Figure 16:
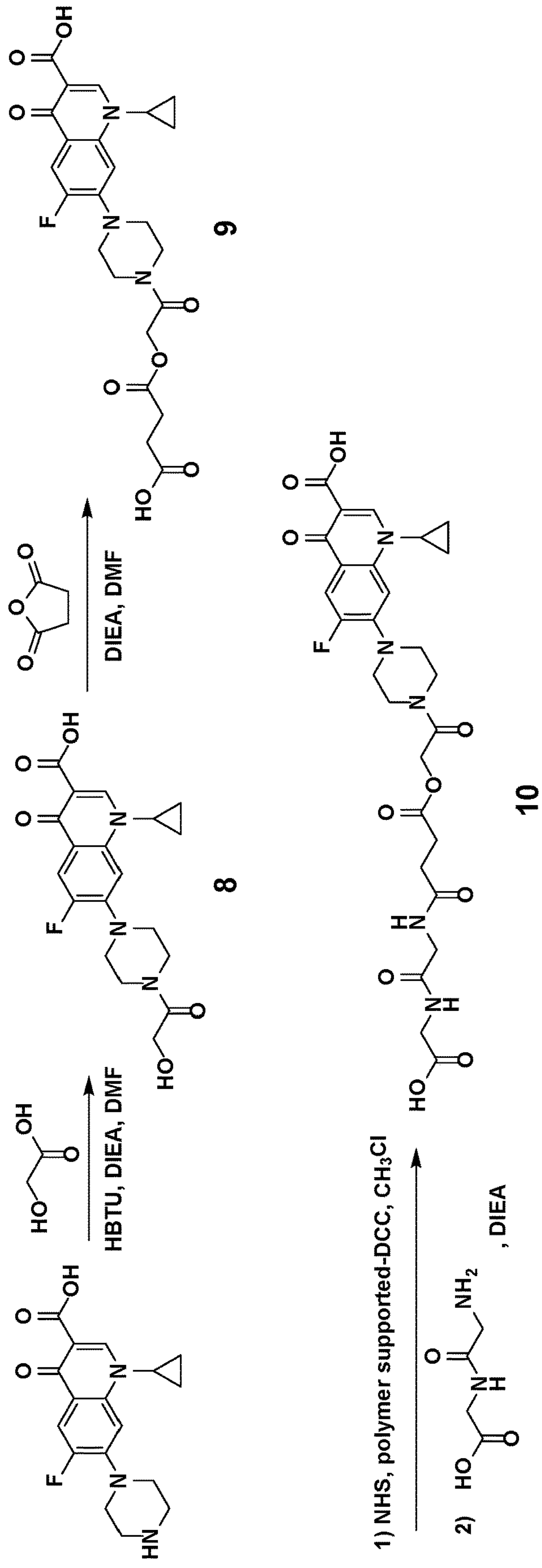
FIG. 16 is a reaction scheme showing the synthesis of ciprofloxacin prodrug compounds 8, 9, and 10 using 2-hydroxyacetic acid attached to the piperazine ring to form the intermediate 8, the unconjugated succinate prodrug 9, and its diglycine derivative 10.

Compound 8. As shown in FIG. 16, glycolic acid (106.5 mg, 1.4 mmol) and HBTU (530.9 mg, 1.4 mmol) dissolved in DMF (4 mL) and stirred for 30 minutes, followed by adding ciprofloxacin (331.3 mg, 1.0 mmol) and N,N-diisopropylethylamine (500 μL, 3.0 mmol) in the solution and stirring continuously overnight. Compound 8 (yield: 90%) was purified by silica gel chromatography (1% MeOH in $CH_2Cl_2$). Subsequently, the structure of the prodrug was confirmed by $^1$H NMR and $^{13}$C NMR spectra as follows: $^1$H NMR (400 MHz, DMSO-d6, 25° C., ppm): δ 8.66 (s, 1H), 7.93 (d, J=12.0 Hz, 1H), 7.58 (d, J=8.0 Hz, 1H), 4.16 (s, 2H), 3.82 (m, 1H), 3.65 (m, 4H), 3.34 (s, 4H), 1.32 (m, 2H), 1.19 (m, 2H); $^{13}$C NMR (100 MHz, DMSO-d6, 25° C., ppm): δ 176.79, 170.64, 166.31, 154.60, 152.13, 148.50, 145.27, 139.55, 119.31, 111.56, 111.33, 107.19, 60.62, 49.83, 43.74, 36.31, 8.02; ESI-MS m/z calcd. for $C_{19}H_{20}FN_3O_5$ [M]+: m/z=389.38, found [M-H]−388.08.

Compound 9. As shown in FIG. 16, compound 8 (110.0 mg, 0.3 mmol), succinic anhydride (39.6 mg, 0.4 mmol), and N,N-diisopropylethylamine (234 μL, 1.5 mmol) were dissolved in DMF (1 mL) and stirred at 40° C. overnight. Compound 9 (yield: 83%) was purified by reverse phase HPLC using HPLC grade acetonitrile and water with supplement of 0.1% trifluoroacetic acid as the eluents. Subsequently, the structure of the prodrug was confirmed by $^1$H NMR and $^{13}$C NMR spectra as follows: $^1$H NMR (400 MHz, DMSO-d6, 25° C., ppm): δ 8.67 (s, 1H), 7.93 (d, J=12.0 Hz, 1H), 7.59 (d, J=8.0 Hz, 1H), 4.87 (s, 2H), 3.83 (s, 1H), 3.65 (d, J=16.0 Hz, 4H), 3.35 (d, J=16.0 Hz, 4H), 2.62 (dd, J=8.0, 4.0 Hz, 2H), 2.51 (m, 2H), 1.32 (m, 2H), 1.19 (m, 2H); $^{13}$C NMR (100 MHz, DMSO-d6, 25° C., ppm): δ 176.81, 173.64, 172.15, 166.32, 165.33, 154.61, 152.13, 148.53, 145.32, 145.21, 139.56, 119.29, 111.58, 111.35, 107.20, 61.89, 49.84, 43.97, 36.32, 29.07, 8.03; ESI-MS m/z calcd. for $C_{23}H_{24}FN_3O_8$ [M]+: m/z=489.46, found [M-H]−488.33.

Compound 10. As shown in FIG. 16, compound 9 (120.0 mg, 0.25 mmol), diglycine (64.8 mg, 0.49 mmol), N-hydroxysuccinimide (28.3 mg, 0.25 mmol), N,N-diisopropylethylamine (200 μL, 1.23 mmol), and polymer supported-DCC (700.0 mg, 1.0-2.0 mmol/g loading) were poured in $CHCl_3$ (2 mL) and the reaction suspension was stirred at 40° C. for 4 hours. The resulting mixture was filtered, and the resin was washed several times with $CH_2Cl_2$. The filtrate was evaporated under reduced pressure and was purified by reverse phase HPLC (yield: 29%) using HPLC grade acetonitrile and water with supplement of 0.1% trifluoroacetic acid as the eluents. Subsequently, the structure of the prodrug was confirmed by $^1H$ NMR and $^{13}C$ NMR spectra as follows: $^1H$ NMR (400 MHz, DMSO-d6, 25° C., ppm): δ 8.67 (s, 1H), 8.24 (dd, J=8.0, 4.0 Hz, 1H), 8.10 (dd, J=4.0, 8.0 Hz, 1H), 7.95 (d, J=12.0 Hz, 1H), 7.59 (d, J=8.0 Hz, 2H), 4.86 (s, 2H), 3.83 (m, 1H), 3.74 (m, 4H), 3.65 (m, 5H), 3.41 (m, 2H), 2.63 (dd, J=8.0, 4.0 Hz, 2H), 2.47 (m, 2H), 1.32 (m, 2H), 1.19 (m, 2H); $^{13}C$ NMR (100 MHz, DMSO-d6, 25° C., ppm): δ 176.80, 172.45, 171.53, 171.43, 169.72, 166.31, 165.39, 154.61, 152.13, 148.52, 145.31, 139.55, 119.35, 111.57, 111.34, 107.20, 61.82, 49.82, 43.96, 36.31, 30.20, 29.25; ESI-MS m/z calcd. for $C_{27}H_{30}FN_5O_{10}$ [M]+: m/z=603.56, found [M-H]−602.29.

Figure 19A:
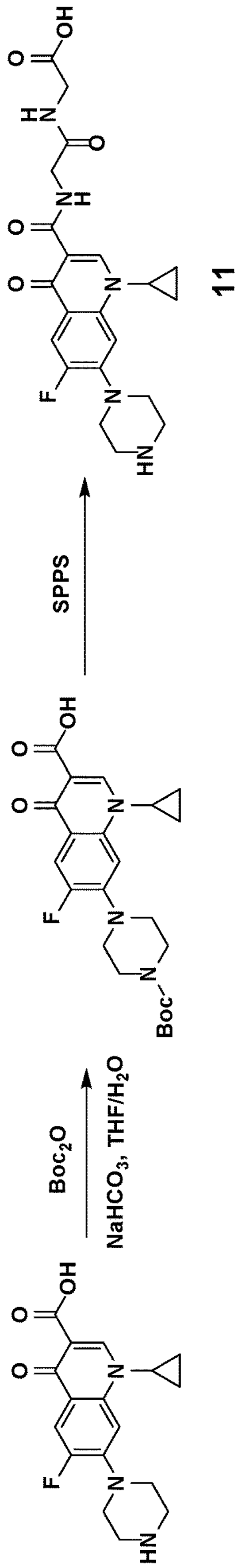
FIG. 19A is a reaction scheme showing the solid-phase synthesis of compound 11, which includes diglycine coupled directly to the available carboxylic acid group of ciprofloxacin in the absence of a linker group.

Compound 11. As shown in FIG. 19A, to a solution of ciprofloxacin (663.0 mg, 2.0 mmol) in a 1:1 mixture of THF-$H_2O$ (10 mL-10 mL), $NaHCO_3$ (672.0 mg, 8.0 mmol) and di-tert-butyl dicarbonate (523.0 mg, 2.4 mmol) were added consecutively at 0° C. with magnetic stirring. After 30 minutes, the reaction mixture was allowed to attain room temperature and stirring continued overnight. The turbid solution was extracted with ethyl acetate (2×100 mL). The aqueous layer was acidified to pH=4-5 by careful addition of half saturated cold citric acid and then extracted with methylene chloride (3×100 mL). The combined organic phase was dried over anhydrous $Na_2SO_4$ and evaporated under reduced pressure to give the Boc-protected ciprofloxacin. The crude product was used for SPPS without further purification. Then the Boc-protected ciprofloxacin was used to cap the N-terminal of the diglycine. After cleaving the compounds from resin, compound 11 was purified by reverse phase HPLC using HPLC grade acetonitrile and water with supplement of 0.1% trifluoroacetic acid as the eluents. Subsequently, the structure of the prodrug was confirmed by $^1H$ NMR and $^{13}C$ NMR spectra as follows: $^1H$ NMR (400 MHz, DMSO-d6, 25° C., ppm): δ 12.58 (s, 1H), 10.13 (dd, J=4.0, 8.0 Hz, 1H), 8.95 (s, 1H), 8.64 (s, 1H), 8.33 (dd, J=8.0, 4.0 Hz, 1H), 7.92 (d, J=12.0 Hz, 1H), 7.53 (d, J=8.0 Hz, 1H), 4.04 (d, J=4.0 Hz, 2H), 3.79 (d, J=8.0 Hz, 2H), 3.75 (m, 1H), 3.48 (m, 4H), 3.30 (m, 4H), 1.31 (m, 2H), 1.12 (m, 2H); 13C NMR (100 MHz, DMSO-d6, 25° C., ppm): δ 174.54, 171.55, 169.41, 164.38, 154.18, 151.72, 147.32, 143.55, 138.74, 122.01, 121.94, 112.01, 111.78, 110.51, 107.08, 47.03, 43.15, 42.39, 41.04, 35.50, 8.02; ESI-MS m/z calcd. for $C_{21}H_{24}FN_5O_5$ [M]+: m/z=445.45, found [M-H]−444.38.

Example 14—Antibacterial Activity and Cell Viability Studies of Ciprofloxacin Prodrugs 8, 9, 10, and 11

Figure 17A:
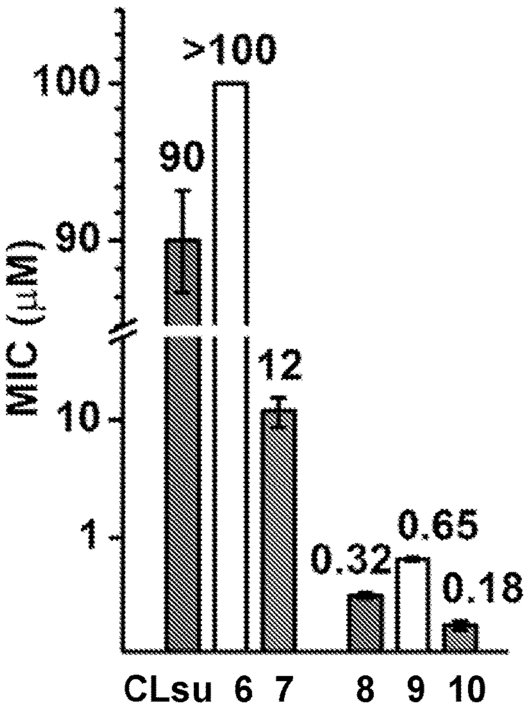
FIGS. 17A-17B are graphs showing the MIC values (FIG. 17A) against wild type *E. coli* strain (K12) and cell viability (FIG. 17B) of HS-5, HepG2, and HEK293 cells incubated with compounds 6, 7, 8, 9, and 10 for 24 hours, [6]=[7]=[8]=[9]=[10]=20 μM.
Figure 17B:
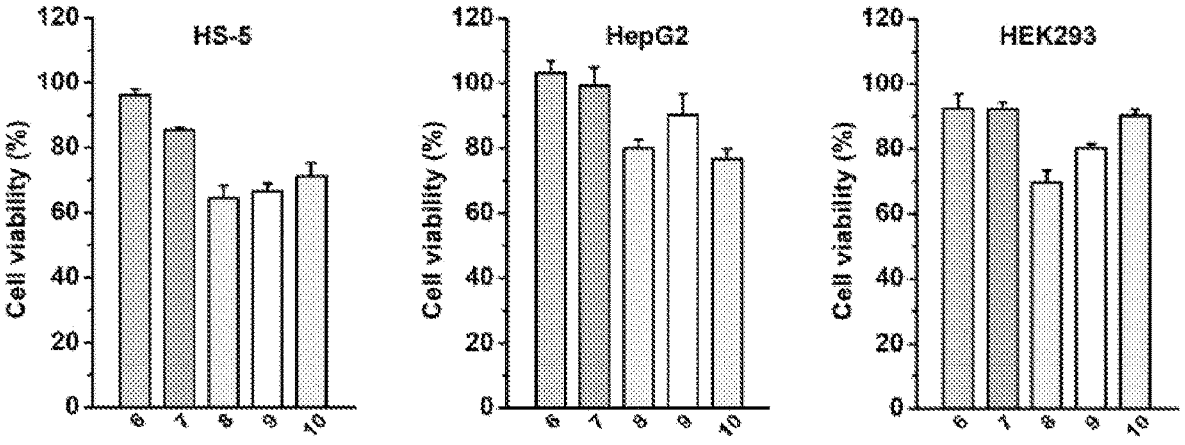
Figure 19B:
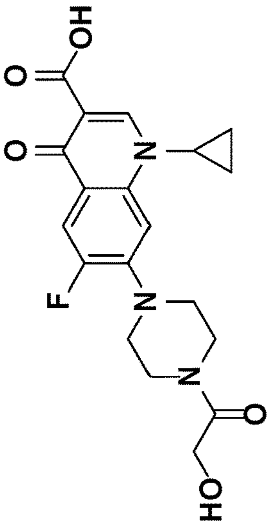
FIG. 19B is a graph showing the MIC values of intermediate 8 and diglycine-ciprofloxacine derivative 11 against a wild type *E. coli* strain (K12).
Figure 19B:
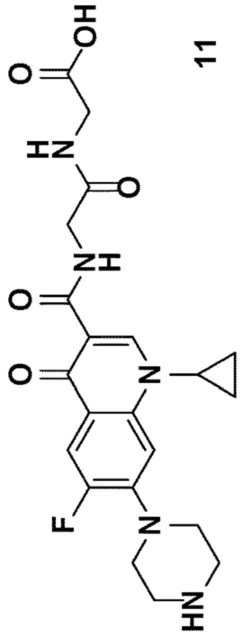
Figure 19B:
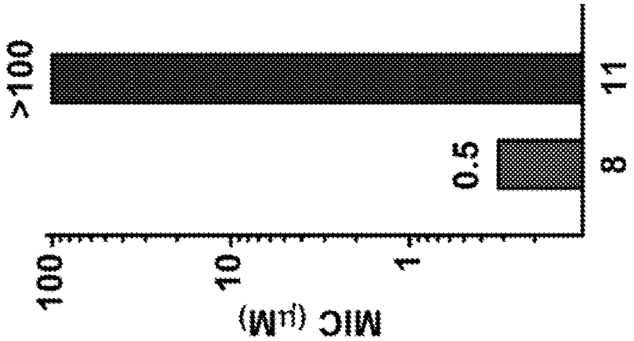

Whether the strategy shown in FIG. 1 is general for other type antibiotics was next investigated. After synthesizing the analogs shown in FIGS. 15-16, their activities against *E. coli* was investigated. Although the replacement of succinate by cyclohexane-1,2-dicarboxylic acid produces an intermediate prodrug (6) with rather low activity (MIC>100 μM), the conjugation of GG to 6 significantly increases the activity of the prodrug (7, MIC=12 μM) (FIG. 17A). Because the ciprofloxacin derivative 11, with the diglycine conjugated at the carboxylic acid of ciprofloxacin, hardly shows activity against *E. coli* (FIGS. 19A-19B), a ciprofloxacin derivative (8) was made, which has 2-hydroxyacetic acid attached to the piperazine end of ciprofloxacin, for conjugating GG-succinate to ciprofloxacin (FIG. 16). To further demonstrate the design that conjugating GG to antibiotic succinate accelerates intrabacterial hydrolysis of ester bond compared with the antibiotic succinate, for regenerating the active antibiotic against *E. coli*, compound 9, the succinate derivative of 8, was generated. Compound 9 exhibited lower antibacterial activity (MIC=0.65 μM) than that of 8 (MIC=0.32 μM). However, the conjugation of GG to 9 results in 10 (MIC=0.18 μM), which is more potent than 9 against *E. coli*. In addition, the comparison of the cytotoxicity of 6, 7, 8, 9, and 10 indicates low adverse effects against HS-5, HepG2, and HEK293 cells after the conjugation of GG (FIG. 17B). These results further confirm that the conjugation of GG is an effective strategy for activating prodrugs via rapid intrabacterial hydrolysis, thus boosting the efficacy of antibiotics and reducing side effects.

Figure 18A:
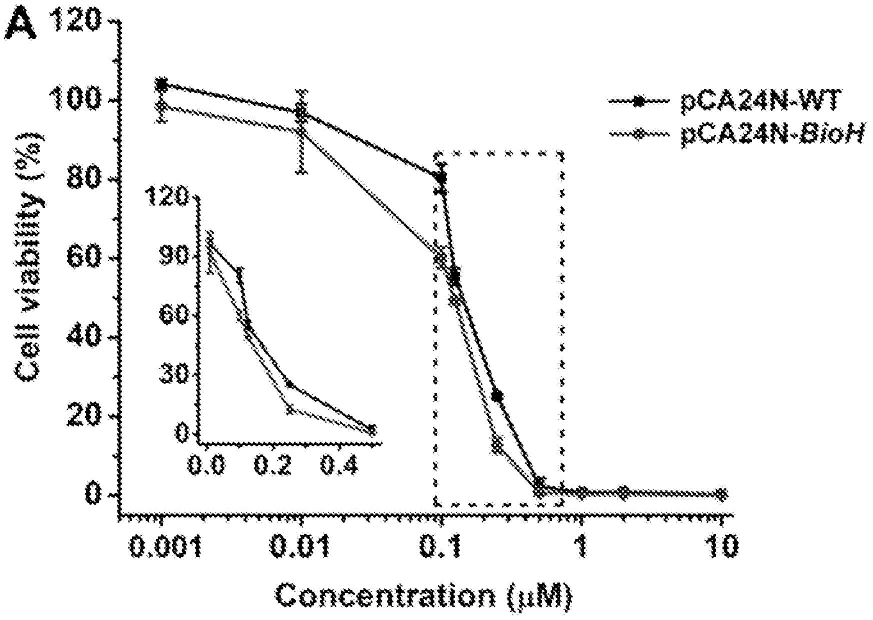
FIGS. 18A-18B are graphs showing the antibacterial activity of 10 against BioH (FIG. 18A) and YjfP (FIG. 18B) overexpressed mutants of *E. coli* (inset: corresponding magnified image of dash line square). pCA24N-WT: wild type plus plasmid pCA24N; pCA24N-BioH: wild type plus plasmid pCA24NBioH; pCA24N-YjfP: wild type plus plasmid pCA24N-YjfP. Isopropyl thiogalactose (IPTG) was used for the induction of the expression of recombinant proteins in *E. coli* and pretreated the mutants for 1 hour. [IPTG]=1 mM.
Figure 18B:
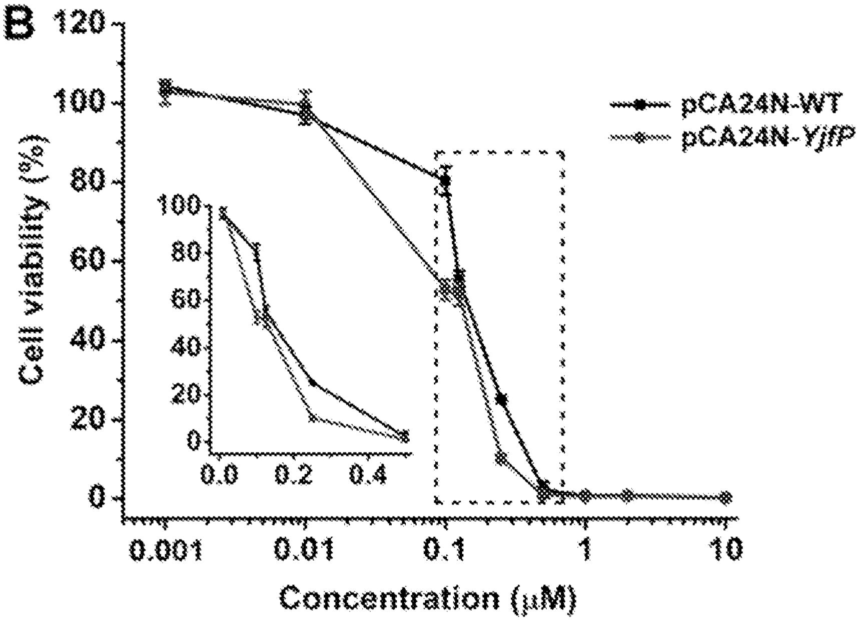

*E. coli* mutants that overexpress BioH and YjfP were also generated, respectively, and it was found that the overexpression of BioH and YjfP both increases the susceptibility of the mutant to diglycine conjugated ciprofloxacin 10 (FIGS. 18A-18B).

Discussion of Examples 13-14

Examples 13-14 demonstrate that conjugating GG to succinate prodrugs of antibiotics enhances the efficacy and improves the safety of the existing antibiotics. Although the original design aims to utilize the peptide transporters, rapid intrabacterial hydrolysis turns out to be a major factor for boosting the efficacy of the antibiotic prodrugs. This result implies rapid intrabacterial hydrolysis as a useful approach for countering efflux pumps (Li et al., "The Challenge of Efflux-Mediated Antibiotic Resistance in Gram-Negative Bacteria," Clin. Microbiol. Rev. 28(2):337-418 (2015), which is hereby incorporated by reference in its entirety) or other bacterial machineries (Salomon & Orth, "Type VI Secretion System," *Current Biology* 25(7):R265-R266 (2015), which is hereby incorporated by reference in its entirety), which warrants further investigation. Moreover, the discovery of the rate difference in the hydrolysis of succinate prodrugs between the mammalian and bacterial esterases should help develop new antibiotic prodrugs more selective to bacteria, thus increasing efficacy and decreasing adverse effects of antibiotics. Besides underscoring the versatile applications of intracellular enzymatic reactions (Ye et al., "Controlling Intracellular Macrocyclization for the Imaging of Protease Activity," *Angewandte Chemie International Edition* 50(10):2275-2279 (2011) and Takaoka et al., "Ligand-Directed Dibromophenyl Benzoate Chemistry for Rapid and Selective Acylation of Intracellular Natural Proteins," *Chemical science* 6(5):3217-3224 (2015), which are hereby incorporated by reference in their entirety), these and the preceding Examples together confirm that judicious conjugation of peptides to drugs is a powerful way for developing new therapeutics (Gao et al., "Enzyme-Instructed Molecular Self-assembly Confers Nanofibers and a Supramolecular Hydrogel of Taxol Derivative," *JACS* 131

(38):13576-13577 (2009); Cheetham et al., "Supramolecular Nanostructures Formed by Anticancer Drug Assembly," *JACS* 135(8):2907-2910 (2013); and Yang et al., "Disulfide Bond Reduction-Triggered Molecular Hydrogels of Folic Acid—Taxol Conjugates," *Organic & Biomolecular Chemistry* 11(40):6946-6951 (2013), which are hereby incorporated by reference in their entirety).

Although preferred embodiments have been depicted and described in detail herein, it will be apparent to those skilled in the relevant art that various modifications, additions, substitutions, and the like can be made without departing form the spirit of the invention and these are therefore considered to be within the scope of the invention as defined in the claims which follow.

What is claimed is:

1. A conjugated prodrug comprising:

a peptide comprising two to four amino acids, which peptide is conjugated to an antibiotic molecule via a cleavable linker, wherein:

(i) the peptide is selected from the group consisting of Gly-Gly, Gly-Gly-Gly, Gly-(D-Leu), Gly-(D-Ala), Gly-(D-Ser), Gly-Gly-Gly-Gly (SEQ ID NO: 1), Gly-Gly-(D-Phe), Gly-Gly-Phe, Gly-Phe-Gly, Gly-Gly-(D-Phe)-(D-Phe), Gly-Gly-Phe-Phe (SEQ ID NO: 3), Gly-Lys, and Gly-Asp;

(ii) the antibiotic molecule is not an aminoglycoside; and (iii) wherein the cleavable linker forms an ester bond with the antibiotic molecule.

2. The conjugated prodrug according to claim 1, wherein the peptide is Gly-Gly-Gly-Gly (SEQ ID NO: 1), Gly-Gly-(D-Phe) (D-Phe), or Gly-Gly-Phe-Phe (SEQ ID NO: 3).

3. The conjugated prodrug according to claim 1, wherein the peptide is Gly-Gly, Gly-Gly-Gly, Gly-(D-Leu), Gly-(D-Ala), Gly-(D-Ser), Gly-Gly-(D-Phe), Gly-Gly-Phe, Gly-Phe-Gly, Gly-Lys, or Gly-Asp.

4. The conjugated prodrug according to claim 1, wherein the peptide is Gly-(D-Leu), Gly-(D-Ala), Gly-(L-Ser), Gly-Gly-(L-Phe), or Gly-Gly-(L-Phe)-(L-Phe).

5. The conjugated prodrug according to claim 1, wherein the peptide comprises a glycine residue covalently attached to the cleavable linker.

6. The conjugated prodrug according to claim 1, wherein the antibiotic molecule is selected from the group consisting of aminocoumarins, β-lactams, macrolides, ketolides, lincosamides, streptogramins, quinolones, rifamycins, tetracyclines, oxazolidinones, glycylcycline, amphenicals, and polymyxins.

7. The conjugated prodrug according to claim 6, wherein the antibiotic molecule is selected from the group consisting of chloramphenicol, N-(2-hydroxyacetyl)-ciprofloxacin, novobiocin, and benzylpenicillin (penicillin G).

8. The conjugated prodrug according to claim 1, wherein the antibiotic molecule is an efflux pump inhibitor.

9. The conjugated prodrug according to claim 1, wherein the cleavable linker is selected from the group consisting of:

—C(O)—$(CH_2)_n$—C(O)— where n is an integer from 1 to 14,

—C(O)—$(CH_2)_m$—CH═CH—C(O)— where m is an integer from 1 to 10,

—C(O)—CH—CH—C(O)—,

—C(O)-(1,2-cyclohexyl)-C(O)—,

—C(O)—Ar—C(O)— where Ar is a phenyl group, naphthyl group, or multi-ring aromatic group, —C(O)—$(CH_2)_n$—C(O)—$(CH_2)_q$—C(O)—where n is an integer from 1 to 14 and q is from 1 to 10, —C(O)—$(CH_2)_m$—CH═CH—C(O)—$(CH_2)_q$—C(O)— where m is an integer from 1 to 14 and q is from 1 to 10, —C(O)—CH═CH—C(O)—$(CH_2)_q$—C(O)—where q is an integer from 1 to 10, —C(O)-(1,2-cyclohexyl)-C(O)—$(CH_2)_q$—C(O)—where q is an integer from 1 to 10, and —C(O)—Ar—C(O)—$(CH_2)_q$—C(O)—where Ar is a phenyl group, naphthyl group, or multi-ring aromatic group and q is an integer from 1 to 10.

10. The conjugated prodrug according to claim 1, which is selected from the group consisting of:

(i)

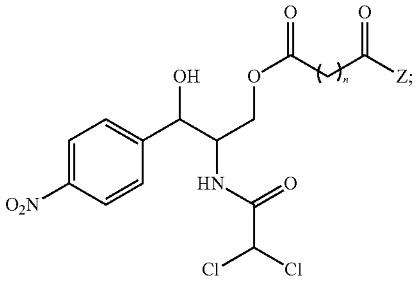

(ii)

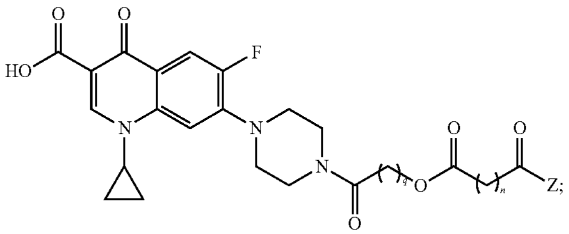

(iii)

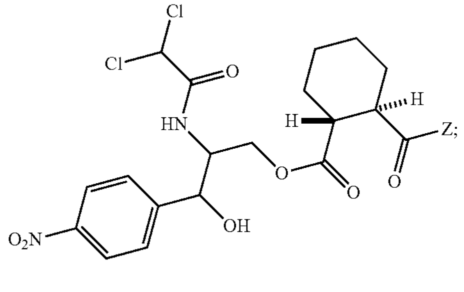

-continued (iv)

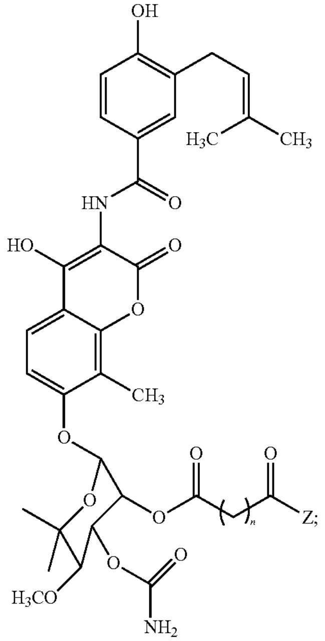

and (v)

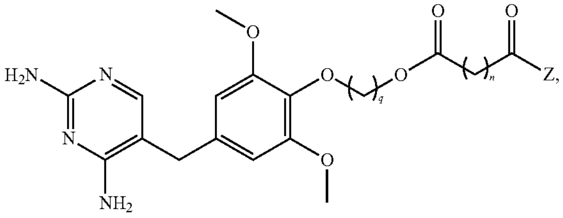

wherein n is an integer from 1 to 14, q is an integer from 1 to 10, and Z is the peptide.

11. The conjugated prodrug according to claim 10, wherein the peptide comprises a glycine residue covalently attached to the cleavable linker.

12. The conjugated prodrug according to claim 1, wherein the cleavable linker is —C(O)—$(CH_2)_n$—C(O)—, where n is an integer from 1 to 14.

13. A pharmaceutical composition comprising a pharmaceutically acceptable carrier and a conjugated prodrug according to claim 1.

14. A method of enhancing intracellular concentration of an antibiotic agent in a bacterium, the method comprising:

contacting a bacterium with an effective amount of the conjugated prodrug according to claim 1, whereby said conjugated prodrug is taken up by the bacterium and said linker is cleaved intracellularly to release the antibiotic agent from said prodrug, causing an increase in the intracellular concentration of the antibiotic agent.

* * * * *